US009359291B2

(12) United States Patent
Dix

(10) Patent No.: US 9,359,291 B2
(45) Date of Patent: *Jun. 7, 2016

(54) NON-NATURAL AMINO ACIDS

(71) Applicant: MUSC Foundation for Research Development, Charleston, SC (US)

(72) Inventor: Thomas A. Dix, Mt. Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/784,212

(22) Filed: Mar. 4, 2013

(65) Prior Publication Data

US 2013/0217632 A1 Aug. 22, 2013

Related U.S. Application Data

(63) Continuation of application No. 11/629,806, filed as application No. PCT/US2005/021580 on Jun. 17, 2005, now abandoned.

(60) Provisional application No. 60/581,333, filed on Jun. 17, 2004.

(51) Int. Cl.
*C07C 279/14* (2006.01)
*C07C 229/12* (2006.01)
(Continued)

(52) U.S. Cl.
CPC ............. *C07C 279/14* (2013.01); *C07C 229/08* (2013.01); *C07C 229/12* (2013.01); *C07C 257/14* (2013.01); *C07D 231/06* (2013.01);
(Continued)

(58) Field of Classification Search
CPC ... A61K 2300/00; A61K 38/22; A61K 38/00; A61K 47/48246; A61K 38/08; A61K 38/1709; C07K 7/06; C07K 1/006; C07K 16/28; C07K 7/083; C07C 229/26; C07C 229/08; C07D 233/48; C07D 233/46; C07D 239/14
See application file for complete search history.

(56) References Cited

U.S. PATENT DOCUMENTS 2,947,756 A 8/1960 Huebner
3,322,815 A 5/1967 Feldman et al.
(Continued)

FOREIGN PATENT DOCUMENTS

EP 0159708 A2 10/1985
ES EP 0333071 A2 * 9/1989 ............... C07K 7/06
(Continued)

OTHER PUBLICATIONS

Heyl et al. Structure-activity and conformational studies of a series of modified C-terminal hexapeptide neurotensin analogues. Int J Pept Protein Res. Sep. 1994;44(3):233-8.*
(Continued)

*Primary Examiner* — Karlheinz R Skowronek
*Assistant Examiner* — Jia-Hai Lee
(74) *Attorney, Agent, or Firm* — Saul Ewing LLP; Kathryn Doyle; Domingos J. Silva

(57) ABSTRACT

This invention relates in one aspect to non-natural desamino alkyl amino acid compounds, methods of making these compounds, and peptides containing these compounds. In one embodiment, the peptide is neurotensin (8-13) in which the N-terminus is an alpha-desamino, alpha-methyl-N,N-dimethyl-homolysine residue of the invention.

24 Claims, 17 Drawing Sheets

(51) Int. Cl.
| | |
|---|---|
| C07D 233/46 | (2006.01) |
| C07D 233/48 | (2006.01) |
| C07D 239/14 | (2006.01) |
| C07C 229/08 | (2006.01) |
| C07C 257/14 | (2006.01) |
| C07D 231/06 | (2006.01) |
| C07K 7/08 | (2006.01) |
| A61K 38/00 | (2006.01) |

(52) U.S. Cl.
CPC ............ *C07D 233/46* (2013.01); *C07D 233/48* (2013.01); *C07D 239/14* (2013.01); *C07K 7/083* (2013.01); *A61K 38/00* (2013.01)

(56) References Cited

U.S. PATENT DOCUMENTS

| | | | | |
|---|---|---|---|---|
| 3,933,797 | A | | 1/1976 | Hamanaka |
| 4,550,163 | A | * | 10/1985 | Voss ...................... C07F 9/4075 536/13.6 |
| 5,300,508 | A | | 4/1994 | Valla et al. |
| 5,393,740 | A | * | 2/1995 | Amagaya et al. ............. 514/9.4 |
| 5,589,499 | A | * | 12/1996 | Weth ............................ 514/423 |
| 6,358,992 | B1 | * | 3/2002 | Pamukcu ............. A61K 31/404 514/414 |
| 2010/0130432 | A1 | | 5/2010 | Brower et al. |

FOREIGN PATENT DOCUMENTS

| | | | | |
|---|---|---|---|---|
| GB | 1552179 | * | 9/1979 | ............ A61K 31/13 |
| WO | 0222553 | A2 | 3/2002 | |
| WO | 2006009902 | A2 | 1/2006 | |

OTHER PUBLICATIONS

Kitabgi et al. Neurotensin binding to extraneural and neural receptors: comparison with biological activity and structure—activity relationships. Mol Pharmacol. Jul. 1980;18(1):11-9.*

Patani et al. Bioisosterism: A Rational Approach in Drug Design. Chem. Rev. 1996, 96, 3147-3176.*

McDonald et al. Inhibition of endothelial cell amino acid transport System y+ by arginine analogs that inhibit nitric oxide synthase. Biochim Biophys Acta. Feb. 21, 1997;1324(1):133-41.*

Frackenpohl et al. The outstanding biological stability of beta- and gamma-peptides toward proteolytic enzymes: an in vitro investigation with fifteen peptidases. Chembiochem. Jun. 1, 2001;2(6):445-55.*

Baussanne, I. et al., "Asymmetric Synthesis of 3-Substituted Pyrrolidones via α-Alkylation of a Chiral Non-Racemic γ-lactam," Tetrahedron: Asymmetry, vol. 9, No. 5, pp. 797-804, 1998.

Chebib, M. et al., "Analogues of γ-aminobutyric acid (GABA) and trans-2-aminocrotonic acid (TACA) substituted in the 2 position as GABAc Receptor Antagonists," Br. J. Pharmacol., vol. 122, No. 8, pp. 1551-1560, 1997.

Duke, R.K. et al., "Synthesis and Resolution of 2-Methyl Analogues of GABA," Tetrahedron Asymmetry, vol. 15, pp. 1745-1751, 2004.

Kiseleva, I.N. et al., "Synthesis of New Derivatives of 3-Pyrrolidones and 4-Aminobutanoic Acids," Zh. Organicheskoi Khimii, vol. 10, No. 10, pp. 2224-2225, 1974. (English abstract).

Kobayashi, T., "Uber die Konstitution des Methyl-Eserathols und die optische Spaltung von d,1-Eserathol," Synthetische Versuche uber Eserin. V, pp. 143-163, 1938.

Larsen, S.D. et al., "Synthesis and Biological Activity of Analogues of the Antidiabetic/Antiobesity Agent 3-Guanidinopropionic Acid: Discovery of a Novel Aminoguanidinoacetic Acid Antidiabetic Agent," J. Med. Chem. vol. 44, pp. 1217-1230, 2001.

Mokrzan, E.M. et al., "Methylmercury-Thiol Uptake into Cultured Brain Capillary Endothelial Cells on Amino Acid System L1," The Journal of Pharmacology and Experimental Therapeutics, vol. 272, No. 3, pp. 1277-1284, 1995.

Overberger, C.G. et al., "The Synthesis of Some Optically Active C-Methylated 2-Oxohexamethyleneimines," Journal of Polymer Science: Part A-1, vol. 6, pp. 513-526, 1968.

Porter, D.J.T. et al., "Enzymatic Elimination of Fluoride from α-fluoro-β-alanine," Biochemical Pharmacology, vol. 50, No. 9, pp. 1475-1484, 1995.

Vystrcil, A. et al., "Addition of Amines to Methyl Methacrylate and the Effect of Water (on the Reation Product)," XP-002633489, vol. 44, pp. 262-269, 1950. (English abstract).

Hadden, M.K. et al., "Design, Synthesis and Evaluation of the Antipsychotic Potential of Orally Bioavailable Neurotensin (8-13) Analogues Containing Non-Natural Arginine and Lysine Residues," Neuropharmacology, 2005, vol. 49, No. 8, pp. 1149-1159.

* cited by examiner

III

IV

[A]

25

KH28: n=5; R=CH$_3$, R'=NH$_2$
KH29: n=3; R=CH$_3$, R'=NH(CH$_3$)
KH30: n=3; R=CH$_3$, R'=N(CH$_3$)$_3^+$

SEQUENCE LISTING

```
<160> NUMBER OF SEQ ID NOS: 12

<210> SEQ ID NO 1
<211> LENGTH: 13
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: pyroglutamic acid

<400> SEQUENCE: 1

Xaa Leu Tyr Glu Asn Lys Pro Arg Arg Pro Tyr Ile Leu
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Chemically synthesized

<400> SEQUENCE: 2

Arg Arg Pro Tyr Ile Leu
1               5

<210> SEQ ID NO 3
<211> LENGTH: 6
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: 7-amino-2-methyl-heptanoic acid
<220> FEATURE:
<221> NAME/KEY: MISC_FEATURE
<222> LOCATION: (5)..(5)
<223> OTHER INFORMATION: L-tert-leucine
```

```
<400> SEQUENCE: 3

Xaa Arg Pro Tyr Xaa Leu
1               5

<210> SEQ ID NO 4
<211> LENGTH: 6
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: 5-(N-methylamino)-2-methyl-pentanoic acid
<220> FEATURE:
<221> NAME/KEY: MISC_FEATURE
<222> LOCATION: (5)..(5)
<223> OTHER INFORMATION: L-tert-Leu

<400> SEQUENCE: 4

Xaa Arg Pro Tyr Xaa Leu
1               5

<210> SEQ ID NO 5
<211> LENGTH: 6
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: 5-(trimethylammoonium)-2-methyl-pentanoic acid
<220> FEATURE:
<221> NAME/KEY: MISC_FEATURE
<222> LOCATION: (5)..(5)
<223> OTHER INFORMATION: L-tert-Leu

<400> SEQUENCE: 5

Xaa Arg Pro Tyr Xaa Leu
1               5

<210> SEQ ID NO 6
<211> LENGTH: 6
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: 2-azido-L-7-amino-heptanoic acid
<220> FEATURE:
<221> NAME/KEY: MISC_FEATURE
<222> LOCATION: (5)..(5)
<223> OTHER INFORMATION: L-tert-leucine

<400> SEQUENCE: 6

Xaa Arg Pro Tyr Xaa Leu
1               5

<210> SEQ ID NO 7
<211> LENGTH: 6
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: 2-azido-5-(2,3-diethylguanidino)pentanoic acid
```

```
<220> FEATURE:
<221> NAME/KEY: MISC_FEATURE
<222> LOCATION: (6)..(6)
<223> OTHER INFORMATION: L-tert-leucine

<400> SEQUENCE: 7

Xaa Arg Pro Tyr Ile Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: 5-(N-methyl-amino)-2-azido-pentanoic acid
<220> FEATURE:
<221> NAME/KEY: MISC_FEATURE
<222> LOCATION: (6)..(6)
<223> OTHER INFORMATION: L-tert-leucine

<400> SEQUENCE: 8

Xaa Arg Pro Tyr Ile Xaa
1               5

<210> SEQ ID NO 9
<211> LENGTH: 6
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: 5-(trimethylammonium)-2-azido-pentanoic acid
<220> FEATURE:
<221> NAME/KEY: MISC_FEATURE
<222> LOCATION: (6)..(6)
<223> OTHER INFORMATION: L-tert-leucine

<400> SEQUENCE: 9

Xaa Arg Pro Tyr Ile Xaa
1               5

<210> SEQ ID NO 10
<211> LENGTH: 6
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: 5-(N-methyl-amino)-2-methyl-pentanoic acid
<220> FEATURE:
<221> NAME/KEY: MISC_FEATURE
<222> LOCATION: (6)..(6)
<223> OTHER INFORMATION: L-tert-leucine

<400> SEQUENCE: 10

Xaa Arg Pro Tyr Ile Xaa
1               5
```

```
<210> SEQ ID NO 11
<211> LENGTH: 6
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: 5-(trimethylammonnium)-2-methyl-pentanoic acid
<220> FEATURE:
<221> NAME/KEY: MISC_FEATURE
<222> LOCATION: (6)..(6)
<223> OTHER INFORMATION: L-tert-leucine

<400> SEQUENCE: 11

Xaa Arg Pro Tyr Ile Xaa
1               5

<210> SEQ ID NO 12
<211> LENGTH: 5
<212> TYPE: PRT
<213> ORGANISM: Artificial Sequence
<220> FEATURE:
<223> OTHER INFORMATION: Chemically synthesized

<400> SEQUENCE: 12

Arg Pro Tyr Ile Leu
1               5
```

NON-NATURAL AMINO ACIDS

CROSS-REFERENCE TO RELATED APPLICATIONS

The present application is a continuation of, and claims priority to, U.S. patent application Ser. No. 11/629,806, filed Sep. 10, 2007, which is a 35 U.S.C. §371 national phase application of, and claims priority to, International Application No. PCT/US2005/21580, filed Jun. 17, 2005, and published under PCT Article 21(2) in English, which claims priority under 35 U.S.C. §119(e) to U.S. Provisional Application No. 60/581,333, filed Jun. 17, 2004, all of which applications are hereby incorporated by reference in their entireties herein.

FIELD OF THE INVENTION

This invention relates to non-natural desamino, alkyl amino acids, methods of making them, their utilization in peptides, and the therapeutic, diagnostic and screening use of those peptides.

BACKGROUND OF THE INVENTION

The influence that some non-natural amino acids have on the structural and biological activity of peptides has been briefly studied. For example, Moore et al. (*Can. J. Biochem.* 1978, 56, 315) disclosed the effect of the basic amino acid side chain length and the penultimate residue on the hydrolysis of benzoyldipeptides by carboxylicpeptidase B[1] (CPB). Non-natural amino acids including homolysine and homoarginine were incorporated into small peptide chains, and the kinetic parameters were determined for the CPB catalyzed hydrolysis of the peptide. Also, Lindeberg et al. (*Int. J. Peptide Protein Res.* 1977, 10, 240) disclosed the synthesis of 1-deamino-4-L-valine-8-DL-homolysine-vasopressin and protected 1-deamino-4-L-valine-8-D-lysine-vassopressin in which non-natural amino acids were incorporated. The non-natural amino acids were formed by addition of a methylene group to lysine and arginine to generate the non-natural amino acids homolysine and homoarginine, respectively. The study revealed that peptides with homolysine and homoarginine reduced the antidiuretic activity of the peptides.

Naturally occurring endogenous peptides are ideal drug candidate leads by virtue of their myriad activities in promoting and regulating biological processes. Inherent in the chemistry and biology of peptides, however, are several factors that also make them poor drug candidates. Peptides most often exert localized effects and are rapidly degraded within the body. In addition, most peptides are unable to cross biological membranes, including the small intestine and blood brain barrier (BBB). Finally, peptides often bind to more than one receptor or receptor subtype, thus rarely showing the selectivity required of a viable drug candidate. Therefore, for a peptide to become a viable drug candidate, improvements in blood stability, receptor selectivity, and barrier crossing should be made without eliminating inherent binding affinity.

Numerous strategies have been developed as methods for improving peptide stability, including N- and C-terminal modifications to prevent exopeptidase activity, amide backbone modifications, and the introduction of conformational constraints to disguise peptides from peptidase degradation. Other therapeutic compounds employ a prodrug moiety intended to modify its overall hydrophobicity, which can result in the compound crossing biological membranes. In this case, the compound is cleaved into its active component by endogenous enzymes. While each of these strategies has been used to improve peptides as drug candidates, a universal solution for creating stable, receptor-selective peptides that cross biological barriers has not been discovered.

Consequently, there is a need in the art for non-natural amino acids and for peptides incorporating such acids to achieve superior effects, such as, for example, improved diagnostic or disease fighting activity. Thus, the non-natural amino acid concept could be applied to development of new peptide pharmaceuticals. One example of such a development is the application to neuropeptides such as neurotensin.

SUMMARY OF CERTAIN EMBODIMENTS OF THE INVENTION

As used in the specification and the appended claims, the singular forms "a," "an" and "the" include plural referents unless the context clearly dictates otherwise.

Variables, such as $R_1$-$R_3$, n, z, X, Y, $C_\alpha$ and $C_\beta$, throughout the application are the same variables as defined herein unless stated to the contrary.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Preferred alkyl groups herein contain from 1 to 6 carbon atoms.

The term "alkenyl" as used herein refers to a hydrocarbon group of 2 to 24 carbon atoms, with preferred groups within this class containing 2 to 6 carbon atoms, and structural formula containing a carbon-carbon double bond.

The term "alkynyl" as used herein refers to a hydrocarbon group of 2 to 24 carbon atoms, with preferred groups within this class containing 2 to 6 carbon atoms, and a structural formula containing a carbon-carbon triple bond.

As used herein, especially in reference to alkyl, alkenyl and alkynyl, unless defined otherwise, the term "lower" refers to a moiety having from 1 to 6 carbon atoms, preferably 1 to 4 carbon atoms, more preferably 1 to 2 carbon atoms.

The term "alkylating agent" as provided herein is a compound with the structural formula RX, where R is an alkyl, alkenyl or alkynyl group as previously described, and X, which is preferably a halide such as chloride, bromide or iodide.

As used herein, the term "non-natural amino acid" refers to an organic compound that is a congener of a natural amino acid in that it has a structure similar to a natural amino acid so that it mimics the structure and reactivity of a natural amino acid. The non-natural amino acid as defined herein generally increases or enhances the properties of a peptide (e.g., selectivity, stability) when the non-natural amino acid is either substituted for a natural amino acid unit of a peptide or otherwise incorporated into a peptide.

As used herein, the term "peptide" refers to a class of compounds composed of amino acids chemically bound together. In general, the amino acids are chemically bound together via amide linkages (—CONH—); however, the amino acids may be bound together by other chemical bonds known in the art. For example, the amino acids may be bound by amine linkages. Peptide as used herein includes oligomers of amino acids and small and large peptides, including polypeptides.

As used herein, the term "activity" refers to a biological activity.

As used herein, the term "pharmacological activity" refers to the inherent physical properties of a peptide or polypeptide. These properties include but are not limited to half-life, solubility, and stability and other pharmacokinetic properties.

The term "organic acid salt" as used herein refers to the salt form of an amine group with an alkyl or aryl $C_1$-$C_9$ carboxylic, sulfonic, or phosphoric acid.

The term "inorganic acid salt" as used herein refers to the salt form of an amine group with a mineral acid such as hydrochloric, sulfuric, sulfonic, phosphoric, nitric, nitrous, or hydrobromic acid.

The term "aromatic of $C_6$ to $C_{18}$" as used herein refers to an aromatic hydrocarbon such as phenyl, naphthyl, anthracenyl, or an arylalkyl hydrocarbon such as benzyl, phenethyl or naphthylmethylenyl.

The term "heteraromatic of $C_4$ to $C_{18}$ and of one or two heteroatoms selected from oxygen, sulfur and nitrogen in any combination" as used herein refers to a heteroaromatic hydrocarbon containing one or two heteroatoms or an alkyl heteroaromatic hydrocarbon such as thienyl, furyl, pyrrolyl, azathienyl, azafuryl, pyridinyl, thiapyridinyl, pyrazinyl, methylenylpyridinyl, ethylenylpyridinyl, methylenylpyrrolyl and the like.

The chemical, pharmaceutical and biological terms used herein follow the ordinary and customary meanings one of skill, such as a Ph.D. researcher in the field would attribute to them. Such meanings may be found in appropriate technical dictionaries and treatises such as but not limited to "Hawley's Condensed Chemical Dictionary", 11$^{th}$ Ed., Sax and Lewis Editors, Van Nostrand Reinhold Publishing, New York, N.Y. 1987; "Concise Chemical and Technical Dictionary", 4$^{th}$ enlarged Ed. Bennett Editor, Chemical Publishing Inc., New York, N.Y., 1986, "The Merck Index" 11$^{th}$ and succeeding Editions, Merck & Co. Rahway, N.J. 1989 and more recent; "Advanced Organic Chemistry" 4$^{th}$ Ed., J. March, Wiley Interscience, New York, N.Y. 1992; "Concise Dictionary of Biomedicine and Molecular Biology", Pei-Show Juo Ed., CRC Press, New York, N.Y. 1996; "Molecular Cell Biology", Daniell, Lodish, Baltimore, Scientific American Books, New York, N.Y. 1986; the disclosures of all of these dictionaries and treatises are incorporated herein by reference.

The present invention concerns alpha-desamino, alpha-alkyl amino acid compounds (desamino, alkyl amino acid compounds) that are capable of carrying positively charged side chains, their synthesis, their application as substitutes for natural amino acid moieties of biologically active peptides and the resulting peptides as well. In particular, alpha-alkyl, alpha-desamino arginine, lysine and ornithine as well as their substituted and derivatized side chain analogs constitute preferred embodiments of the invention. These desamino, alkyl amino acid compounds can be substituted for arginine and/or lysine moieties in any known, biologically active peptide such that the substituted peptide will be truncated at the substitution position. Alternatively, these desamino, alkyl amino acid compounds can be coupled to the amino group of the N-terminus of any known biologically active peptide to produce an extended peptide. The truncated and extended peptides have significant biological selectivity and biological half lives owing to their resistance toward amino peptidase degradation.

In a first aspect, the invention relates to a non-natural desamino, alkyl amino acid compound having Formula I:

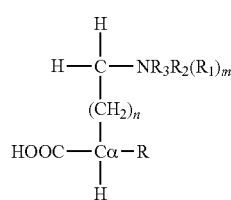

wherein
n is an integer of from 0 to 5, preferably, 2 to 5;
m is zero or an integer of 1;

R is a straight or branched chain alkyl group of $C_1$-$C_6$, or an aromatic group of $C_6$-$C_{18}$ or a corresponding substituted aromatic group with one or two substituents selected from halogen, alkyloxy, carboxy, amide or alkyl in any combination, or a heteroaromatic group of $C_4$-$C_{18}$ and one or two heteroatoms selected from oxygen, sulfur and nitrogen in any combination or a corresponding substituted heteraromatic group with one or two substituents selected from halogen, alkyloxy, carboxy, amide or alkyl in any combination;

$R_1$, $R_2$, and $R_3$ are, independently, hydrogen or branched or straight chain alkyl, alkenyl or alkynyl of $C_1$-$C_6$ or an aromatic group of $C_6$-$C_{18}$ or a corresponding substituted aromatic group with one or two substituents selected from halogen, alkyloxy, carboxy, amide or alkyl in any combination, or a heteroaromatic group of $C_4$-$C_{18}$ and one or two heteroatoms selected from oxygen, sulfur and nitrogen in any combination or a corresponding substituted heteroaromatic group with one or two substituents selected from halogen, alkyloxy, carboxy, amide or alkyl in any combination and with the proviso that a maximum of two of $R_1$, $R_2$, and $R_3$ may be selected to be the aromatic, substituted aromatic, heteroaromatic or substituted heteroaromatic group;

Cα is a carbon atom having either R or S stereochemistry; or an ester, amide, alkyl amide or metal cation or ammonium salt of the carboxylic acid group thereof, or an organic or inorganic acid salt of the amine group thereof, or any combination thereof.

In a second aspect, the invention relates to a non-natural desamino, alkyl amino acid compound of the formula II:

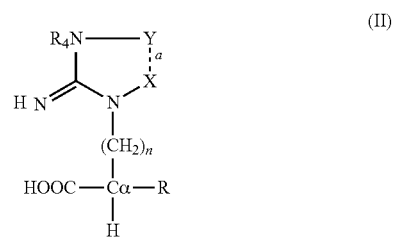

wherein
n is an integer of from 0 to 6, preferably, 2 to 5;
when dashed line a is not present, X and Y are independently, hydrogen or lower branched or straight chain alkyl, alkenyl or alkynyl of $C_1$-$C_6$;
when dashed line a is present, X—Y is $(CH_2)_z$, wherein z is an integer of from 1-8, preferably, 2 to 4;
R is a straight or branched chain alkyl group of $C_1$-$C_6$, or an aromatic group of $C_6$-$C_{18}$ or a corresponding substituted aromatic group with one or two substituents selected from halogen, alkyloxy, carboxy, amide or alkyl in any combination, or a heteroaromatic group of $C_4$-$C_{18}$ and one or two heteroatoms selected from oxygen, sulfur and nitrogen in any combination or a corresponding substituted heteraromatic group with one or two substituents selected from halogen, alkyloxy, carboxy, amide or alkyl in any combination;

$R_4$ is hydrogen or lower branched or straight chain alkyl, alkenyl or alkynyl of $C_1$-$C_6$, or an aromatic group of $C_6$-$C_{18}$ or a corresponding substituted aromatic group with one or two substituents selected from halogen, alkyloxy, carboxy, amide or alkyl in any combination, or a heteroaromatic group of $C_4$-$C_{18}$ and one or two heteroatoms selected from oxygen, sulfur and nitrogen in any combination or a corresponding substituted heteraromatic group with one or two substituents selected from halogen, alkyloxy, carboxy, amide or alkyl in any combination, and;

$C_\alpha$ is a carbon atom and the stereochemistry at $C_\alpha$ is either R or S;

or an ester, amide, alkyl amide or metal cation or ammonium salt of the carboxylic acid group thereof, or an organic or inorganic acid salt of the amine group thereof, or any combination thereof.

A third aspect of the present invention relates to a non-natural desamino, alkyl amino acid compound of the formula III:

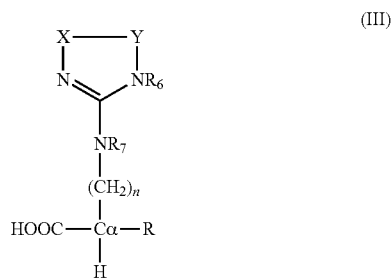

wherein n is an integer of from 0 to 5, preferably, 2 to 5;

X—Y is $(CH_2)_z$, wherein z is an integer of from 0 to 6, preferably, 2 to 4;

R is a straight or branched chain alkyl group of $C_1$-$C_6$, or an aromatic group of $C_6$-$C_{18}$ or a corresponding substituted aromatic group with one or two substituents selected from halogen, alkyloxy, carboxy, amide or alkyl in any combination, or a heteroaromatic group of $C_4$-$C_{18}$ and one or two heteroatoms selected from oxygen, sulfur and nitrogen in any combination or a corresponding substituted heteraromatic group with one or two substituents selected from halogen, alkyloxy, carboxy, amide or alkyl in any combination;

$R_6$, and $R_7$ are, independently, hydrogen or lower branched or straight chain alkyl, alkenyl or alkynyl of $C_1$-$C_6$, or an aromatic group of $C_6$-$C_{18}$ or a corresponding substituted aromatic group with one or two substituents selected from halogen, alkyloxy, carboxy, amide or alkyl in any combination, or a heteroaromatic group of $C_4$-$C_{18}$ and one or two heteroatoms selected from oxygen, sulfur and nitrogen in any combination or a corresponding substituted heteraromatic group with one or two substituents selected from halogen, alkyloxy, carboxy, amide or alkyl in any combination; and $C_\alpha$ is a carbon atom and the stereochemistry at $C_\alpha$ is either R or S;

or an ester, amide, alkyl amide or metal cation or ammonium salt of the carboxylic acid group thereof, or an organic or inorganic acid salt of the amine group thereof, or any combination thereof.

A fourth aspect of the invention relates to a non-natural desamino, alkyl amino acid compound of the formula IV:

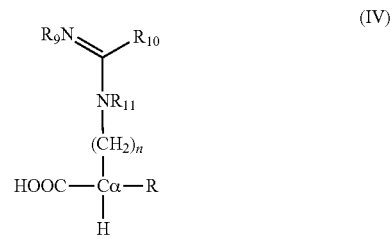

wherein n is an integer of from 0 to 5, preferably, 2 to 4;

R is a straight or branched chain alkyl group of $C_1$-$C_6$, or an aromatic group of $C_6$-$C_{18}$ or a corresponding substituted aromatic group with one or two substituents selected from halogen, alkyloxy, carboxy, amide or alkyl in any combination, or a heteroaromatic group of $C_4$-$C_{18}$ and one or two heteroatoms selected from oxygen, sulfur and nitrogen in any combination or a corresponding substituted heteraromatic group with one or two substituents selected from halogen, alkyloxy, carboxy, amide or alkyl in any combination;

$R_9$, $R_{10}$, and $R_{11}$ are, independently, hydrogen or lower branched or straight chain alkyl, alkenyl or alkynyl of $C_1$-$C_6$, or an aromatic group of $C_6$-$C_{18}$ or a corresponding substituted aromatic group with one or two substituents selected from halogen, alkyloxy, carboxy, amide or alkyl in any combination, or a heteroaromatic group of $C_4$-$C_{18}$ and one or two heteroatoms selected from oxygen, sulfur and nitrogen in any combination or a corresponding substituted heteraromatic group with one or two substituents selected from halogen, alkyloxy, carboxy, amide or alkyl in any combination and with the proviso that a maximum of two of $R_9$, $R_{10}$, and $R_{11}$ may be selected to be the aromatic, substituted aromatic, heteroaromatic or substituted heteroaromatic group; and $C_\alpha$ is a carbon atom and the stereochemistry at $C_\alpha$ is either R or S;

or an ester, amide, alkyl amide or metal cation or ammonium salt of the carboxylic acid group thereof, or an organic or inorganic acid salt of the amine group thereof, or any combination thereof.

A further aspect of the invention relates to the addition of the non-natural desamino, alkyl amino acid compounds of the invention to the N-terminus amino group of biologically active peptides or their substitution for naturally occurring congener amino acid moieties of biologically active peptides. Preferred congener moieties include arginine and/or lysine.

The addition to the N-terminus amino group of a known, biologically active peptide provides an extended peptide that has selective, long lasting biological activity of the same kind as the known, biologically active peptide. The addition can be accomplished by known methods for coupling acid and amine groups together to form amide bonds, including use of acyl azide coupling, carbodiimide coupling, acid ion exchange resin, triaminoboranes and enzyme coupling. A preferred method involves the use of an amino exopeptidase under conditions that promote the peptide bond formation. In some embodiments of the invention, the semisynthetic peptides are produced by substituting a non-natural amino acid compound for the N-terminal arginine residue of NT (8-13), e.g., ABS201.

Preferred embodiments of the peptides on which the extended peptides are based include biologically active peptides useful for treatment or prevention of malconditions. A list of preferred categories and examples is included in the sections below. Some preferred categories include but are not limited to transcription factors, ligands for cellular receptors, hormones and extracellular binding peptides. Some preferred examples include but are not limited to enkephlin, LHRH and analogs, neuropeptides, glycoincretins, integrin and analogs, glucagons and glucagon-like peptides, antithrombotic peptides, cytokines and interleukins, transferrins, interferons, endothelins, natriuretic hormones, extracellular kinase ligands, angiotensin enzyme inhibitors, peptide antiviral compounds, thrombin, substance P, substance G, somatotropin, somatostatin, GnRH and analogues, secretin, bradykinin, vasopressin and analogues, insulin and analogs thereof, growth factors, as well as others. The extended peptide is formed by coupling the N-terminus amino group of a basis peptide to the carboxyl group of a desamino, alkyl amino acid compound of the invention.

The substitution of desamino, alkyl amino acid moiety for an arginine or lysine moiety of a biologically active peptide provides a truncated peptide having selective, long-lasting biological activity. Any known biologically active peptide having an arginine and/or lysine moiety within its amino acid sequence can serve as the basis for the corresponding truncated peptide. Beginning at that ARG or LYS moiety, the truncated peptide will have the same downstream sequence as the known, biologically active peptide but the upstream sequence will be absent. In addition, that ARG or LYS moiety will be exchanged for a desamino, alkyl amino acid moiety, thus providing the truncated peptide. Several known biologically active peptides are penultimately formed as pro-peptides with an arginine or lysine moiety at the pro-peptide or precursor cleavage position, or are formed as final peptides containing an arginine or lysine moiety at a position that can be cleaved to provide an active truncated peptide. Trypsin is an enzyme specific for such cleavage points. Examples include glucagon-like peptide, neurotensin, proinsulin, and thrombin. The truncated versions of these examples with a desamino, alkyl amino acid compound substituted for the arginine or lysine moiety provide selective, long-lasting biological activity.

A further aspect of the invention includes pharmaceutical and cosmetic compositions of the desamino, alkyl amino acid compound, of the extended or truncated peptide, and combinations thereof. Unit dosage forms and biologically effective formulations of the pharmaceutical compositions are included. The cosmetic formulations include appropriate oil, creme, wax or aqueous base cosmetic carriers.

Yet another aspect of the invention includes methods of screening, diagnosis and treatment using the desamino, alkyl amino acid compounds of the invention and/or the addition or truncated peptides.

One embodiment of the invention is a truncated neurotensin peptide having a desamino, alkyl amino acid as its N-terminus amino acid moiety.

The invention also provides processes and intermediates disclosed herein that are useful for preparing compounds of the inventions, such as compounds of Formula I, II, III, and/or IV and peptides that contain such compounds. One class of such intermediates includes the N-protected or carboxyl protected or N— and carboxyl protected compounds of Formulas I, II, III and IV. These protected intermediates are described in detail in the following sections of the application. Another class of such intermediates includes the carboxylate salts of the compounds of Formulas I, II, III and IV, the organic or inorganic acid amine salts of those compounds and the double salts (carboxylate, amine salts).

DETAILED DESCRIPTION OF THE INVENTION

The present invention is directed to certain desamino, alkyl amino acid compounds, their incorporation as extenders or as congeners in known biologically active peptides, and the use of the compounds and peptides in medical diagnosis, treatment and screening. Several aspects of the invention concern the mimicry of the alkyl desamino amino acid compounds for the natural amino acids arginine and/or lysine. By their use as congeners for these natural amino acid moieties in known biologically active peptides, truncated versions of the peptides can be prepared in which the biological activity is more selective and longer lasting than that of the known peptide. By their use as extenders, their position as the N-terminal moiety adduct of a known biologically active peptide will also provide longer lasting biological activity than that of the known peptide.

Figure 1:
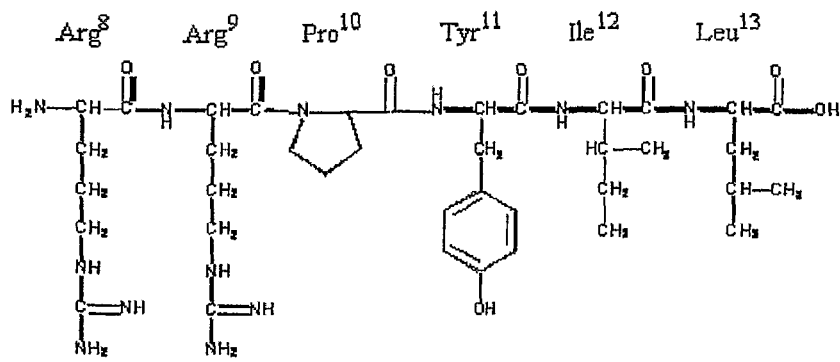
FIG. 1. Structure comparisons of NT(8-13), ABS201, and peptide 30.
Figure 1:
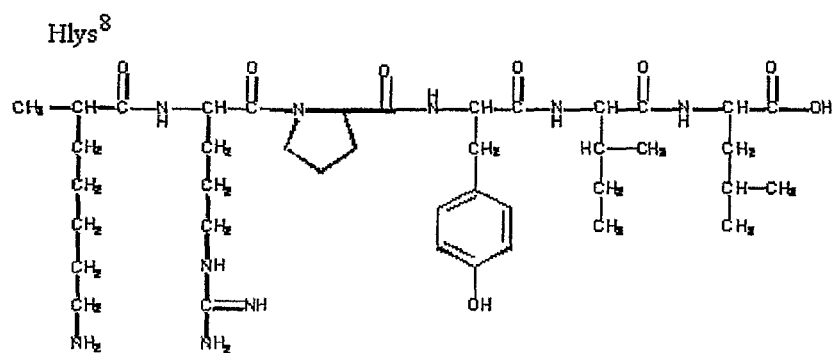
Figure 1:
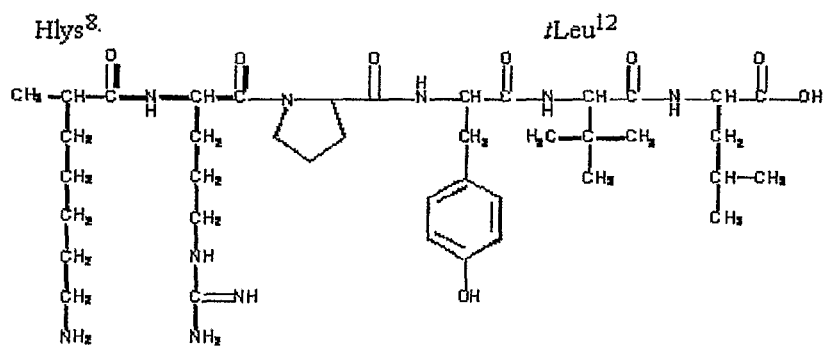

An example of the use of the desamino, alkyl amino acid compounds of the invention in a truncated peptide is provided by neurotensin. Neurotensin (NT) is a 13 amino acid peptide having neurological properties. Its cleavage at AA7 to produce truncated neurotensin (8-13) provides a peptide having selective biological activity. According to the invention, conversion of the AA8 arginine to a desamino, alkyl amino acid moiety results in a peptide also having significant and selective biological activity. The examples of NT and the converted versions are shown in FIG. 1.

The biologically active peptides of the present invention have the desamino, alkyl amino acid moiety as their N-terminal moiety. These peptides have known amino acid sequences of biologically active amino acids wherein the desamino alkyl amino acid is either covalently coupled through an amide bond with the N-terminus amine group of the known peptide (extended peptide) or is substituted for its corresponding congener moiety (analogous natural amino acid moiety) within the peptide (truncated version). In another alternative, the peptide becomes truncated at the position of substitution so that the desamino, alkyl amino acid moiety becomes the new N-terminus and the amino acid residues upstream of this position are no longer part of the sequence (truncated peptide). The extended and truncated peptides can have longer lifetimes in vivo and can have biological activities like those of the natural peptides except that the activities will be more selective.

One aspect of the desamino, alkyl amino acid compounds of the invention is provided by Formula I given above. Preferred embodiments of Formula I include those wherein $R_1$, $R_2$, and $R_3$ are independently, hydrogen or lower branched or straight chain alkyl of $C_1$-$C_5$, more preferably hydrogen or methyl. In another embodiment, n is 4. In yet a further embodiment, R is methyl, ethyl or propyl. Additional preferred embodiments include those wherein R is methyl, ethyl, propyl or butyl and:

a) n is 4, m is 0, $R_1$ is hydrogen, $R_2$ is methyl, the compound of formula I is an acid, and the stereochemistry at $C_\alpha$ is R or S;

b) n is 4, m is 1, $R_1$ and $R_2$ are methyl, $R_3$ is hydrogen or methyl, the compound of formula I is an acid, the stereochemistry at $C_\alpha$ is R or S;

c) n is 4, m is 1, $R_1$ is methyl, $R_2$, and $R_3$ are hydrogen, the compound of formula I is an acid, the stereochemistry at $C_\alpha$ is R or S;

d) n is 4, m is 1, $R_1$, $R_2$, and $R_3$ are hydrogen, the compound of formula I is an acid, and the stereochemistry at $C_\alpha$ is R or S;

e) n is 3, m is 0, $R_1$ and $R_2$ are methyl, the compound of formula I is an acid, the stereochemistry at $C_\alpha$ is R or S;

f) n is 3, m is 0, $R_1$ and $R_2$ are ethyl, the compound of formula I is an acid, the stereochemistry at $C_\alpha$ is R or S;

g) n is 3, m is 0, $R_1$ and $R_2$ are propyl, the compound of formula I is an acid, the stereochemistry at $C_\alpha$ is R or S;

h) n is 3, m is 0, $R_1$ and $R_2$ are butyl, the compound of formula I is an acid, the stereochemistry at $C_\alpha$ is R or S;

i) n is 2, m is 0, $R_1$ and $R_2$ are methyl, the compound of formula I is an acid, the stereochemistry at $C_\alpha$ is R or S;

j) n is 2, m is 0, $R_1$ and $R_2$ are ethyl, the compound of formula I is an acid, the stereochemistry at $C_\alpha$ is R or S;

k) n is 2, m is 0, $R_1$ and $R_2$ are propyl, the compound of formula I is an acid, the stereochemistry at $C_\alpha$ is R or;

l) n is 2, in is 0, $R_1$ and $R_2$ are butyl, the compound of formula I is an acid, the stereochemistry at $C_\alpha$ is R or S.

Also preferred are the esters or salts of any of the foregoing preferred embodiments a-1.

Another aspect of the desamino, alkyl amino acid compounds of the invention is illustrated by Formula II given above. Preferred embodiments of Formula II include those wherein when n is 3, dashed line a is not present. Additional preferred embodiments include those wherein X is hydrogen, and wherein Y and $R_4$ are the same lower branched or straight chain alkyl. In yet another preferred embodiment, $R_4$ and $R_5$ are, independently, hydrogen or methyl. In another preferred embodiment, dashed line a is not present, X is hydrogen or lower branched or straight chain alkyl of $C_1$-$C_5$, preferably methyl or ethyl, and Y is hydrogen or lower branched or straight chain alkyl of $C_1$-$C_5$, preferably methyl, or dashed line a is present and z is 2, and preferably, n is 3. Additional preferred embodiments include those wherein R is methyl, ethyl, propyl or butyl and:

a) n is 3, dashed line a is not present, the compound of formula II is an acid, $R_4$ is hydrogen, X is hydrogen, Y is methyl, and the stereochemistry at $C_\alpha$ is R or S;

b) n is 3, dashed line a is not present, the compound of formula II is an acid, $R_4$ is methyl, X is hydrogen, Y is methyl, and the stereochemistry at $C_\alpha$ is R or S;

c) n is 3, dashed line a is present, the compound of formula II is an acid, z is 2, $R_4$ is hydrogen, and the stereochemistry at $C_\alpha$ is R or S;

d) n is 3, dashed line a is present, the compound of formula II is an acid, z is 2, $R_4$ is methyl, and the stereochemistry at $C_\alpha$ is R or S;

e) n is 3, dashed line a is not present, the compound of formula II is an acid, $R_4$ is hydrogen, X is methyl, Y is hydrogen, and the stereochemistry at $C_\alpha$ is R or S;

f) n is 3, dashed line a is not present, the compound of formula II is an acid, $R_4$ is hydrogen, X is ethyl, Y is hydrogen, and the stereochemistry at $C_\alpha$ is R or S;

g) n is 2, dashed line a is not present, the compound of formula II is an acid, $R_4$ is hydrogen, X is hydrogen, Y is methyl, and the stereochemistry at $C_\alpha$ is R or S;

h) n is 2, dashed line a is not present, the compound of formula II is an acid, $R_4$ is methyl, X is hydrogen, Y is propyl, and the stereochemistry at $C_\alpha$ is R or S;

i) n is 4, dashed line a is present, the compound of formula II is an acid, z is 2, $R_4$ is hydrogen, and the stereochemistry at $C_\alpha$ is R or S;

j) n is 3, dashed line a is present, the compound of formula II is an acid, z is 2, $R_4$ is methyl, and the stereochemistry at $C_\alpha$ is R or S;

k) n is 2, dashed line a is present, the compound of formula II is an acid, z is 3, $R_4$ is methyl, and the stereochemistry at $C_\alpha$ is R or S;

l) n is 3, dashed line a is not present, the compound of formula II is an acid, $R_4$ is methyl, X is hydrogen, Y is ethyl, and the stereochemistry at $C_\alpha$ is R or S.

Also preferred are the esters or salts of any of the forgoing preferred embodiments a-1.

A third aspect of the desamino, alkyl amino acid compounds of the invention is illustrated by Formula III. Preferred embodiments of Formula III include those wherein $R_6$ and $R_7$ are independently, hydrogen or lower alkyl or straight chain alkyl of $C_1$-$C_5$, preferably hydrogen or methyl, even more preferably all are hydrogen. In another embodiment, z is 2 or 3, preferably 3. In a preferred embodiment, n is 3. Additional preferred embodiments include those wherein R is methyl, ethyl, propyl or butyl and:

a) n is 3, z is 2, $R_6$ and $R_7$ are hydrogen, the compound of formula III is an acid, and the stereochemistry at $C_\alpha$ is R or S;

b) n is 3, z is 3, $R_6$ and $R_7$ are hydrogen, the compound of formula III is an acid, and the stereochemistry at $C_\alpha$ is R or S;

c) n is 2, z is 2, $R_6$ and $R_7$ are hydrogen, the compound of formula III is an acid, and the stereochemistry at $C_\alpha$ is R or S;

d) n is 4, z is 2, $R_6$ and $R_7$ are hydrogen, the compound of formula III is an acid, and the stereochemistry at $C_\alpha$ is R or S;

e) n is 2, z is 3, $R_6$ and $R_7$ are hydrogen, the compound of formula III is an acid, and the stereochemistry at $C_\alpha$ is R or S;

f) n is 4, z is 3, $R_6$ and $R_7$ are hydrogen, the compound of formula III is an acid, and the stereochemistry at $C_\alpha$ is R or S;

g) n is 2, z is 2, $R_6$ and $R_7$ are methyl, the compound of formula III is an acid, and the stereochemistry at $C_\alpha$ is R or S;

h) n is 4, z is 2, $R_6$ and $R_7$ are methyl, the compound of formula III is an acid, and the stereochemistry at $C_\alpha$ is R or S;

i) n is 2, z is 3, $R_6$ and $R_7$ are methyl, the compound of formula III is an acid, and the stereochemistry at $C_\alpha$ is R or S;

j) n is 4, z is 3, $R_6$ and $R_7$ are methyl, the compound of formula III is an acid, and the stereochemistry at $C_\alpha$ is R or S.

Also preferred are the esters or salts of the preferred foregoing embodiments a-j.

A fourth aspect of the invention is provided by the desamino, alkyl amino acid compounds of Formula IV. Preferred embodiments of the compounds of Formula IV include those wherein $R_9$, $R_{10}$, and $R_{11}$ are, independently, hydrogen or lower straight or branched chain alkyl of $C_1$-$C_5$, preferably hydrogen, methyl or ethyl. In another embodiment, $R_{10}$ is methyl. In yet another preferred embodiment, $R_9$ is hydrogen, $R_{10}$ is methyl, $R_{12}$ is hydrogen, and n is 3. Additional preferred embodiments include those wherein R is methyl, ethyl, propyl or butyl and:

a) n is 3, $R_9$ and $R_{11}$ are hydrogen, $R_{10}$ is methyl, the compound of formula IV is an acid, and the stereochemistry at $C_\alpha$ is R or S;

b) n is 3, $R_9$ is hydrogen, $R_{10}$ and $R_{11}$ are methyl, the compound of formula IV is an acid, and the stereochemistry at $C_\alpha$ is R or S;

c) n is 3, $R_9$ is hydrogen, $R_{10}$ is methyl, $R_{11}$ is ethyl, the compound of formula IV is an acid, and the stereochemistry at $C_\alpha$ is R or S;

d) n is 2, $R_9$ and $R_{11}$ are hydrogen, $R_{10}$ is methyl, the compound of formula IV is an acid, and the stereochemistry at $C_\alpha$ is R or S;

e) n is 2, $R_9$ is hydrogen, $R_{10}$ and $R_{11}$ are methyl, the compound of formula IV is an acid, and the stereochemistry at $C_\alpha$ is R or S;

f) n is 4, $R_9$ is are hydrogen, $R_{10}$ is methyl, $R_{11}$ is ethyl, the compound of formula IV is an acid, and the stereochemistry at $C_\alpha$ is R or S.

Also preferred are the esters or salts of the foregoing preferred embodiments a-f.

Figure 2:
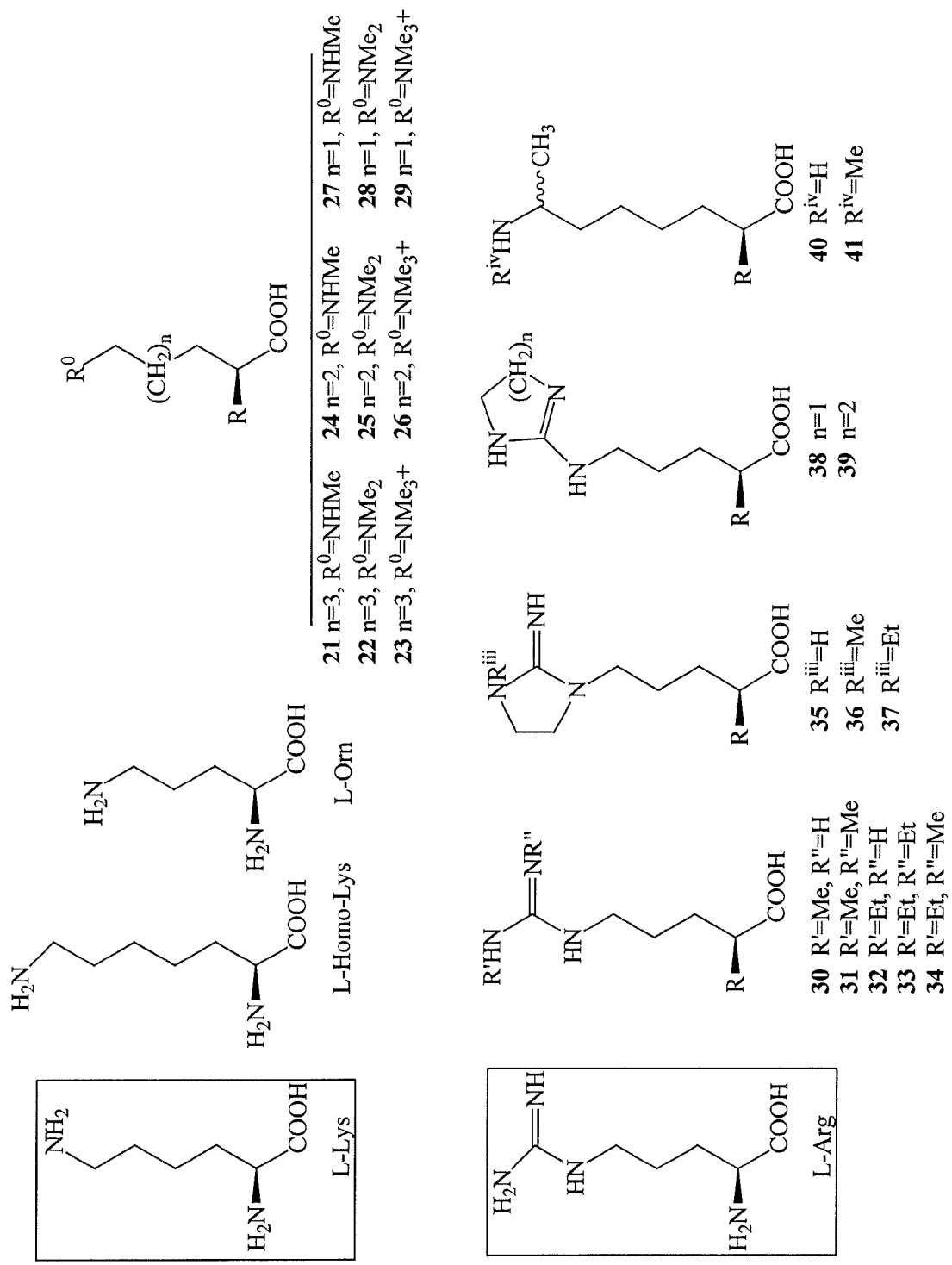
FIG. 2. Representative Examples of Compounds of Formulas I-IV.
Figure 3A:
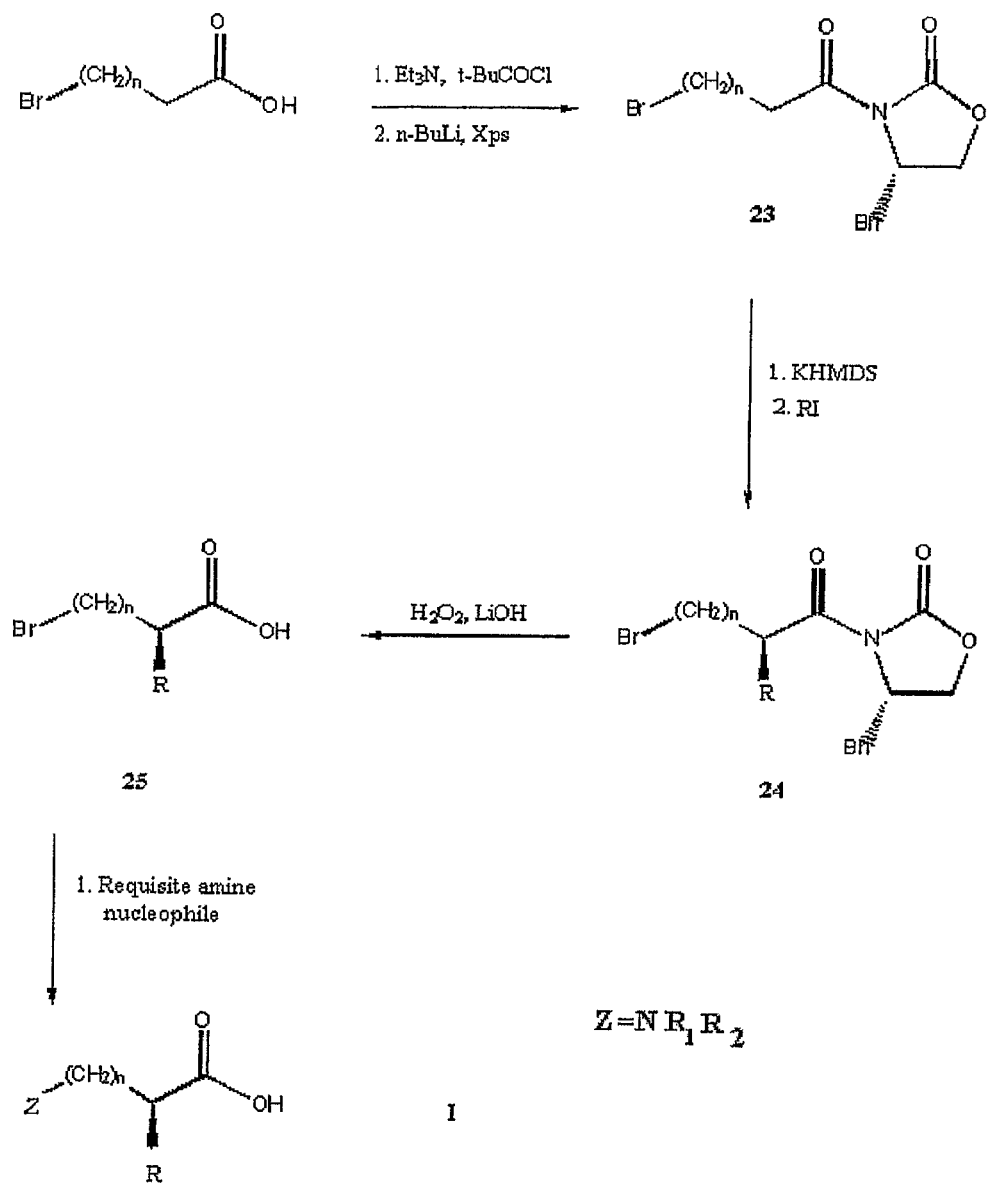
FIG. 3A-3C. Scheme for Synthesis of Compounds of Formulas I-IV.
Figure 3B:
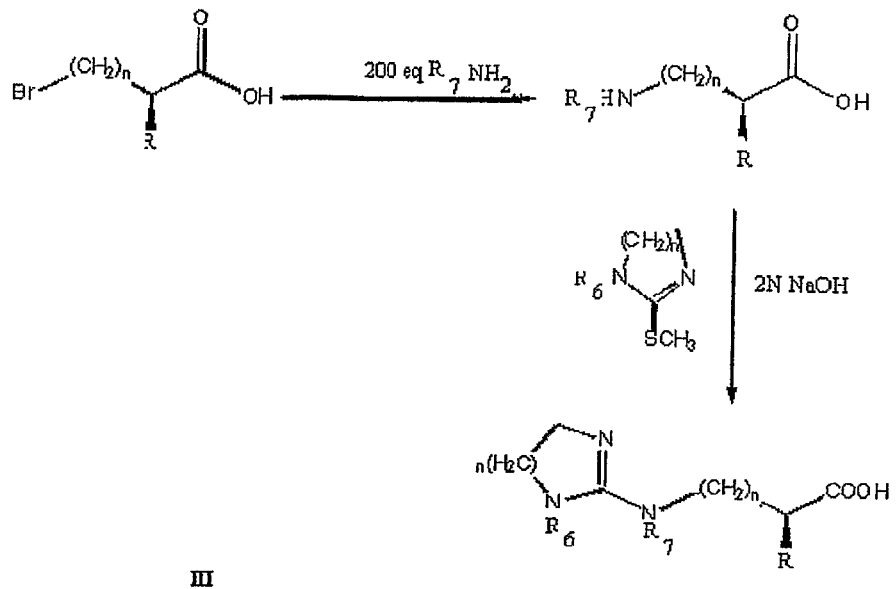
Figure 3B:
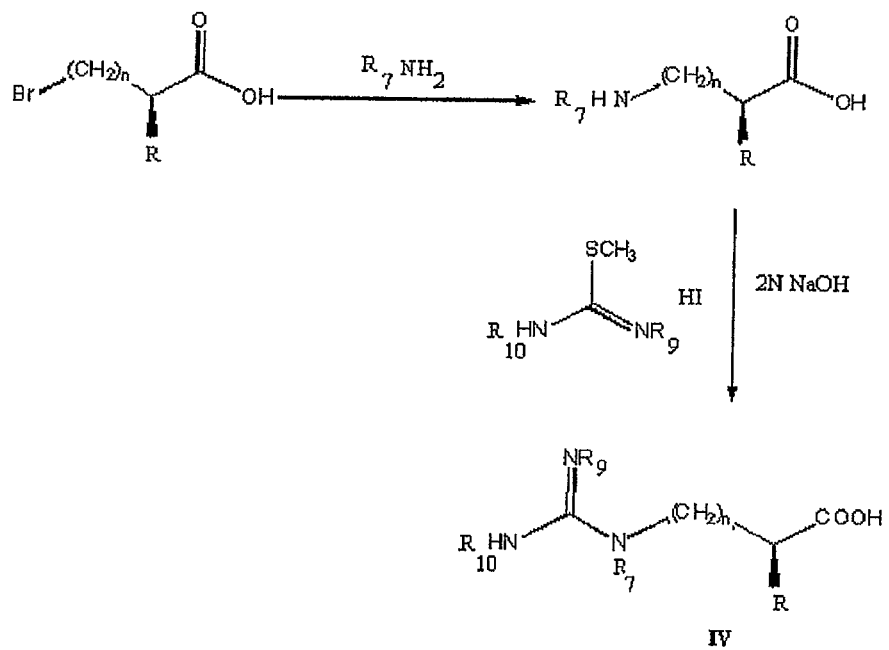
Figure 3C:
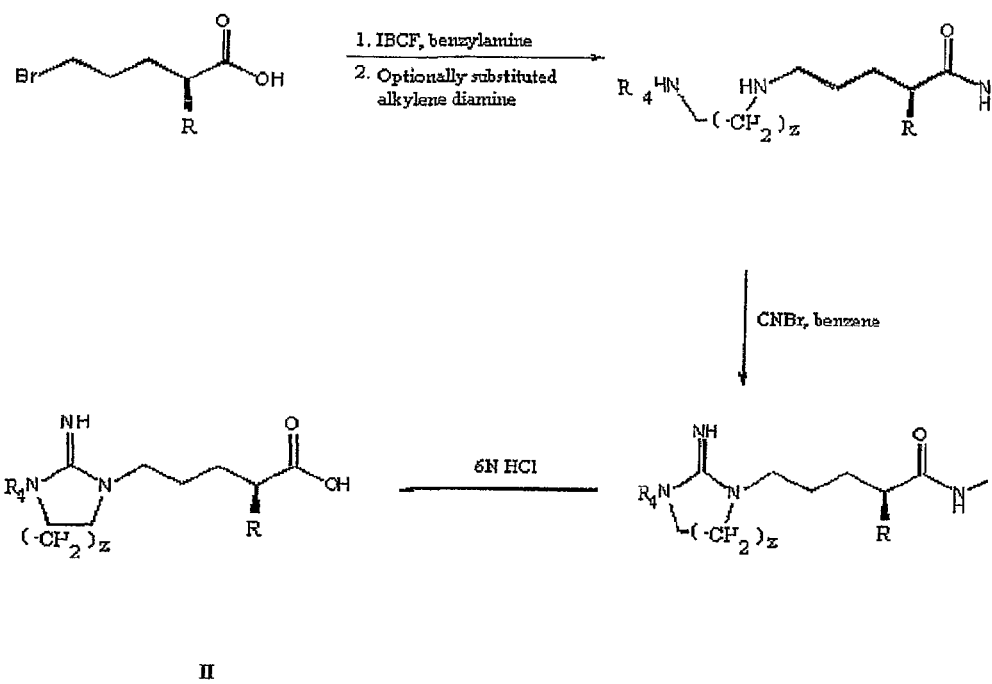

Especially preferred non-natural desamino, alkyl amino acid compounds of the invention include the formulas provided in FIG. 2 wherein R is methyl or ethyl.

Certain embodiments of the invention provide protected intermediates and protected non-natural amino acids of the invention. Certain embodiments provide protected intermediates and protected non-natural amino acids of the invention, wherein the side chain amine group is protected by a protecting group that prevents undesired reaction of the amino group and is removable by a chemical method that does not also cause amide group cleavage. Certain embodiments provide protected intermediates and protected non-natural amino acids of the invention, wherein the side chain carboxyl group is protected by a protecting group that prevents undesired reaction of the carboxyl group and is removable by a chemical method that does not also cause carboxyl group cleavage. In certain embodiments, the protecting group is t-butoxy carbonyl (BOC) or fluorenylmethoxycarbonyl (FMOC). In certain embodiments, the protecting group is BOC, FMOC, Alloc (allyloxycarbonyl), CBZ (benzyloxycarbonyl), Pbf (2,2,4,6,7-pentamethyldihydrobenzofuran-5-sulfonyl), NO2 (nitro), Pmc (2,2,5,7,8-pentamethylchroman-6-sulfonyl), Mtr (4-methoxy-2,3,6-trimethylbenzenesulfonyl), or Tos (tosyl).

In one embodiment, the structures of the non-natural desamino, alkyl amino acids of formulas I-IV are similar to those of the naturally occurring amino acids lysine, arginine as well as the naturally occurring glutamate biosynthesis intermediate, ornithine. In, preferred embodiments, the compounds of the invention differ from the corresponding natural amino acids due, inter alia, a longer or shorter methylene bridge between the (i) carboxyl terminus, which forms the N-terminus bond with the adjacent amino acid unit in a peptide, (ii) the presence of an alkyl group in place of the alpha amino group, and (iii) the organo group substitution of the amine side chain. Preferably, the extended bridge of the invention compared to the natural amino acid bridge is one carbon length longer or shorter (i.e., the homo- or des-forms). In other preferred embodiments, the compounds of the invention have, inter alia, longer, shorter, or equivalent methylene bridge lengths and have substitutions at various moieties, form different moieties, or link moieties to form ring structures, compared to the comparable natural amino acid.

Each of the compounds of the invention can be prepared as the acid, amide, salt or ester. In water, the non-natural amino acids of the present invention will be charged; however; in cell membranes and other non-polar regions of the cell, the non-natural amino acids may not be charged. In one embodiment, the ester group of the non-natural amino acids of the present invention is methyl, ethyl, t-butyl, benzyl or allyl. In another embodiment, the counter-ion for the salts of the non-natural amino acids is sodium, potassium, ammonium and tetra-alkyl ammonium.

Some embodiments of the invention provide semisynthetic peptides comprising a non-natural amino acid compound of the invention. In some embodiments, the semisynthetic peptide comprises a non-natural amino acid compound as its N-terminus moiety. In some embodiments, the semisynthetic peptide comprises a non-natural amino acid compound as the N-terminal moiety of a semisynthetic peptide of neurotensin (8-13). In one embodiment, the semisynthetic peptide is ABS201. In some embodiments, the semisynthetic peptide has an extended half-life in vivo as compared to a peptide having the same sequence as the semisynthetic peptide that does not comprise the non-natural amino acid compound substituted as its N-terminus moiety.

Certain embodiments of the present invention provide pharmaceutical compositions comprising a peptide of the invention and a pharmaceutical carrier. In certain embodiments, the peptide is present in unit dosage form.

Certain embodiments of the present invention provide cosmetic formulations comprising a non-natural amino acid compound of the invention and a cosmetic base formulation. Certain embodiments of the present invention provide cosmetic formulations comprising a semisynthetic peptide of the invention and a cosmetic base formulation. In certain embodiments, the cosmetic base formulation is an aqueous or oil base.

Certain embodiments of the present invention provide the non-natural amino acid compounds of the invention for use in medical therapy.

Certain embodiments of the present invention provide the use of the non-natural amino acid compounds of the invention for the manufacture of a medicament useful for treating psychosis in a mammal. Certain embodiments of the present invention provide the use of the semisynthetic peptides of the invention for the manufacture of a medicament useful for treating psychosis in a mammal. In certain embodiments, the psychosis is schizophrenia.

Certain embodiments of the present invention provide the use of a compound of the invention for the manufacture of a medicament useful for treating cancer in a mammal.

Certain embodiments of the present invention provide the use of a compound of the invention for the manufacture of a medicament useful for treating pain in a mammal.

Certain embodiments of the present invention provide the semisynthetic peptides of the invention for use in medical therapy.

Certain embodiments of the present invention provide a method to lower the body temperature of a patient, comprising administering to the patient an effective amount of a semisynthetic peptide of the invention so as to lower the body temperature of the patient.

Certain embodiments of the present invention provide a method to lower the body temperature of a patient, comprising administering to the patient an effective amount of a composition of the invention so as to lower the body temperature of the patient.

Certain embodiments of the present invention provide a method to treat a patient with psychosis, comprising administering to the patient an effective amount of a peptide of the invention so as to treat the psychosis.

Certain embodiments of the present invention provide a method to treat a patient with psychosis, comprising administering to the patient an effective amount of a composition of the invention so as to treat the psychosis.

Certain embodiments of the present invention provide a method to treat cancer, comprising administering to a patient an effective amount of a peptide of any of the invention so as to treat the cancer.

Certain embodiments of the present invention provide a method to treat cancer, comprising administering to a patient an effective amount of a composition of the invention so as to treat the cancer.

Certain embodiments of the present invention provide a method to treat pain, comprising administering to a patient an effective amount of a peptide of the invention so as to treat the pain.

Certain embodiments of the present invention provide a method to treat pain, comprising administering to a patient an effective amount of a composition of the invention so as to treat the pain.

Certain embodiments of the present invention provide a method for screening a peptide containing a non-natural amino acid compound for an activity, comprising the steps of: a) measuring a biological activity of a first peptide having a known amino acid sequence; and b) measuring the same biological activity of a semisynthetic peptide of any of the invention wherein the semisynthetic peptide has the same sequence as the first peptide except for the non-natural amino acid compound, or is a truncated version of the first peptide except for the non-natural amino acid compound. In certain embodiments of the invention, the biological activity is poptosis, apoptosis, cell signaling, ligand binding, transcription, translation, metabolism, cell growth, cell differentiation, homeostasis, half-life, solubility, or stability. In certain embodiments of the invention, the biological activity includes a direct or indirect assessment of the ability of the semisynthetic peptide to pass through a biological barrier. In certain embodiments of the invention, the biological activity is selectivity.

Certain embodiments of the present invention provide a method of treating a patient with a disease that is affected by administration to the patient of a known first peptide, comprising administering to the patient a semisynthetic peptide of the invention wherein the semisynthetic peptide has the same sequence as the first peptide except for the non-natural amino acid compound, or is a truncated version of the first peptide except for the non-natural amino acid compound.

Certain embodiments of the present invention provide a method of increasing the ability of a known first peptide to cross a biological barrier of a subject, comprising substituting a semisynthetic peptide of the invention wherein the semisynthetic peptide has the same sequence as the first peptide except for the non-natural amino acid compound, or is a truncated version of the first peptide except for the non-natural amino acid compound. In certain embodiments, the barrier comprises the blood brain barrier, a cell membrane, intestinal epithelium, skin, or blood-ocular.

Certain embodiments of the present invention provide a method of increasing the selectivity of a known peptide, comprising substituting for the known peptide a semisynthetic peptide of the invention wherein the semisynthetic peptide has the same sequence as the first peptide except for the non-natural amino acid compound, or is a truncated version of the first peptide except for the non-natural amino acid compound.

Certain embodiments of the present invention provide a method of increasing the resistance of a known peptide to digestion by a peptidase, comprising substituting for the known peptide a semisynthetic peptide of the invention wherein the semisynthetic peptide has the same sequence as the first peptide except for the non-natural amino acid compound, or is a truncated version of the first peptide except for the non-natural amino acid compound.

Certain embodiments of the present invention provide a method of treating a patient with a disease that is affected by administration to the patient of a known first peptide that crosses a body barrier, comprising administering to the patient a semisynthetic peptide of the invention wherein the semisynthetic peptide has the same sequence as the first peptide except for the non-natural amino acid compound, or is a truncated version of the first peptide except for the non-natural amino acid compound.

Certain embodiments of the present invention provide a method of treating a patient with a disease of the brain that is affected by administration to the patient of a known first peptide, comprising administering to the patient a semisynthetic peptide of any of the invention wherein the semisynthetic peptide has the same sequence as the first peptide except for the non-natural amino acid compound, or is a truncated version of the first peptide except for the non-natural amino acid compound.

Certain embodiments of the present invention provide a method for preparing a semisynthetic peptide with an extended half-life in vivo comprising substituting for a known peptide a semisynthetic peptide of the invention wherein the semisynthetic peptide has the same sequence as the first peptide except for the non-natural amino acid compound, or is a truncated version of the first peptide except for the non-natural amino acid compound.

The compound designators ABS201, ABS48, KH48, and peptide 28, as used herein, unless otherwise indicated, represent the same compound (SEQ ID NO:3).

Preparation of the Desamino, Alkyl Amino Acid Compounds

The preparation of the desamino, alkyl amino acid compounds of the invention follows the overall synthetic scheme depicted in FIG. 3. The first step in this process is the production of alpha alkyl, omega halogen carboxylic acids having a methylene unit chain length corresponding to n of formulas I through IV. In the following discussion, and in FIG. 3, this intermediate is designated as compound 27. Following the production of compound 27, its ω-halo group can be easily displaced with excess nucleophilic agent to produce the desamino, alkyl amino acid compounds of Formulas I-IV.

Typically, the reaction conditions for production of compound 27 involve protection of the carboxyl group of an omega carboxylic acid by formation of an acyl oxazolone. The acyl oxazolone is converted to an enolate and the enolate is combined with an alkylating agent such as alkyl iodide or alkyl mesylate to form compound 27. Use of a large excess of the alkylating agent and long reaction times promote significant yields of compound 27.

As shown in the synthetic scheme of FIG. 3, the alpha alkyl omega halo carboxylic acid compounds 25 can be converted to any of the side chain modifications by coupling the appropriate side chain moiety and the omega halo group of compound 25. Appropriate protection of the carboxyl group is also advantageously employed. The conditions for these reactions, and the appropriate alkylating and substituting agents follow the teaching set forth in "Advanced Organic Chemistry", 4$^{th}$ Edition, J. March, Wiley InterScience, New York, N.Y. 1992, the entire disclosure of which is incorporated herein by reference.

Figure 4:
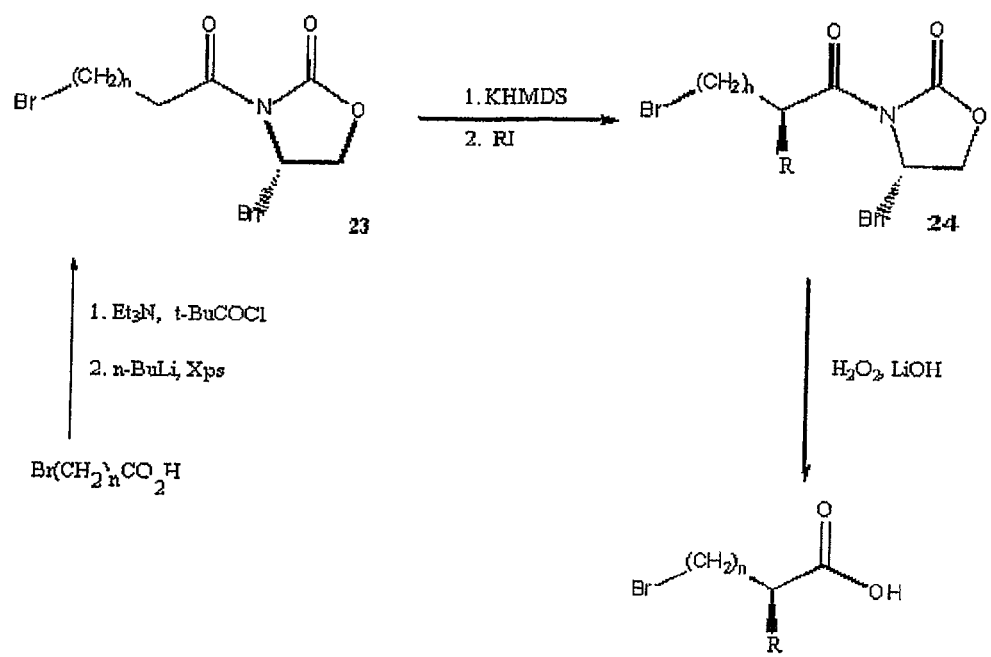
FIG. 4. Asymmetric synthesis of ω-bromo-2(S)-methyl acids.

In particular, to prepare the compounds of Formula I, (see synthetic schemes of FIGS. 3 and 4), the omega halo carboxylic acid compound 27 can be combined with the appropriate amine nucleophile such as ammonia, a primary amine or a secondary amine. The formulas of the amine nucleophiles correspond to the side chain moiety of Formula I. The reaction conditions will follow those appropriate for amine nucleophilic substitution as are disclosed in "Advanced Organic Chemistry" cited above and incorporated herein as if fully repeated. These compounds can be used directly in the following peptide synthesis provided that the side chain amine group is appropriately protected or otherwise inhibited from carboxyl condensation.

Figure 5:
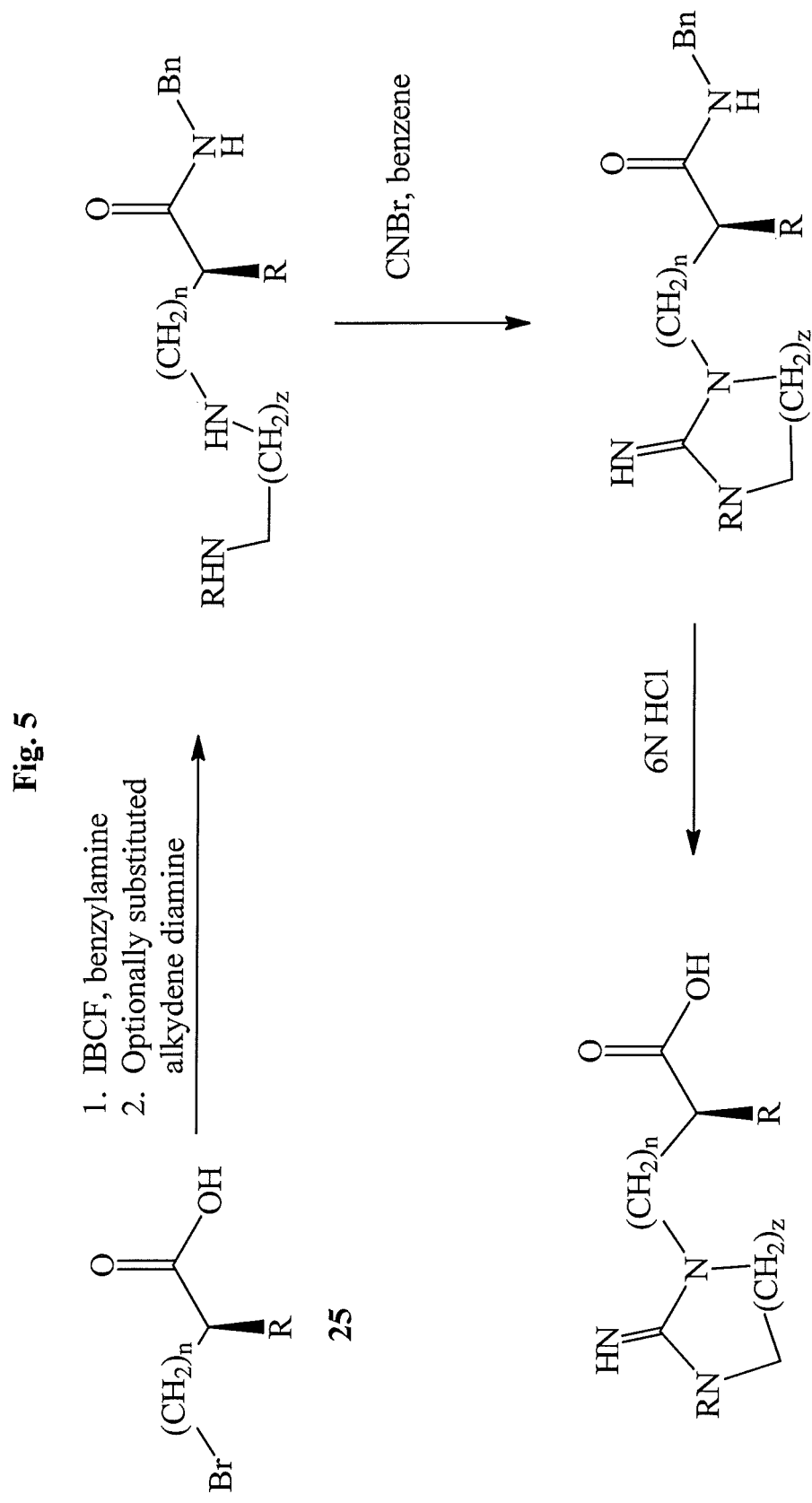
FIG. 5. Synthesis of ethylene-bridged ($N^\delta$ to $N^\omega$) arginine analogues.

Similarly, to prepare the compounds of Formula II (see the synthetic schemes of FIGS. 3 and 5) the omega halo compound 27 may first be protected at the carboxyl position and then can be reacted sequentially with a diamine and cyanogen bromide. Deprotection and purification will afford the desamino, alkyl amino acid compounds of Formula II. These compounds can be used directly in peptide synthesis with appropriate side chain protection.

Figure 6:
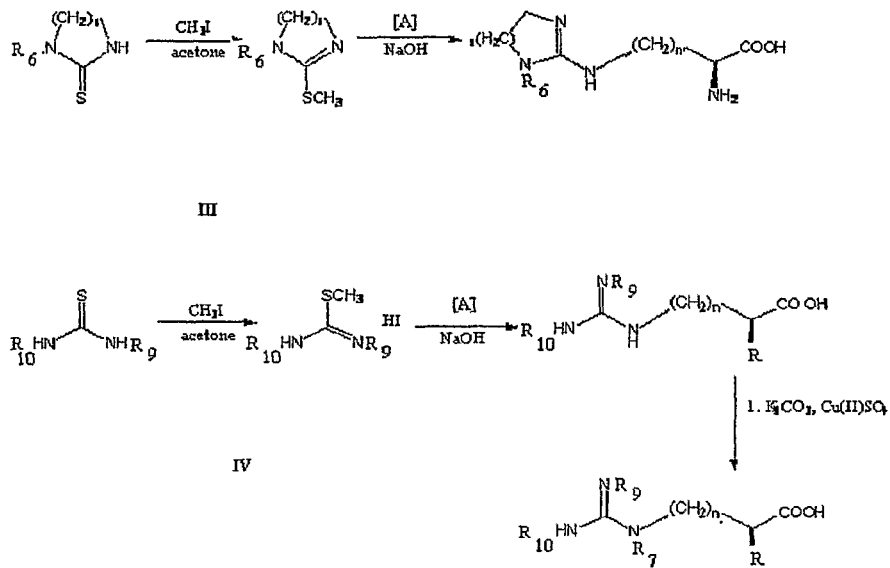
FIG. 6. Synthesis of cyclic and acyclic alkyl arginine analogues.
Figure 6:
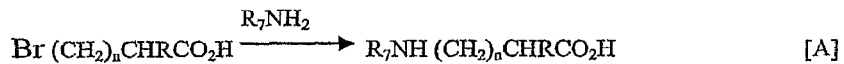

The compounds of Formulas III and IV (see the synthetic schemes of FIGS. 3 and 6) can also be prepared by addition of the side chain moiety to the omega halo carboxylic acid compounds 27. In this instance, protection of the carboxyl group is unnecessary. Preparation of the appropriate thiourea compound can be accomplished by addition of an alkylating agent such as an alkyl, alkenyl or alkynyl halide to thiourea, N-substituted thiourea or N,N-disubstituted thiourea (commercially available). The nucleophilic substitution of the resulting appropriate thiourea compound at the omega halo position of compound 27 under basic conditions provides the desamino, alkyl amino acid compounds of Formula IV. Similarly, addition of the appropriate cyclic thiourea compounds to the omega halo compound 27 under basic conditions provides the desamino, alkyl amino acid compounds of Formula III. The appropriate cyclic thiourea compounds can be prepared by combining an alkylating agent such as an alkyl, alkenyl or alkynyl halide with the corresponding unsubstituted, N-substituted or N,N-disubstituted cyclic diazathione (commercially available). The crude reaction products can be purified by known methods such as ion-exchange chromatography to yield the alkyl desamino amino acid compounds of Formulas III and IV which can be used directly in peptide synthesis with appropriate side chain protection.

Before their use in peptide synthesis, the side chains of the compounds of Formulas I-IV may either be appropriately protected or determined to be sufficiently hindered that they will not enter into a peptide condensation reaction. For example, if the side chain of the compounds of Formula I is a primary amine group, it may be appropriately protected according to the teaching of the art associated with peptide synthesis. See for example, the review of amine protecting groups provided in "Compendium of Organic Synthetic Methods," I&S Harrison, Wiley Interscience, New York, N.Y., 1971, the disclosure of which is incorporated herein by reference. In these instances, an appropriate protecting group can be t-butoxy carbonyl having the acronym BOC or fluorenylmethoxycarbonyl having the acronym FMOC. The BOC and FMOC protecting groups can be removed by mild treatment with acid, such as aqueous trifluoroacetic acid, and base, such as piperidine, respectively.

Alternatively, the omega halo carboxylic acid compound 27 can be coupled with the penultimate peptide to form an omega halo acyl moiety at the N-terminus of the penultimate peptide. Because the omega halo carboxylic acid compound 27 does not contain an amino moiety on its side chain, protection and spurious peptide formation are of less concern. In this alternative, the amino moiety can undergo nucleophilic reaction with the omega halo group of the acylated penultimate peptide as described above for formation of the compounds of Formulas I-IV. The desired peptide having a residue of a compound of Formula I-IV at its N-terminus is produced. In this alternative, appropriate protection of carboxyl and amino side chains and appropriate protection of the C-terminus may be employed to prevent undesirable reactions of these groups.

Peptide Synthesis and Purification

The invention includes the truncated and extended peptides which contain as their N-terminus moiety the residue of the compound of Formula I, II, III or IV. These peptides can be synthesized by the Merrifield solid phase method, which is an established method for preparing peptides to those skilled in the art. See R. B. Merrifield, *Science,* 232, 341-347 (1986), the disclosure of which is incorporated herein by reference for an explanation of, and conditions for the Merrifield solid phase peptide synthesis. Alternatively, the peptide minus the N-terminal amino acid unit, or penultimate peptide, can be expressed recombinantly by known biological methods and the desamino, alkyl amino acid compound of Formula I-IV can be added as the N-terminus by enzymatic condensation using an aminopeptidase. See "Enzyme Structure and Mechanism," Alan Fersht, W.H. Freeman, New York, N.Y. (1985), the disclosure of which is incorporated herein by reference, for an explanation of, and conditions for, recombinant expression of peptides. The Formulas I-IV compounds can be appropriately protected at the side chain amino group with standard protecting groups. In a preferred embodiment, the protecting groups are BOC and/or FMOC.

Briefly, for a solid phase synthesis, the penultimate peptide can be produced in bulk and then coupled to any of the Formula I-IV compounds using the protection and coupling techniques of the Merrifield solid phase synthesis. Starting with an appropriate anchor resin designed for amino group exposure, the carboxy terminus amino acid unit of the peptide having an amino protecting group such as an FMOC group is anchored to the resin through a selectively cleavable carboxyl coupling link. The amino group of the anchored carboxy terminus unit is then deprotected and the additional amino protected amino acid units are then sequentially coupled in proper sequence. Each coupling step will involve deprotection of the protected amino group of the anchored peptide chain followed by peptide condensation between that unprotected amino group and the carboxyl group of the next amino acid unit. The condensation can be facilely obtained by carbodiimide coupling, by Schotten Bauman reaction or by activated acyl group condensation. These condensation reactions are described in "Advanced Organic Chemistry", cited above. Protection of amine and carboxyl side chains using appropriate protecting groups that differ from the protecting groups of the alpha amino group entering into the peptide condensation will enable selective peptide condensation of the sequential amino acid units. Selection of appropriate protection groups and conditions for solid phase peptide synthesis are described in the Merrifield reference, cited above.

The penultimate peptides may also be produced by recombinant expression. This biological method involves re-engineering a microbe to express the penultimate peptide. A DNA segment encoding the penultimate peptide sequence can be inserted in proper reading from into a plasmid or other vector capable of causing microbial expression of the DNA. The vector will also contain appropriate control, promoter and selection DNA segments. Upon insertion into a microbe such as *E. coli* or *B. subtilus*, the microbe mixture can be selected for appropriate transfection by treatment with the corresponding selection agent. Typically the agent will be an antibiotic and the vector will contain a sequence encoding the corresponding detoxifying enzyme for the antibiotic. Chloramphenacol and penicillin are two of such agents. Culturing the transfected microbe and harvesting the expressed peptide as either secreted material of the culture medium or by lysing the microbe cells will provide the crude penultimate peptide. The penultimate peptide may be purified by known techniques such as lyophilization, chromatography and the like. These recombinant techniques for peptide expression are fully set forth in "Cold Spring Harbor—Current Protocols in Molecular Biology," Wiley Interscience, Cold Spring Harbor (2003), the disclosure of which is incorporated herein by reference.

An example of the solid phase peptide production is provided by the development of a set of neurotensin (8-13) compounds (NT peptide). These compounds incorporate the desamino, alkyl amino acid compounds of Formulas I-IV as their N-termini. They are a novel class of antipsychotic drugs, the biological study and background of which are described in the sections below.

NT Peptide Synthesis—General.

The penultimate sequence of the peptide, NT(9-13), can be synthesized in bulk using p-alkoxybenzyl alcohol solid phase methodology (65) and stored in the fully protected form.

Starting Materials.

P-alkoxybenzyl alcohol resin-bound Nα-Fmoc-leucine, Nα-Fmoc-isoleucine, Nα-Fmoc-tert-leucine, Nα-Fmoc-(But)-tyrosine, Nα-Fmoc-(Boc)-tryptophan, Nα-Fmoc-proline, and Nα-Fmoc-(Pbf)-arginine were purchased from Advanced Chemtech (Louisville, Ky.). PyBOP® was purchased from Novabiochem (San Diego, Calif.). N-hydroxybenzoriazole (HOBt), anhydrous N,N-dimethylformamide (DMF), N,N-diisopropylethylamine (DIPEA), triisopropylsilane (TIS), and trifluoroacetic acid (TFA) were purchased from Aldrich (Milwaukee, Wis.). Non-natural amino acid analogues were used as prepared. Abbreviations. Fmoc, fluorenylmethoxycarbonyl; $NH_3$, ammonia; $NH_2CH_3$, methylamine; $NH(CH_3)_2$, dimethylamine; $N(CH_3)_3$, trimethylamine; EtOH, ethanol.

Briefly, resin-bound Nα-Fmoc-leucine can be swelled in DMF prior to Fmoc cleavage with piperidine (20% in DMF). The piperidine solution can be removed with vacuum filtration and the resin-bound amino acid washed with DMF and $CH_2Cl_2$. Amino acids (4 eq) can be activated in DMF with HOBt (4 eq), PyBOP (4 eq), and DIPEA (10 eq) and added directly to the peptide reaction vessel. The amino acid couplings can be conducted for approximately 6 hr, the resin washed with DMF and $CH_2Cl_2$ and monitored with the Kaiser test (66) for the presence of free amines. Residues can be recoupled when necessary.

This procedure was repeated with subsequent amino acids to give the penultimate peptide sequence. Aliquots of the resin-bound pentamer can then be coupled as described above with the Formula I-IV compounds to give the desired peptides. Acid-catalyzed deprotection can be performed with a TFA solution containing appropriate scavengers and crude peptides can be precipitated in ice-cold ether.

Peptide Purification—General.

Reverse phase high pressure liquid chromatography can be used to purify the foregoing crude peptides. For example, a Waters dual pump system in combination with a Waters C18 radial compression column can be used for this purpose. Effluent can be monitored by UV absorbance at 280 nm.

Screening of Non-Natural Amino Acid-Containing Peptides

The invention provides a method for screening a peptide for an activity or pharmacological activity. The method includes the steps of: a) measuring an activity or pharmacological activity of a peptide having a selected natural amino acid sequence, and b) measuring the same activity or pharmacological activity of an extended or truncated peptide based upon the same amino acid sequence as the foregoing peptide wherein the N-terminus is a non-natural amino acid having the formula I-IV, described above; and c) comparing the measured activity or pharmacological activity of the peptides from steps a) and b) to determine whether the peptide of step b) has the desired activity or pharmacological activity.

The activities for which the present invention screens can include any activity associated with a biologically active peptide or peptidomimetic. The following is a partial list of the many activities that can be determined in the present screening method:

1. Receptor agonist/antagonist activity: A compendia of examples of specific screens for measuring these activities can be found in: "The RBI Handbook of Receptor Classification and Signal Transduction" K. J. Watling, J. W. Kebebian, J. L. Neumeyer, eds. Research Biochemicals International, Natick, Mass., 1995, and references therein. Methods of analysis can be found in: T. Kenakin "Pharmacologic Analysis of Drug-Receptor Interactions" $2^{nd}$ Ed. Raven Press, New York, 1993, and references therein.

2. Enzyme inhibition: A compendia of examples of specific screens for measuring these activities can be found in: H. Zollner "Handbook of Enzyme Inhibitors", $2^{nd}$ Ed. VCH Weinheim, FRG, 1989, and references therein.

3. Central nervous system, autonomic nervous system (cardiovascular and gastrointestinal tract), antihistaminic, antiinflammatory, anaesthetic, cytotoxic, and antifertility activities: A compendia of examples of specific screens for measuring these activities can be found in: E. B. Thompson, "Drug Bioscreening: Drug Evaluation Techniques in Pharmacology", VCH Publishers, New York, 1990, and references therein.

4. Anticancer activities: A compendia of examples of specific screens for measuring these activities can be found in: I. J. Fidler and R. J. White "Design of Models for Testing Cancer Therapeutic Agents", Van Nostrand Reinhold Company, New York, 1982, and references therein.

5. Antibiotic and antiviral (especially anti-HIV) activities: A compendia of examples of specific screens for measuring these activities can be found in: "antibiotics in Laboratory Medicine", $3^{rd}$ Ed., V. Lorian, ed. Williams and Wilkens, Baltimore, 1991, and references therein. A compendia of anti-HIV screens for measuring these activities can be found in: "HIV Volume 2: Biochemistry, Molecular Biology and Drug Discovery", J. Karn, ed., IRL Press, Oxford, 1995, and references therein.

6. Immunomodulatory activity: A compendia of examples of specific screens for measuring these activities can be found in: V. St. Georgiev (1990) "Immunomodulatory Activity of Small Peptides" Trends Pharm. Sci. 11, 373-378.

7. Pharmacokinetic properties: The pharmacological activities assayed in the screening method include half-life, solubility, or stability, among others. For example, methods of analysis and measurement of pharmacokinetic properties can be found in: J.-P. Labaune "Handbook of Pharmacokinetics: Toxicity Assessment of Chemicals", Ellis Horwood Ltd., Chichester, 1989, and references therein.

In the screening method, the peptide of step a) can consist of natural amino acids. Alternatively, the peptide of step a) can contain mostly natural amino acids, but also contain one or a small number of non-natural amino acids. Such a peptide is considered to consist essentially of natural amino acids.

In the screening method, the peptide of step b) will be the truncated or extended peptide of the invention as described above. In one embodiment, the structures of the non-natural amino acids of formulas I-IV will be similar to those of the naturally occurring amino acids, lysine and arginine.

Thus, in the screening method contemplated herein, any extended or truncated peptide can be compared to any peptide having the same downstream sequence and having a known activity or pharmacological activity to determine whether or not the extended or truncated peptide has the same or similar activity or pharmacological activity at the same or different level. Depending on the specifics of how the measuring step is carried out, the present screening method can also be used to detect an activity or pharmacological activity exhibited by the extended or truncated peptide. Also, the screening method can be used to detect and measure qualitative and quantitative differences in the same or similar activity or pharmacological activity.

Thus, the methods of the present invention provide evaluation of the alteration of activity of the extended or truncated peptide. Typically, the hydrophobicity of the peptide is increased, which can result indirectly in increased binding activity when the desamino alkyl amino acid moiety is involved in binding (e.g., receptor-ligand binding, enzyme-cofactor binding, enzyme-substrate binding) and since binding strength is correlated with activity, a peptide higher potency (higher measured activity level) can result.

Furthermore, the desamino alkyl amino acids of the present invention also can enhance or increase the pharmacological activity of a peptide. For example, because the desamino alkyl amino acids are more hydrophobic (i.e., more lipophilic), a peptide containing a non-natural amino acid is more able to pass a body barrier (e.g., blood brain, blood ocular, skin, intestinal epithelium). Additionally, because the desamino alkyl amino acids impart increased selectivity and stability to a peptide, the pharmacological activity can also be screened when compared to other peptides.

Treatment

The invention further relates to a method of treating or preventing in a subject a malcondition comprising administering to the subject an extended or truncated peptide having as its N-terminus an amino acid having the formula I-IV. The basis peptide from which the extended or truncated peptide is formed will have or will be believed to have a biochemical, physiological, pharmacological or biological relationship with the malcondition to be treated or prevented. The malcondition may be a disease, biological or organic disfunction or an undesirable biological condition that is not ordinarily regarded as a disease or disfunction, such as but not limited to cosmetic malconditions such as skin blotches, acne, and the like. The subject may be a medical or veterinary patient including mammals such as humans, and non-humans mammals such as dogs, cats, cows, sheep, pigs as well as avian.

In the method of the present invention, the malconditions that can be treated or prevented and the peptides that can be used are numerous. A partial list of peptides and malconditions is set out below.

Peptides for triggering B and T cell activity can be used to treat autoimmune disease, including uveitis, collagen-induced, adjuvant and rheumatoid arthritis, thyroiditis, myasthenia gravis, multiple sclerosis and diabetes. Examples of these peptides are interleukins (referenced in Aulitzky, W E; Schuler, M; Peschel, C.; Huber, C.; Interleukins. Clinical pharmacology and therapeutic use. Drugs. 48(5):667-77, 1994 November) and cytokines (referenced in Peters, M.; Actions of cytokines on the immune response and viral interactions: an overview. Hepatology. 23(4):909-16, 1996 April).

Enkephlin and analogs, agonists and antagonists can be used to treat AIDS, ARC, and cancer, pain modulation, Huntington's, Parkinson's diseases.

LHRH and analogs, agonists and antagonists can be used to treat prostatic tumors and reproductive physiopathology, including breast cancer, and infertility.

Peptides and peptidomimetics that target crucial enzymes, oncogenes or oncogene products, tumor-suppressor genes and their products, growth factors and their corresponding receptors can be used to treat cancer. Examples of these peptides are described in Unger, C. Current concepts of treatment in medical oncology: new anticancer drugs. Journal of Cancer Research & Clinical Oncology. 122(4):189-98, 1996.

Neuropeptide Y and other pancreatic polypeptides, and analogs, agonists and antagonists can be used to treat stress, anxiety, depression and associated vasoconstrictive activities.

Gluco-incretins, including gastric inhibitory polypeptide, glucose-dependent insulinotropic polypeptide, PACAP/Glucagon and glucagon-like polypeptide-1 and 2 and analogs, agonists and antagonists can be used to treat Type II diabetic hyperglycaemia.

Atrial natriuretic factor and analogs, agonists and antagonists can be used to treat congestive heart failure.

Integrin and analogs, agonists and antagonists can be used to treat osteoporosis, scar formation, bone synthesis, inhibition of vascular occlusion, and inhibition of tumor invasion and metastasis.

Glucagon, glucagon-like peptide 1, PACAP/Glucagon, and analogs, agonists and antagonists can be used to treat diabetes cardiovascular emergencies.

Antithrombotic peptides and analogs, agonists and antagonists can be used to treat cardiovascular and cerebrovascular diseases. Examples of these peptides RGD, D-Phe-Pro-Arg and others named are described in Ojima I.; Chakravarty S.; Dong Q. Antithrombotic agents: from RGD to peptide mimetics. Bioorganic & Medicinal Chemistry. 3(4):337-60, 1995.

Cytokines/interleukins and analogs, agonists and antagonists can be used to treat inflammatory disease, immune response dysfunction, hematopoiesis, mycosis fungoides, aplastic anemia, thrombocytopenia, and malignant melanoma. Examples of these peptides are Interleukins, referenced in Aulitzky et al. and Peters et al.

Endothelin and analogs, agonists and antagonists can be used to treat arterial hypertension, myocardial infarction, congestive heart failure, atherosclerosis, shock conditions, renal failure, asthma and vasospasm Natriuretic hormones and analogs, agonists and antagonists can be used to treat cardiovasicular disease and acute renal failure. Examples of these peptides are named and described in Espiner, E. A;. Richards, A. M.; Yandle, T. G.; Nicholls, M. G.; Natriuretic hormones. Endocrinology & Metabolism Clinics of North America. 24(3):481-509, 1995.

Peptides that activate or inhibit tyrosine kinase, or bind to TK-activating or inhibiting peptides and analogs, agonists and antagonists can be used to treat chronic myelogenous and acute lymphocytic leukemias, breast and ovarian cancers and other tyrosine kinase associated diseases. Examples of these peptides are described in Smithgall, T E.; SH2 and SH3 domains: potential targets for anti-cancer drug design. Journal of Pharmacological & Toxicological Methods. 34(3):125-32, 1995.

Renin inhibitors analogs, agonists and antagonists can be used to treat cardiovascular disease, including hypertension and congestive heart failure. Examples of these peptides are described in Rosenberg, S. H.; Renin inhibition. Cardiovascular Drugs & Therapy. 9(5):645-55, 1995.

Angiotensin-converting enzyme inhibitors, analogs, agonists and antagonists can be used to treat cardiovascular disease, including hypertension and congestive heart failure.

Peptides that activate or inhibit tyrosine phosphorylases can be used to treat cardiovascular diseases. Examples of these peptides are described in Srivastava, A. K.; Protein tyrosine phosphorylation in cardiovascular system. Molecular & Cellular Biochemistry. 149-150:87-94, 1995.

Peptide based antivirals can be used to treat viral diseases. Examples of these peptides are described in Toes, R. E.; Feltkamp, M. C.; Ressing, M. E.; Vierboom, M. P.; Blom, R. J.; Brandt, R. M; Hartman, M.; Offringa, R.; Melief, C. J.; Kast, W. M.; Cellular immunity against DNA tumour viruses: possibilities for peptide-based vaccines and immune escape. Biochemical Society Transactions. 23(3):692-6, 1995.

Corticotropin releasing factor and peptide analogs, agonists and antagonists can be used to treat disease associated with high CRF, i.e Alzheimer's disease, anorexia nervosa, depressive disorders, arthritis, and multiple sclerosis.

Peptide agonists and antagonists of platelet-derived wound-healing formula (PDWHF) can be used as a therapy for donor tissue limitations and wound-healing constraints in surgery. Examples of these peptides are described in Rudkin, G. H.; Miller, T. A.; Growth factors in surgery. Plastic & Reconstructive Surgery. 97(2):469-76, 1996.

Fibronectin, fibrinopeptide inhibitors and analogs, agonists and antagonists can be used to treat metastasis (i.e. enzyme inhibition, tumor cell migration, invasion, and metastasis).

Chemokine (types of cytokine, including interleukin-8, RANTES, and monocyte chemotactic peptide) analogs, agonists and antagonists can be used to treat arthritis, hypersensitivity, angiogenesis, renal disease, glomerulonephritis, inflammation, and hematopoiesis.

Neutral endopeptidase inhibitors and analogs, agonists and antagonists can be used to treat hypertension and inflammation. Examples of these peptides are described in Gregoire, J. R; Sheps, S. G; Newer antihypertensive drugs. Current Opinion in Cardiology. 10(5):445-9, 1995.

Substance P and analogs, agonists and antagonists can be used to treat immune system dysfunction, pain transmission/perception and in autonomic reflexes and behaviors.

Alpha-melanocyte-stimulating hormone and analogs, agonists and antagonists can be used to treat AIDS, rheumatoid arthritis, and myocardial infarction.

Bradykinin (BK) and analogs, agonists and antagonists can be used to treat inflammatory diseases (edema, etc), asthma, allergic reactions (rhinitis, etc), anesthetic uses, and septic shock.

Secretin can be used to treat cardiovascular emergencies.

GnRH and analogs, agonists and antagonists can be used to treat hormone-dependent breast and prostate tumors.

Somatostatin and analogs, agonists and antagonists can be used to treat gut neuroendocrine tumors.

Gastrin, Gastrin Releasing Peptide and analogs, agonists and antagonists can be used as an adjuvant to chemotherapy or surgery in small cell lung cancer and other malignancies, or to treat allergic respiratory diseases, asthma and allergic rhinitis.

Laminin, the Laminin derivative antimetastatic drug YIGSR peptide, Laminin-derived synthetic peptides analogs, agonists and antagonists can be used to treat tumor cell growth, angiogenesis, regeneration studies, vascularization of the eye with diabetes, and ischemia. The peptides of this category can inhibit the tumor growth and metastasis of leukemic cells and may be useful as a potential therapeutic reagent for leukaemic infiltrations. Peptides containing this sequence also inhibit experimental metastasis. Exemplary references include McGowan K A. Marinkovich M P. Laminins and human disease. Microscopy Research & Technique. 51(3):262-79, 2000 Nov. 1; Yoshida N. Ishii E. Nomizu M. Yamada Y. Mohri S. Kinukawa N. Matsuzaki A. Oshima K. Hara T. Miyazaki S. The laminin-derived peptide YIGSR (Tyr-Ile-Gly-Ser-Arg) inhibits human pre-B leukaemic cell growth and dissemination to organs in SCID mice. British Journal of Cancer. 80(12):1898-904, 1999. Examples of these peptides are also described in Kleinman, H. K.; Weeks, B. S.; Schnaper, H. W.; Kibbey, M. C.; Yamamura, K.; Grant, D. S; The laminins: a family of basement membrane glycoproteins important in cell differentiation and tumor metastases. Vitamins & Hormones. 47:161-86, 1993.

Defensins, corticostatins, dermaseptins, mangainins, and other antibiotic (antibacterial and antimicrobial) peptides and analogs, agonists and antagonists can be used to treat infections, tissue inflammation and endocrine regulation.

Vasopressin and analogs, agonists and antagonists can be used to treat neurological disorders, stress and Diabetes insipidus.

Oxytocin and analogs, agonists and antagonists can be used to treat neurological disorders and to induce labor.

ACTH-related peptides and analogs, agonists and antagonists can be used as neurotrophic, neuroprotective, and peripheral demyelinating neuropathy agents.

Amyloid-beta peptide and analogs, agonists and antagonists can be used to treat Alzheimer's disease.

Epidermal growth factor, receptor, and analogs, agonists and antagonists can be used to treat necrotizing enterocolitis, Zollinger-Ellison syndrome, gastrointestinal ulceration, colitis, and congenital microvillus atrophycarcinomas.

Leukocyte adhesion molecules and their ligands, and analogs, agonists and antagonists can be used to treat atherosclerosis, inflammation. Examples of these peptides are described in Barker, J. N.; Adhesion molecules in cutaneous inflammation. Ciba Foundation Symposium. 189:91-101.

Major histocompatibility complex (MHC) binding peptides and analogs, agonists and antagonists can be used to treat autoimmune, immunodysfunctional, immuno modulatory diseases and as well as used for their corresponding therapies. Examples of these peptides are described in Appella, E.; Padlan, E. A.; Hunt, D. F; Analysis of the structure of naturally processed peptides bound by class I and class II major histocompatibility complex molecules. EXS. 73:105-19, 1995.

Corticotropin releasing factor can be used to treat neurological disorders.

Neurotrophins (including brain-derived neurotrophic factor (BDNF), nerve growth factor, and neurotrophin 3) and analogs, agonists and antagonists can be used to treat neurological disorders.

Cytotoxic T-cell activating peptides can be used to treat infectious diseases and cancer. Examples of these peptides are described in: Chesnut R. W.; Sette, A.; Celis, E.; Wentworth, P.; Kubo, R. T.; Alexander, J.; Ishioka, G.; Vitiello, A.; Grey, H. M; Design and testing of peptide-based cytotoxic T-cell-mediated immunotherapeutics to treat infectious diseases and cancer. Pharmaceutical Biotechnology. 6:847-74, 1995.

Peptide immunogens for prevention of HIV-1 and HTLV-I retroviral infections can be used to treat AIDS. Examples of these peptides are described in Hart, M. K.; Palker, T. J.; Haynes, B F; Design of experimental synthetic peptide immunogens for prevention of HIV-1 and HTLV-I retroviral infections. Pharmaceutical Biotechnology. 6:821-45, 1995.

Galanin and analogs, agonists and antagonists can be used to treat Alzheimer's disease, depression, eating disorders, chronic pain, prevention of ischemic damage, and growth hormone modulation.

Tachykinins (neurokinin A and neurokinin B) and analogs, agonists and antagonists can be used to treat pain transmission/perception and in autonomic reflexes and behaviors.

RGD containing peptides can be used to treat various diseases involved with cell adhesion, antithrombotics, and acute renal failure.

Osteogenic growth peptide and analogs, agonists and antagonists can be used as treatment of systemic bone loss. Examples of these peptides are described in Bab IA. Regulatory role of osteogenic growth peptide in proliferation, osteogenesis, and hemopoiesis. Clinical Orthopaedics & Related Research. (313):64-8, 1995.

Parathyroid hormone, parathyroid hormone related-peptide and analogs, agonists and antagonists can be used to treat diseases affecting calcium homeostasis (hypercalcemia), bone metabolism, vascular disease, and atherosclerosis.

Kallidin and analogs, agonists and antagonists can be used to treat tissue injury or inflammation and pain signaling pathological conditions of the CNS.

T cell receptor peptide vaccines and analogs, agonists and antagonists can be used in immunotherapy. Examples of these peptides are described in Brostoff, S W; T cell receptor peptide vaccines as immunotherapy. Agents & Actions—Supplements. 47:53-8, 1995.

Platelet-derived growth factor (PDGF) and analogs, agonists and antagonists can be used to treat non-neoplastic hyperproliferative disorders, therapy for donor tissue limitations and wound-healing constraints in surgery.

Amylin, calcitonin gene related peptides (CGRP) and analogs, agonists and antagonists can be used to treat insulin-dependent diabetes.

Vasoactive intestinal polypeptide and analogs, agonists and antagonists can be used to treat allergic respiratory diseases, asthma and allergic rhinitis, and nervous control of reproductive functions.

Growth hormone-releasing hormone and analogs, agonists and antagonists can be used to treat growth hormone deficiency and immunomodulation.

HIV protease inhibiting peptides can be used to treat AIDS. Examples of these peptides are described in Bugelski, P. J.; Kirsh, R.; Hart, T. K; HIV protease inhibitors: effects on viral maturation and physiologic function in macrophages. Journal of Leukocyte Biology. 56(3):374-80, 1994.

Thymopoietin active fragment peptides and analogs, agonists and antagonists can be used to treat rheumatoid arthritis and virus infections.

Cecropins and analogs, agonists and antagonists can be used as antibacterials.

Thyroid releasing hormone and analogs, agonists and antagonists can be used to treat spinal cord injury and shock.

Erythropoietin and analogs, agonists and antagonists can be used to treat anemia.

Fibroblast growth factor (FGF), receptor and analogs, agonists and antagonists can be as stimulation of bone formation, as well as used as a treatment for Kaposi's sarcoma, neuron regeneration, prostate growth, tumor growth inhibition, and angiogenesis.

Stem cell factor and analogs, agonists and antagonists can be used to treat anemias.

GP120, GP160, CD4 fragment peptides and analogs, agonists and antagonists can be used to treat AIDS.

Insulin-like growth factor, receptor, and analogs, agonists and antagonists can be used to treat breast and other cancers, noninsulin-dependen diabetest mellitus, cell proliferation, apoptosis, hematopoiesis, AIDS, growth disorders, osteoporosis, and insulin resistance.

Colony stimulating factors (granulocyte-macrophage colony-stimulating factor, granulocyte colony-stimulating factor, and macrophage colony-stimulating factor and analogs, agonists and antagonists can be used to treat anemias.

Kentsin and analogs, agonists and antagonists can be used for immunomodulation.

Lymphocyte activating peptide and analogs, agonists and antagonists can be used for immunomodulation. Examples of these peptides are described in Loleit, M.; Deres, K.; Wiesmuller, K. H.; Jung, G.; Eckert, M.; Bessler, W. G; Biological activity of the *Escherichia coli* lipoprotein: detection of novel lymphocyte activating peptide segments of the molecule and their conformational characterization. Biological Chemistry Hoppe-Seyler. 375(6):407-12, 1994 June.

Tuftsin and analogs, agonists and antagonists can be used for immunomodulation.

Prolactin and analogs, agonists and antagonists can be used to treat rheumatic diseases, systemic lupus erythematosus, and hyperprolactemia.

Angiotensin II and receptor(s) and analogs, agonists and antagonists can be used to treat hypertension, hemodynamic regulation, neurological disorders, diabetic nephropathies, aortoarterities induced RVH, hyperaldosteronism, heavy metal induced cardiovascular effects, diabetes mellitus and thyroid dysfunction.

Dynorphin and analogs, agonists and antagonists can be used to treat neurological disorders, pain management, algesia, spinal cord injury and epilepsy.

Calcitonin, and analogs, agonists and antagonists can be used to treat neurological disorders, immune system dysfunction, calcium homeostasis, and osteoporosis.

Pituitary adenylate cyclase activating polypeptide can play a role in growth, signal transduction vasoactivity roles, exact role in diseases not determined yet.

Cholecystokinin and analogs, agonists and antagonists can be used to treat feeding disorders, panic disorders, and anti-opioid properties.

Pepstatin and analogs, agonists and antagonists can be used as pepsin and HIV protease inhibitors (AIDS).

Bestatin and analogs, agonists and antagonists can be used to treat muscular dystrophy, anticancer, antileukemia, immune response modulator, and acute non-lymphocytic leukemia.

Leupeptin and analogs, agonists and antagonists can be used as a protease inhibitor, exact role in diseases not determined yet.

Luteinizing hormone and releasing hormone and analogs, agonists and antagonists can be used as a infertility male contraceptive.

Neurotensin and analogs, agonists and antagonists can be used, e.g., as antipsychotic, analgesic, anti-cancer, and/or neuroprotective agents, e.g., for treating stroke victims, e.g., by inducing hypothermia so as to provide neuroprotection.

Motilin and analogs, agonists and antagonists can be used for the control of gastric emptying.

Insulin and analogs, agonists and antagonists can be used to treat diabetes.

Transforming growth factor (TGF) and analogs, agonists and antagonists can be used for cell proliferation and differentiation, cancer treatment, immunoregulation, therapy for donor tissue limitations, and wound-healing constraints in surgery.

Bone morphogenetic proteins (BMPs) and analogs, agonists and antagonists can be used as therapy for donor tissue limitations, osteogenesis, and wound-healing constraints in surgery.

Bombesin and Enterostatin as well as their analogs, agonists and antagonists can be used to prevent the proliferation of tumor cells, modulation of feeding, and neuroendocrine functions. These peptides fall within a supercategory of the neuromedins described above. These peptides are described in such exemplary references as Yamada K. Wada E. Wada K. Bombesin-like peptides: studies on food intake and social behaviour with receptor knock-out mice. Annals of Medicine. 32(8):519-29, 2000 November; Ohki-Hamazaki H. Neuromedin B. Progress in Neurobiology. 62(3):297-312, 2000 October; Still CD. Future trends in weight management. Journal of the American Osteopathic Association. 99(10 Su Pt 2):S18-9, 1999; Martinez V. Tache Y. Bombesin and the brain-gut axis. Peptides. 21(11):1617-25, 2000; Afferent signals regulating food intake. Proceedings of the Nutrition Society. 59(3):373-84, 2000; Takenaka Y. Nakamura F. Jinsmaa Y. Lipkowski A W. Yoshikawa M. Enterostatin (VPDPR) has anti-analgesic and anti-amnesic activities. Bioscience Biotechnology & Biochemistry. 65(1):236-8, 2001 J.

Glucagon, glucagon-like peptide 1 and analogs, agonists and antagonists can be used to treat diabetes cardiovascular emergencies.

Pancreastatin, chromogranins A, B and C and analogs, agonists and antagonists—conditions associated with inhibition of insulin secretion, exocrine pancreatic secretion and gastric acid secretion, and stimulation of egradati secretion.

Endorphins and analogs, agonists and antagonists can be used to treat neurological disorders, alleviating pain, treatment of opioid abuse, obesity, and diabetes. Examples of these peptides are named and described in Dalayeun, J. F.; Nores, J. M.; Bergal, S.; Physiology of beta-endorphins. A close-up view and a review of the literature. Biomedicine & Pharmacotherapy. 47(8):311-20, 1993.

Miscellaneous opioid peptides, including (but not limited to) adrenal peptide E, alpha casein fragment, beta casomorphin, dermorphin, kyotorphin, metophamide neuropeptide FF (NPFF), melanocyte inhibiting factor, and analogues, agonists and antagonists can be used to treat neurological disorders, alleviating pain, as well as for the treatment of opioid abuse.

Vasotocin and analogues, agonists and antagonists can be used for clinical uses to be determined.

Protein kinase C and inhibitors and analogues, agonists and antagonists can be used to treat cancer, apoptosis, smooth muscle function, and Alzheimer's disease. Examples of these peptides are named and described in Philip, P. A.; Harris, A. L; Potential for protein kinase C inhibitors in cancer therapy. Cancer Treatment & Research. 78:3-27, 1995.

Amyloid, amyloid fibrin, fragments and analogues, agonists and antagonists can be used to treat neurodegenerative diseases and diabetes.

Calpain and other calmodulin-inhibitory proteins and analogues, agonists and antagonists can be used to treat neurodegenerative disorders, cerebral ischaemia, cataracts, myocardial ischaemia, muscular dystrophy and platelet aggregation.

Charybdotoxin, Apamin and analogues, agonists and antagonists can be used for treatment of neurodegenerative diseases and pain and cerebral ischemia.

Phospholipase A2 and receptor inhibiting/activating peptides and analogues, agonists and antagonists can be used to treat acute pancreatitis, pancreatic cancer, abdominal trauma, and inflammation, e.g., sepsis, infections, acute pancreatitis, various forms of arthritis, cancer, complications of pregnancy, and postoperative states.

Potassium channel activating and inhibiting proteins and analogues, agonists and antagonists can be used to treat various diseases. Examples of these peptides are described in Edwards, G.; Weston, A. H; Pharmacology of the potassium channel openers. Cardiovascular Drugs & Therapy. 9 Suppl 2:185-93, 1995 March.

IgG activators, inhibitors and analogues, agonists and antagonists can be used to treat autoimmune diseases and immune dysfunctions. Examples of these peptides are described in Mouthon, L.; Kaveri, S. V.; Spalter, S. H.; Lacroix-Desmazes, S.; Lefranc, C.; Desai, R.; Kazatchkine, M. D; Mechanisms of action of intravenous immune globulin in immune-mediated diseases. Clinical & Experimental Immunology. 104 Suppl 1:3-9, 1996.

Endotoxin and inhibitors and analogues, agonists and antagonists can be used for decreasing cardiac output, systemic hypotension, decreased blood flow and $O_2$ delivery to tissues, intense pulmonary vasoconstriction and hypertension, bronchoconstriction, increased permeability, pulmonary oedema, ventilation-to-perfusion inequalities, hypoxaemia, and haemoconcentration. Examples of these peptides are named and described in Burrell, R; Human responses to bacterial endotoxin. Circulatory Shock. 43(3): 137-53, 1994 July.

Orphan receptor ligands (including but not limited to ADNF, Adrenomedullin, Apelin, Ghrelin, Mastoparan (MCD peptides), Melanin concentrating hormone, Nociceptin/Nocistatin, Orexin, Receptor activity modulating protein, Urotensin). By definition, orphan receptors do not have a function associated with them, but are considered to be key players in future drug development. These orphan receptor ligands are described in such references as In DS. Orphan G protein-coupled receptor s and beyond. Japanese Journal of Pharmacology. 90(2):101-6, 2002; Maguire J J. Discovering orphan receptor function using human in vitro pharmacology. Current Opinion in Pharmacology. 3(2):135-9, 2003; Szekeres P G. Functional assays for identifying ligands at orphan G protein-coupled receptor s. Receptor s & Channels. 8(5-6): 297-308, 2002; Shiau A K. Coward P. Schwarz M. Lehmann J M. Orphan nuclear receptor s: from new ligand discovery technologies to novel signaling pathways. Current Opinion in Drug Discovery & Development. 4(5):575-90, 2001; Civelli O. Nothacker H P. Saito Y. Wang Z. Lin S H. Reinscheid R K. Novel neurotransmitters as natural ligands of orphan G-protein-coupled receptor s. Trends in Neurosciences. 24(4):230-7, 2001; Darland T. Heinricher M M. Grandy D K. Orphan in FQ/nociceptin: a role in pain and analgesia, but so much more. Trends in Neurosciences. 21(5):215-21, 1998, the disclosures of which are incorporated herein by reference.

Another category includes Glycoprotein IIb/IIIa inhibitors. The central role of platelet-rich thrombus in the pathogenesis of acute coronary syndromes (ACSs) is well-known. Glycoprotein IIb/IIIa (Gp IIb/IIIa) receptor antagonists are potent inhibitors of platelet function that may be expected to affect favorably the natural history of ACSs. Exemplary references for this category include Bhatt D L. Topol E J. Current role of platelet glycoprotein IIb/IIIa inhibitors in acute coronary syndromes. JAMA. 284(12):1549-58, 2000; Kereiakes D J. Oral blockade of the platelet glycoprotein IIb/IIIa receptor: fact or fancy?. American Heart Journal. 138(1 Pt 2):S39-46, 1999; Bassand J P. Low-molecular-weight heparin and other antithrombotic agents in the setting of a fast-track revascularization in unstable coronary artery disease. Haemostasis. 30 Suppl 2:114-21; discussion 106-7, 2000.

The Use of Peptides Containing Desamino Alkyl Amino Acid(s) to Pass a Body Barrier The invention relates to a method of increasing the ability of a peptide to cross a body barrier of a subject by use of the extended or truncated peptide having as its N-terminus a residue of the compound formula I-IV.

The invention further relates to a method of treating or preventing in a subject a disease or condition treated or prevented by the administration of an extended or truncated peptide, whereby the extended or truncated peptide crosses the body barrier in higher amounts than the peptide having no non-natural amino acid.

The invention also relates to a method of treating or preventing in a subject a disease or condition of the brain treated or prevented by the administration of an extended or truncated peptide.

The use of peptides as therapeutic agents is limited by their inability to cross body barriers. The phrase "body barrier" is defined herein as a cellular membrane or other structure that functions to prevent free (e.g., diffusional) passage of certain molecules. The use of an extended or truncated peptide of the invention facilitates the passage of the resultant peptide through a variety of body barriers. Examples of body barriers include, but are not limited to, the blood brain barrier, a cell membrane, intestinal epithelium, skin cell, or the blood—ocular. In a preferred embodiment, the body barrier is the blood brain barrier.

Selectivity and Stability of Peptides Non-Natural Amino Acid(s)

Certain embodiments of the invention relate to a method of increasing the selectivity of a chosen peptide through use of an extended or truncated peptide based upon the sequence of the chosen peptide as described above.

Enhancing the selectivity of a drug to a biological target is of great importance. In one embodiment, a peptide containing arginine and/or lysine can be converted according to the invention into an extended or truncated peptide in order to increase the selectivity of the peptide. In another embodiment, any of the non-natural amino acids disclosed herein can be used to increase the selectivity of a peptide.

Pharmaceutical Composition

The peptides of the invention can be used in any therapeutic procedure available to one of skill in the art to treat any disease or physiological problem with which the corresponding known peptide is associated.

The peptides of the invention can be formulated as pharmaceutical compositions and administered to a mammalian host, such as a human patient, in a variety of dosage forms adapted to the chosen route of administration, i.e., orally or parenterally, by intravenous, intramuscular, topical or subcutaneous routes.

Thus, the peptides may be systemically administered, for example, intravenously or intraperitoneally by infusion or injection. Solutions of the peptide or peptide conjugate can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient(s) that are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the peptide or peptide conjugate in the required amount in the appropriate solvent with various of the other ingredients enumerated above, as required, followed by filter sterilization. In the case of sterile powders for the preparation of sterile injectable solutions, the preferred methods for preparation of such powders are vacuum drying and freeze drying techniques, which yield a powder of the active ingredient plus any additional desired ingredient present in the previously sterile-filtered solutions.

In some instances, the peptides of the invention can also be administered orally, in combination with a pharmaceutically acceptable vehicle such as an inert diluent or an assimilable edible carrier. The peptides may be enclosed in hard or soft shell gelatin capsules, may be compressed into tablets, or may be incorporated directly with the food of the patient's diet. For oral therapeutic administration, the peptide or peptide conjugate may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% to about 90% of the weight of a given unit dosage form. The amount of peptide in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the peptides of the invention may be incorporated into sustained-release preparations and devices.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the peptides of the invention can be determined by correlating their in vitro activity, and in vivo activity in animal models described herein.

The therapeutically effective amount of peptide of the invention necessarily varies with the subject and the disease or physiological problem to be treated and correlates with the effective amounts of the corresponding known peptide. For example, a therapeutic amount between 30 to 112,000 μg per kg of body weight can be effective for intravenous administration. As one skilled in the art would recognize, the amount can be varied depending on the method of administration. The amount of the peptide of the invention, required for use in treatment will also vary with the route of administration, but also the nature of the condition being treated and the age and condition of the patient and will be ultimately at the discretion of the attendant physician or clinician.

The compound can conveniently be administered in unit dosage form; for example, containing 1 to 1000 mg, conveniently 10 to 750 mg, most conveniently, 20 to 500 mg of peptide per unit dosage form.

Ideally, the peptide should be administered to achieve peak plasma concentrations of from about 0.1 to about 75 μM, preferably, about 1 to 50 μM, most preferably, about 2 to about 30 μM. This may be achieved, for example, by the intravenous injection of a 0.05 to 5% solution of the peptide, optionally in saline, or orally administered as a bolus containing about 1-100 mg of the peptide. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose, as divided doses, or as a continuous infusion. The desired dose can also be administered at appropriate intervals, for example, as two, three, four or more sub-doses per day.

Cosmetic Formulation

An important role for makeup cosmetic is "beautification" or making the appearance more beautiful. Often which role involves correction of skin roughness, blemishes and color as well as vitality.

A cosmetic composition of the present invention contains the typical and common base carriers as well as a desamino alkyl amino acid compound of the invention. Usually the compound of the invention will be in the form of an ester, amide or salt for this purpose. Generally, the cosmetic base will depend upon the kind of make-up being formulated: face creme, face powder, pancake make-up, skin creme, lip stick, rouge and the like. These bases will contain appropriate, nontoxic colorants, emuliants, oils, waxes, solvents, emulsifiers, fatty acids, alcohols or esters, gums, inorganic inert builders and the like.

For example, the gums, may include various known polysaccharide compounds, for example, cellulose, hemicellulose, gum arabic, tragacanth gum, tamarind gum, pectin, starch, mannan, guar gum, locust bean gum, quince seed gum, alginic acid, carrageenan, agar, xanthane gum, dextran, pullulan, chitin, chitosan, hyaluronic acid, chondroitin sulfuric acid, etc., derivatives of polysaccharide compounds, for example, carboxymethylated derivatives, sulfate derivatives, phosphated derivatives, methylated derivatives, ethylated derivatives, addition derivatives of alkylene oxide such as ethylene oxide or propylene oxide, acylated derivatives, cationated derivatives, low molecular weight derivatives, and other polysaccharide derivatives may be mentioned.

Another component which may be included in the external composition of the present invention is a powder component. Powder components based on inorganic components such as talc, kaolin, mica, sericite, dolomite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal salts of tungstenic acid, magnesium, silica, zeolite, barium sulfate, sintered calcium sulfate (sintered gypsum), calcium phosphate, fluorapatite, hydroxyapatite, ceramic powder, metal soap (zinc myristate, calcium palmitate, ammonium stearate), boronitride, etc.; and organic powder components such as polyamide resin powder (nylon powder), polyethylene powder, polymethyl methacrylate powder, polystyrene powder, copolymer resin powder of styrene and acrylic acid, benzoguanamine resin powder, silicone resin powder, silicone rubber powder, silicone resin covered rubber powder, polyethylene tetrafluoride powder, cellulose powder, etc. may be mentioned.

Further, powder components obtained by treating the surfaces of these powder components by a silicone compound, fluorine-modified silicone compound, fluorine compound, higher aliphatic acid, higher alcohol, aliphatic acid ester, metal soap, alkyl phosphate, etc. may be formulated into the external composition of the present invention depending upon the need.

The known dyes or pigments, may be used. For example, inorganic white pigments such as titanium dioxide, zinc oxide, inorganic red pigments such as iron oxide (bengala), iron titanate, inorganic brown pigments such as .gamma.-iron oxide; inorganic yellow pigments such as yellow iron oxide, yellow earth; inorganic black pigments such as black iron oxide, carbon black, lower titanium oxide, and; inorganic violet pigments such as mango violet, cobalt violet; inorganic green pigments such as chromium oxide, chromium hydroxide, cobalt titanate; blue pigments such as prussian blue, ultramarine; pearl pigments such as titanium oxide coated mica, titanium oxide coated bismuth oxichloride, titanium oxide coated talc, colored titanium oxide coated mica, bismuth oxichloride, fish scales; metal powder pigments such as aluminum powder, copper powder; organic pigments of zirconium, barium or aluminum lakes etc. such as Lithol rubine B (Red No. 201), Lithol rubine BCA (Red No. 202), Lake red CBA (Red No. 204), Lithol red (Red No. 205), Deep maroon (Red No. 220), Helidone pink CN (Red No. 226), Permatone Red (Red No. 228), Permanent red F5R (Red No. 405), Permanent orange (Orange No. 203), Benzidine Orange (Orange No. 204), Benzidine yellow G (Yellow No. 205), Hanza Yellow (Yellow No. 401), Blue No. 404, and other organic pigments; Erythrosine (Red No. 3), Phloxine B (Red No. 104), Acid red (Red No. 106), Fast acid magenta (Red No. 227), Eosine YS (Red No. 230), Violamine R (Red No. 401), Oil red XO (Red No. 505), Orange II (Orange No. 205), Tartrazine (Yellow No. 4), Sunset yellow FCF (Yellow No. 5), Uranin (Yellow No. 202), Quinoline yellow (Yellow No. 203), Fast green FCF (Green No. 3), Brilliant blue FCF (Blue No. 1) may be mentioned.

The cosmetic composition of the present invention may be formulated with a liquid. As the liquid, it is possible to select a volatile component ordinarily used in external compositions such as cosmetics. Specifically, it is possible to mention, for example, volatile silicone oil, water, or a lower alcohol (or mixtures of the same). These volatile components may be suitably selected depending upon the specific form of the external composition of the present invention (for example, the later mentioned "roughness correcting composition" or "makeup composition" etc.) or type of carrier (for example, oil base or emulsion base etc.). By formulating these volatile components, it is possible to adjust the viscosity of the product at the time of use of the external composition of the present invention and adjust the thickness of coating of the external composition on the skin.

As the volatile silicone oil, it is possible to use a volatile silicone oil which is used in the field of cosmetics and other external compositions. It is not particularly limited. Specifically, for example, a low boiling point linear silicone oil such as hexamethyl disiloxane, octamethyl trisiloxane, decamethyl cyclopentasiloxane, dodecamethyl cyclohexasiloxane, and tetradecamethyl cycloheptasiloxane; a low boiling point cyclic silicone oil such as octamethyl cyclotetrasiloxane, decamethyl cyclopentasiloxane, dodecamethyl cyclohexasiloxane, and tetradecamethyl cycloheptasiloxane; etc. may be mentioned.

The external composition of the present invention may contain, depending upon the need, the following other components as auxiliary components to an extent not detracting from the desired effect of the present invention.

For example, as the oil component, hydrocarbon oils such as liquid paraffin, isoliquid paraffin, squalane, oils and fats such as olive oil, palm oil, coconut oil, *macadamia* nut oil, jojoba oil; higher alcohols such as isostearyl alcohol; ester oils such as higher aliphatic oils and isopropyl myristate, etc. may be formulated in the external composition of the present invention. Among these oil components, in particular, formulating a polar oil in the external composition of the present invention enables improvement of the stability with the elapse of time.

Further, a benzophenon derivative, para-aminobenzoate derivative, para-methoxysuccinate derivative, salicylate derivative, and other UV absorbers; humectants, blood circulation promoters, refrigerants, antiperspirants, bactericides, skin activators, anti-inflammatory agents, vitamins, antioxidants, antioxidant adjuvants, preservatives, flavors and fragrances, etc. may be blended in the external composition of the present invention.

The cosmetic formulation of the present invention may be produced in an appropriate medium including but not limited to a paste, a powder, a cake, a crème, an oil, a lotion, a grease, a wax or similar cosmetic bases. The process to produce involves combining the cosmetic ingredients and desamino, alkyl amino acid compound of any of formulas I-IV preferably as the ester, amide or salt. The combination is mixed, kneaded, rolled, ground, heated or otherwise treated to form a substantially homogeneous mass or mixture for use. These steps can be accomplished by use of a kneader, grind wheel, rollers, mixer, heat exchanger, extruder and the like.

As explained above, the invention is exemplified by modification of the natural peptide neurotensin. In the following section, the gackground, modification and biological activity of neurotensin and the corresponding peptides of the invention are discussed.

Neurotensin Structure and Biology

Neurotensin (NT) was first isolated from bovine hypothalami as a hypotensive peptide by Carraway and Leeman in 1973. Since then, NT has been shown to have numerous distinct physiological effects in the central nervous system (CNS) and the periphery. Hypothermia, antinociception, attenuation of d-amphetamine-induced hyperlocomotion, and potentiation of barbiturate-induced sedation are promoted by direct injection of NT into the brain. Peripherally, NT acts as a hormone to induce hypotension and decrease gastric acid secretion. Structurally, NT is a linear tridecapeptide with the following sequence: pGlu-Leu-Tyr-Glu-Asn-Lys-Pro-Arg-Arg-Pro-Tyr-Ile-Leu-OH (SEQ ID NO:1). Early in the history of NT research, it was shown that the C-terminal hexapeptide fragment, $Arg^8$-$Arg^9$-$Pro^{10}$-$Tyr^{11}$-$Ile^{12}$-$Leu^{13}$ [NT(8-13); SEQ ID NO:2], was equipotent at producing the physiological effects of NT in vitro and in vivo. NT(9-13) corresponds to SEQ ID NO:12.

Tanaka and colleagues first identified an NT receptor ($NTR_1$) from rat brain in 1990. Since then, human $NTR_1$ has been successfully cloned and expressed. Both are classic G-protein coupled receptors containing seven transmembrane (7TM) domains and share 84% homology. Second messenger systems, including cGMP production, calcium mobilization, and phosphatidylinositol turnover, are triggered upon $NTR_1$ activation. The mRNA for $NTR_1$ is expressed in both rat and human brain and intestine. A second NT receptor ($NTR_2$) with a substantially lower affinity for NT than $NTR_1$, ($K_d \cong 2.5$ and 0.5 nM respectively), also has been identified in rat and human brain (23-25). $NTR_2$ is also a 7TM/G-protein coupled receptor, yet has a shorter N-terminal extracellular tail and a longer third intracytoplasmic loop compared to $NTR_1$. A third receptor ($NTR_3$) was cloned from a human brain cDNA library and found to be identical to the previously cloned gp95/sortilin. $NTR_3$ is a non-G-protein coupled sorting protein having only a single transmembrane region.

NT as an Endogenous Neuroleptic

Several distinct lines of evidence implicate NT in the pathophysiology of schizophrenia. Advances in the dopamine theory of schizophrenia support that a flaw in the convergence of various neural circuits on the mesolimbic dopamine system is responsible for the development of the disorder. The anatomical positioning of the NT system is such that it interacts with the glutaminergic, dopaminergic, GABAergic, and serotonergic systems within the brain. In particular the NT and dopamine systems are closely related within the nucleus accumbens, the area of the brain believed to be responsible for delusions and hallucinations. $NTR_1$ receptors are dense in the ventral tegmental area, a brain region closely associated with the neuronal systems described above. Almost 90% of NT receptors are located on dopaminergic neurons and over 80% of dopamine neurons in the brain express $NTR_1$. Co-localization of the NT system with brain regions implicated in schizophrenia also imply its involvement.

Neurotensin and its Biological Activity

Since NT was hypothesized as an "endogenous neuroleptic" and NT(8-13) was identified as its active fragment, efforts have been made to develop NT(8-13) derivatives as potential antipsychotics. Two groups in particular, the Eisai pharmaceutical company (Tokyo, Japan) and the Richelson research group (Mayo Clinic, Jacksonville, Fla.) have prepared numerous derivatives of NT(8-13) analogues that showed promise as antipsychotic drugs. In particular, amino acid substitutions at $Arg^8$, $Arg^9$, $Tyr^{11}$, and $Ile^{12}$ have yielded several analogues that are centrally active after peripheral administration.

An Eisai compound (the Eisai hexapeptide) was the first NT(8-13) analogue that elicited behavioral effects after peripheral administration. However, the various modifications incorporated in this peptide resulted in a 700-fold loss of binding affinity at $NTR_1$. In addition, this analogue was not able to elicit central activity after oral administration.

More recently, NT69L has been developed by the Richelson group as an NT(8-13) analogue that maintains nanomolar binding affinity at $NTR_1$ ($K_d$=1.55 nM) (55) and exhibits a pronounced hypothermic effect after a 1 mg/kg injection (−5.3° C. at 90 min PI) (41). NT69L also attenuates hyperactivity induced by both cocaine and d-amphetamine. However, tolerance to its hypothermic effect and to its suppression of d-amphetamine induced hyperactivity was observed after chronic administration of the compound. As with the Eisai hexapeptide, NT69L produced only a slight hypothermic response after oral administration.

Summary of Neurological Effects of the NT Peptides of the Invention

The N-terminal alpha methyl, alpha desamino homolysyl and orinthyl analogues of NT(8-13) prepared according to the invention (see the foregoing general discussion and the Examples) were synthesized and screened for activity in numerous behavioral assays predictive of antipsychotic potential. These peptides induced hypothermia in a dose-dependent fashion after oral administration. In addition, oral administration of the peptides significantly reduced d-amphetamine induced hyperlocomotion, a measure of the therapeutic efficacy of current or potential APDs. The low dose of peptide (10 mg/kg) that elicits a significant response after oral administration in these assays is significant. The peptides also demonstrate an ability to maintain efficacy after repeated administration. In fact they demonstrate an ability to increase maximal hypothermic response over time, implying that repeated administration may actually improve their CNS activity. Thus, the NT peptides of the invention are shown to have biological activity like that of the known naturally occurring peptide NT and are more selective.

Details of these effects are as follows.

Hypothermia as a Preliminary Screen of CNS Activity

NT induces hypothermia when directly administered into the CNS. As a result, induced hypothermia can be used to determine the ability of NT(8-13) peptides of the invention to cross the BBB after peripheral administration and indirectly to determine their in vivo CNS activity. The hypothermic effect of NT can be attributed to its actions at $NM_1$, the NTR most often implicated in the pathophysiology of schizophrenia. An NT(8-13) peptide that induced hypothermia after IP injection is thus shown to be an antipsychotic agent. A significant hypothermic effect would demonstrate that the peptide showed marked improvements in blood stability and membrane crossing.

IP injection is the standard route of administration to determine the extent of BBB crossing of neurotensin analogues. The methods and protocols are provided in the Examples section. IV administration results in a dose that is completely available to the systemic circulation. By contrast, an IP injection is a more rigorous test of stability because the peptide is exposed to first pass metabolism in the liver.

The hypothermic effects of peptides 28-30, after a 5 mg/kg IP injection, are given in Table 2. Each peptide exhibited a significant effect over a 5 hr time course. The hypothermic results for these three peptides demonstrate that the substitution of an alpha alkyl group in place of the N-terminal amine group (i.e., the α-methyl group) does not abolish the in vivo activity of the NT(8-13) peptide. For use as an antischizophrenic pharmaceutical, the ability of these peptides to elicit CNS activity after oral administration was evaluated.

TABLE 1

Amino acid sequence of NT(8-13) analogues.
ABS201 (SEQ ID NO: 3); KH29 (SEQ ID NO: 4); KH30 (SEQ ID NO: 5).

| Peptide | N-terminus | 8[a] | 9 | 10 | 11 | 12 | 13 | C-terminus |
|---|---|---|---|---|---|---|---|---|
| ABS201 | $CH_3$ | L-Hlys | L-Arg | L-Pro | L-Tyr | L-tLeu | L-Leu | COOH |
| KH29 | $CH_3$ | 7 | L-Arg | L-Pro | L-Tyr | L-tLeu | L-Leu | COOH |
| KH30 | $CH_3$ | 9 | L-Arg | L-Pro | L-Tyr | L-tLeu | L-Leu | COOH |

TABLE 2

Hypothermic response to IP administration of NT(8-13) and NT(8-13) analogues.
NT(8-13) (SEQ ID NO: 2); ABS201 (SEQ ID NO: 3);
KH29 (SEQ ID NO: 4); KH30 (SEQ ID NO: 5).

| Peptide[a] | $t_{max}$ (min)[b] | Δ in BT (° C.)[c] |
|---|---|---|
| NT(8-13) | 90 | −0.45 ± 0.17[d] |
| ABS201 | 150 | −2.51 ± 0.17 |
| KH29 | 150 | −3.75 ± 0.24 |
| KH30 | 300 | −3.84 ± 0.20 |

[a]IP dose was 5 mg/kg for all peptides.
[b]$t_{max}$ (min) = Time to maximal temperature decrease.
[c]Δ in BT (° C.) = Decrease in body temperature measured at $t_{max}$
[d]N = 5 for all peptides.

Oral Administration

A goal in the development of NT(8-13) peptides as antischizophrenic pharmaceuticals is to determine their ability to exhibit CNS activity after oral administration. The known NT peptides, NT69L and the Eisai hexapeptide, fail in this respect to elicit central activity when given orally. Accordingly, the N-terminal methyl peptides 28-30 were tested for their ability to induce hypothermia after oral administration.

Figure 9:
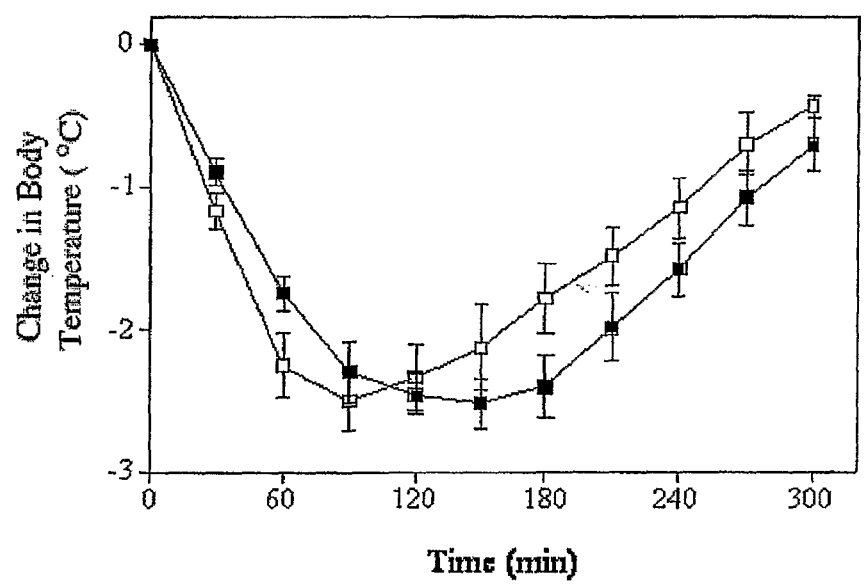
FIG. 9. Hypothermic effects of ABS201 after IP (solid symbols) and oral administration (open symbols).
Figure 10:
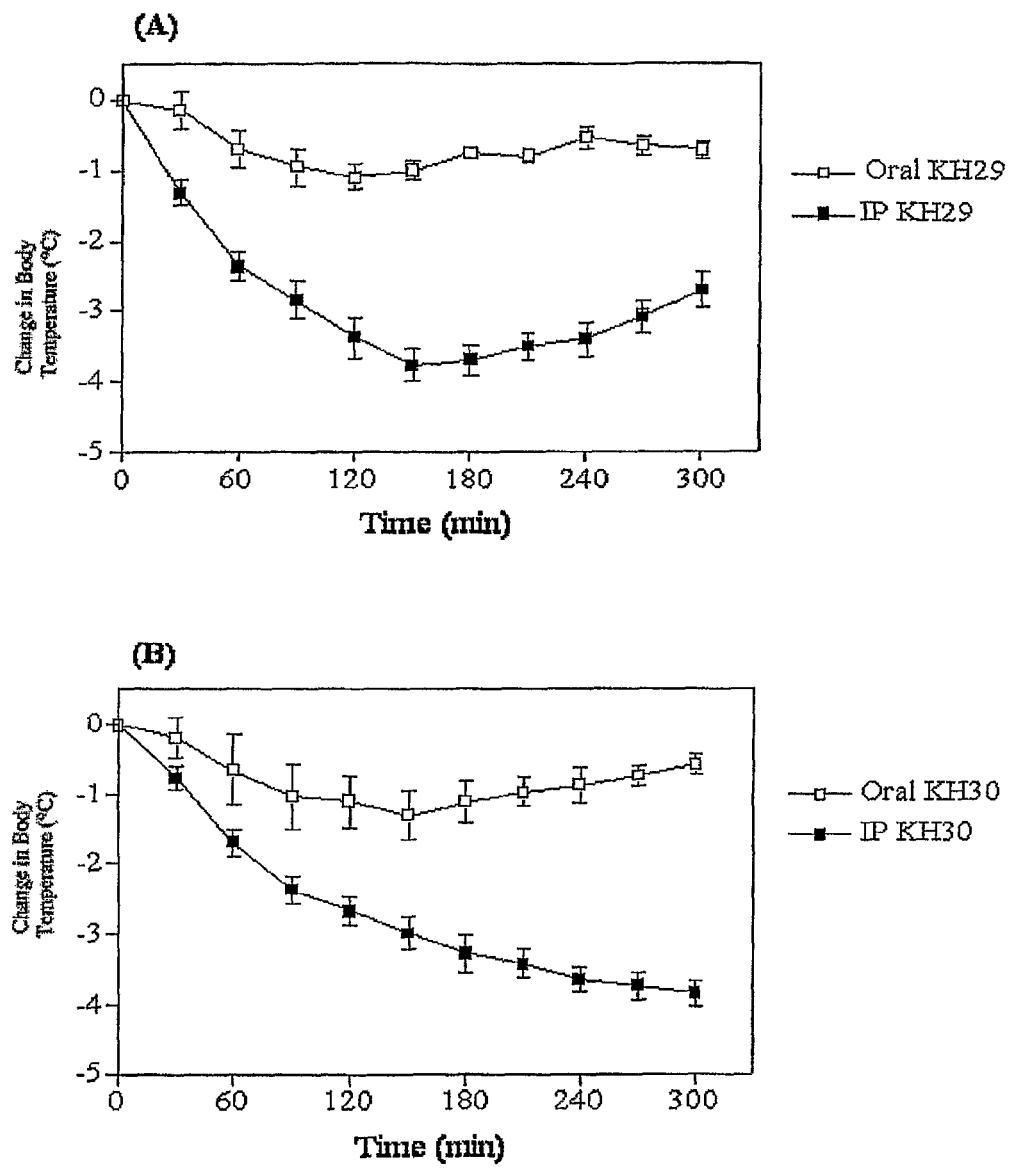
FIG. 10A-10B. Comparison of hypothermic effects after IP and oral administration for KH29 (10A) and KH30 (10B).

ABS201, an example of a peptide of the invention, demonstrated maximal hypothermic responses greater than 2° C. (Table 3) and its maximal hypothermic effect was equal to its hypothermic effect after IP dosing (FIG. 9), resulting in an approximate oral bioavailability of 25%. While peptides 29 and 30 also were orally active, their ratio of oral activity to IP activity was not as balanced as that of ABS201. The oral activity of ABS201 was an important factor to support it as a lead NT(8-13) analogue for further evaluation of antipsychotic potential.

TABLE 3

Hypothermic response to chronic IP administration of ABS201.

| Peptide[a] | $t_{max}$ (min)[b] | Δ in BT (° C.)[c] |
|---|---|---|
| Saline[d] | 180 | 0.70 ± 0.20 |
| Day 1 | 120 | 2.72 ± 0.24 |
| Day 2 | 90 | 2.85 ± 0.26 |

TABLE 3-continued

Hypothermic response to chronic IP administration of ABS201.

| Peptide[a] | $t_{max}$ (min)[b] | Δ in BT (° C.)[c] |
|---|---|---|
| Day 3 | 120 | 3.74 ± 0.13 |
| Day 4 | 120 | 3.71 ± 0.13 |
| Day 5 | 90 | 3.83 ± 0.24 |

[a]IP dose was 5 mg/kg for all days.
[b]$t_{max}$ (min) = Time to maximal temperature decrease.
[c]Δ in BT (° C.) = Decrease in body temperature measured at $t_{max}$
[d]N = 5 for all days.

TABLE 4

Comparison of the maximal hypothermic effects of peptide ABS201 after IP administration.

| Dose | Peptide ABS201[a] |
|---|---|
| 0.1 mg/kg | −1.14 ± 0.21 |
| 0.5 mg/kg | −1.92 ± 0.12 |
| 1.0 mg/kg | −2.63 ± 0.21 |
| 5.0 mg/kg | −3.61 ± 0.22 |

[a]Change in body temperature (° C.) is the maximal decrease recorded for each individual dose.

Schizophrenia Investigation

The blockade of locomotion caused by d-amphetamine, a "DA agonist", has become the standard measure of therapeutic efficacy of current or potential drug candidates for treatment of schizophrenia. This model operates on the assumption that the direct stimulation of DA receptors within the mesolimbic DA system is responsible for the locomotor response.

Catalepsy, commonly defined as a state of tonic immobility in rodents, is regarded as analogous to (extrapyramidal side effects) EPSEs in humans. Consequently, catalepsy is a side effect to be avoided in a successful drug candidate. Concurrently, the degree to which a drug candidate causes catalepsy in rats may also be used as a predictor for the probable occurrence of EPSEs associated with that particular candidate.

Hypothermic Analysis

To examine the antipsychotic properties of ABS201, a dose-response curve for hypothermic induction after IP administration was generated. In addition, the hypothermic effects elicited by oral administration of ABS201 (10 mg/kg-30 mg/kg) were determined. The ability of ABS201 to reduce d-amphetamine induced hyperlocomotion after both IP and oral administration also was measured. To assess the effects on CNS activity caused by prolonged treatment of ABS201, hypothermia and attenuation of d-amphetamine induced hyperlocomotion were measured after repeated daily dosing. Finally, the bar test was utilized to measure catalepsy as a predictor of EPSEs in humans.

The dose-response curve for ABS201 after IP injection over a concentration range of 0.1-10 mg/kg (FIG. 11) gave some conflicting results. First, the maximal effect elicited at 5 mg/kg (−3.61±0.22° C. at 150 min PI) was a full degree greater than the maximal effect seen after the preliminary screen (−2.51±0.17° C. at 150 min PI). This discrepancy is most likely due to environmental factors (air temperature, rectal probes, rat size, etc.) that can affect the rats' response. Most importantly, ABS201 continued to elicit a significant CNS effect irrespective of these differences. The $ED_{50}$ value for ABS201, 0.943 mg/kg., compares favorably with other NT(8-13) analogues with CNS activity (41, 60).

Figure 12:
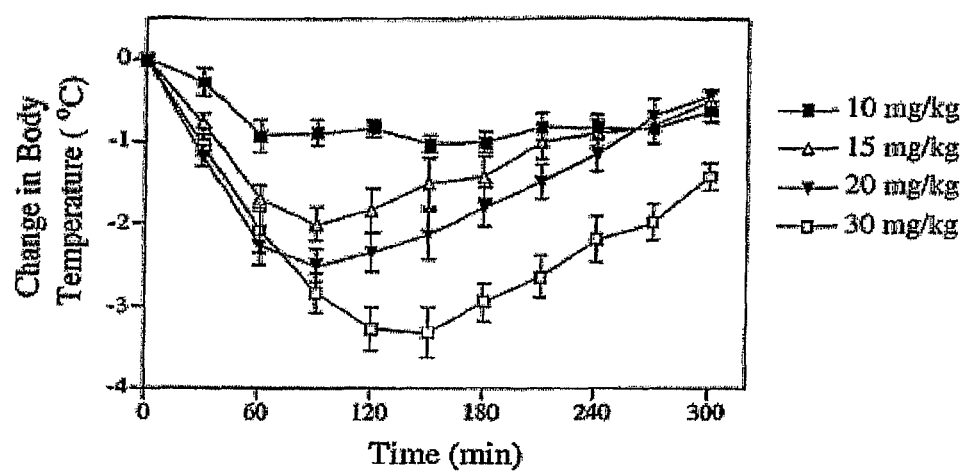
FIG. 12. Dose-dependent hypothermic response to ABS201 after oral administration.

ABS201 also induced hypothermia in a dose-dependent fashion after oral administration (FIG. 12). A significant hypothermic effect was demonstrated at 10 mg/kg, the lowest dose tested (−1.02±0.10° C. at 150 min PI). The generation of an $ED_{50}$ value for the oral administration of ABS201 was impractical due to the inordinate amount of peptide necessary to produce a complete dose-response curve. Previous NT(8-13) analogues that have been under development as antipsychotic compounds have contained a Trp[11] substitution. Evidence from the studies presented herein supports the theory that this modification abolishes the oral activity of a NT analogue. Further studies are necessary to determine what specific role Tyr[11] plays in the oral bioavailability of NT(8-13) analogues.

The blockade of locomotion caused by d-amphetamine, a "DA agonist", has become the standard measure of therapeutic efficacy of current or potential schizophrenia drug candidates, and NT(8-13) analogues currently under investigation as candidates have demonstrated the ability to decrease d-amphetamine induced hyperactivity in a dose-dependent fashion. Sound- and light-attenuated locomotor cages are used to measure the ability of potential candidates to decrease d-amphetamine-induced hyperactivity.

The effects of ABS201 on d-amphetamine induced hyperactivity at varying doses were also examined. ABS201 significantly reduced hyperlocomotion for all doses tested (doses of 3 mg/kg and 10 mg/kg not shown). Another hallmark of current APDs is the ability to reduce spontaneous locomotor activity. All ABS201 dose groups responded significantly lower than saline during the drug phase, indicating the ability of ABS201 to reduce spontaneous activity.

The ability to attenuate d-amphetamine induced hyperlocomotion after oral administration is also demonstrated by ABS201. During the drug phase, only the 10 and 30 mg/kg doses reduced spontaneous locomotor activity. The lack of significance seen with the 20 mg/kg dose is most likely an anomaly resulting from slight variation in response for this group of rats. However, no main effect of DOSE was detected during the baseline phase, indicating that there is not a significant difference in baseline activity across the different dosing groups.

ABS201 maintained a significant CNS effect after repeated daily dosing (Table 3) and over the 5-day period the absolute hypothermic response increased. A comparison of the induced hypothermia of ABS201 on days 1 and 5 was made. On day 5, the maximal hypothermic response was achieved faster (90 min) compared to day 1 (120 min). In contrast to day 1, on day 5 the maximal hypothermic effect was not maintained for an extended period, implying that while repeated dosing does not decrease the maximal effect, it may reduce the duration of the hypothermic effect. Repeated daily dosing had no effect on the ability of ABS201 to attenuate d-amphetamine induced hyperlocomotion. Both the acute and chronic dosing groups produced a reduction in hyperactivity that was significant for almost two hours after amphetamine administration. Of note, chronic administration of ABS201 did abolish its inhibitory effect on spontaneous locomotor activity.

Cataleptic Analysis

In laboratory tests, catalepsy is characterized by the inability of an animal to correct its position after placement in an unnatural posture. Catalepsy tests can be greatly influenced by a number of variables. These include stress-induced inhibition of catalepsy caused by a new environment and the contribution of learned "pseudo-catalepsy" that can result upon repeated measures with the same animal. To circumvent these potential confounding factors, tests are performed on an animal only once in a quiet, controlled environment.

Neither ABS201 (5 mg/kg) nor saline caused catalepsy after peripheral administration. Haloperidol, a typical antischizophrenic drug known to produce a fully cataleptic response in rats, induced catalepsy that lasted for greater than 30 sec. These results demonstrate that ABS201 does not induce catalepsy after peripheral administration, a hallmark of current clinically effective candidates.

Bioavailability Study with CACO-2 Cells

Caco-2 cells, derived from a human colorectal carcinoma, spontaneously differentiate into polarized cells that exhibit well-developed microvilli and brush-border enzymes. These features make the cells an excellent model of the human small intestine. A strong correlation between uptake of a compound in the Caco-2 cell model and oral bioavailability of the compound has been identified.

ABS201 is stable in rat serum for greater than 24 hours, however, its stability in cells has not been determined. Consequently, determination of the ability of intact peptide to enter the Caco-2 cells in the uptake experiments will show oral bioavailability and cellular stability. Reverse phase HPLC is an ideal method to analyze the solubilized cell components for ABS201 and ABS201 degradation products. This analysis will show oral availability and cellular stability. Fractions can be collected at determined intervals and counted for radioactivity via LSC. By establishing the ABS201 elution time via a standard gradient, direct comparisons can be made to the contents of Caco-2 cells after uptake experiments.

To verify that intact peptide is entering the Caco-2 cells and in a preliminary attempt to assess the stability of the peptides in cell culture, a RP-HPLC assay to analyze ABS201 after cellular uptake can be carried out. After a 2 min incubation, intact ABS201 likely can be identified within the cells using HPLC techniques. These studies will demonstrate that ABS201 can be extensively taken up by the Caco-2 cells thus showing its oral bioavailability.

EXPERIMENTAL EXAMPLES AND PROTOCOLS

The following examples and protocols are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and is at room temperature, and pressure is at or near atmospheric.

Starting Materials. Solvents are from Fisher Scientific (Pittsburgh, Pa.) and reagents from Aldrich (Milwaukee, Wis.) unless otherwise noted.

Abbreviations. Trisyl-$N_3$, 2,4,6-triisopropylbenzenesulfonyl azide; $Et_3N$, triethylamine; t-BuCOCl, trimethylacetylchloride; n-BuLi, n-butyl lithium; $H_2$, hydrogen gas; Pd—C, palladium on activated carbon; Xps, (S)-(−)-4-benzyl-2-oxazolidinone; KHMDS, potassium bis(trimethylsilyl)amide; $CH_3I$, methyl iodide; $H_2O_2$, hydrogen peroxide; LiOH, lithium hydroxide; THF, tetrahydrofuran; $CH_2Cl_2$, dichloromethane; $MgSO_4$, magnesium sulfate; Hex, hexane; EtOAc, ethyl acetate; $NaHCO_3$, sodium bicarbonate; HCl, hydrochloric acid; $N_2$, nitrogen; $H_2O$, distilled water.

Example 1

(3 (2S),4S)-3-(2-methyl-5-bromo-1-oxovaleryl)-4-(phenylmethyl)-2-oxazolidinone(24a) (FIG. 3). Intermediate 23a was prepared as described previously (57). A solution of 17.4 mL (5 eq) of potassium bis(trimethylsilyl) amide (KHMDS) was added to 100 mL anhydrous tetrahydrofuran (THF) and cooled to −78° C. under positive nitrogen ($N_2$) pressure. A solution of 23a (5.18 g, 15.23 mmol) in 10 mL THF under $N_2$ was cooled to −78° C. and cannulated into the KHMDS solution. This mixture was stirred at −78° C. for 30 min to effect enolate formation. Methyl iodide ($CH_3I$) (1.90 mL, 2 eq) was added to the solution via cannula and stirred at −78° C. for 1 hr at which time the reaction was quenched with 4.09 mL (5 eq) of glacial acetic acid. The solution was warmed to room temperature while stirring over 2 hr and the THF removed in vacuo. The resulting yellow slurry was dissolved in 200 mL half-saturated brine and extracted with $CH_2Cl_2$ (3×100 mL). The $CH_2Cl_2$ layers were combined, dried over anhydrous magnesium sulfate ($MgSO_4$), filtered, and evaporated in vacuo to yield a yellow oil. The crude oil was purified over silica gel eluting with 3:1 hexane:ethyl acetate (Hex: EtOAC) to give 2.81 g (52% yield) of pure 26a. $^1$H NMR (400 MHz, $CDCl_3$) δ 7.38-7.15 (m, 5H), 4.71-4.63 (m, 1H), 4.18-4.15 (d, J=5.0 Hz, 2H), 3.71-3.65 (m, 1H), 3.41-3.33 (m, 2H), 3.27-3.20 (dd, J=4.0, 13.8 Hz, 1H), 2.89-2.81 (dd, J=10.0, 14.2 Hz, 1H), 1.90-1.55 (m, 4H), 1.24-1.20 (d, J=7.4, 3H); $^{13}$C NMR (100 MHz, $CDCl_3$) δ 176.8, 153.2, 135.2, 129.6, 129.1, 127.6, 66.4, 55.6, 38.3, 37.6, 33.8, 32.2, 31.8, 17.9.

Example 2

(3 (2S),4S)-3-(2-methyl-6-bromo-1-oxohexanyl)-4-(phenylmethyl)-2-oxazolidinone (24b). A slightly modified procedure was used to give 24b. Directly following KHMDS addition to 23b, 5 eq of $CH_3I$ was added and the reaction stirred at −78° C. under $N_2$ for 1 hr. Quenching with glacial acetic acid and subsequent extraction and purification protocol was as described above for 24a. Additional silica gel purification eluting with 100% $CH_2Cl_2$ gave pure 24b in 10% yield. $^1$H NMR (400 MHz, $CDCl_3$) δ 7.36-7.19 (m, 5H), 4.72-4.65 (m, 1H), 4.25-4.16 (d J=4.2 Hz, 2H), 3.77-3.67 (m, 1H), 3.46-3.36 (t, J=7.0 Hz, 2H), 3.29-3.22 (dd, J=4.0, 14.0 Hz, 1H), 2.82-2.74 (dd, J=9.0, 14.0 Hz, 1H), 1.92-1.74 (m, 3H), 1.50-1.42 (m, 3H), 1.25-1.21 (d, J=7.2 Hz, 3H); $^{13}$C NMR (100 MHz, $CDCl_3$) δ 176.9, 153.2, 135.3, 129.6, 129.1, 66.4, 55.6, 38.1, 37.8, 34.1, 32.8, 32.5, 26.1, 18.7.

Example 3

(3(2S),4S)-3-(2-methyl-7-bromo-1-oxoheptyl)-4-(phenylmethyl)-2-oxazolidinone (24c). Compound 24c was produced in 56% yield from 23c following the procedure outlined for compound 26a. $^1$H NMR (400 MHz, $CDCl_3$) δ 7.41-7.22 (m, 5H), 4.74-4.66 (m, 1H), 4.25-4.19 (d, J=4.0 Hz, 2H), 3.77-3.70 (m, 1H), 3.45-3.39 (t, J=7.0 Hz, 2H), 3.31-3.23 (dd, J=3.7, 13.7 Hz, 1H), 2.84-2.77 (dd, J=10.0, 12.5 Hz, 1H), 1.91-1.77 (m, 3H), 1.50-1.32 (m, 5H), 1.25-1.20 (d, J=7.0 Hz, 3H); $^{13}$C NMR (100 MHz, $CDCl_3$) δ 177.2, 153.1, 135.4, 129.7, 129.1, 127.5, 66.4, 55.7, 38.2, 37.9, 34.3, 33.4, 32.8, 28.4, 27.7, 17.8.

Example 4

2(S)-Methyl-5-bromovaleric acid (25a). A solution of 24a (10.41 g, 29.4 mmol) in 100 mL THF and 40 mL $H_2O$ was cooled to 0° C. while stirring. To this solution was added 12.12 mL (3.5 eq) 30% hydrogen peroxide ($H_2O_2$) followed by 2.41 g (2 eq) lithium hydroxide (LiOH) and the solution was stirred at 0° C. for 50 min. After 50 min, 94 mL sodium sulfite (0.183 g/mL $H_2O$) and 288 mL 0.5N sodium bicarbonate ($NaHCO_3$) were added. The THF was removed in vacuo and the remaining aqueous solution extracted with $CH_2Cl_2$ (3×100 mL). The aqueous layer was acidified to pH 2 with 25% HCl and extracted with EtOAc (3×100 mL). The EtOAc fractions were combined and concentrated in vacuo to give 4.01 g (70% yield) of 27a as a pale oil. $^1H$ NMR (400 MHz, $CDCl_3$) δ 3.46-3.38 (t, J=6.0 Hz, 2H), 2.56-2.46 (m, 1H), 1.95-1.60 (m, 4H), 1.25-1.20 (d, J=7.0 Hz, 3H); $^{13}C$ NMR (100 MHz, $CDCl_3$) δ 183.1, 38.9, 33.6, 32.1, 30.5, 17.3.

Example 5

2(S)-Methyl-6-bromohexanoic acid (25b). Compound 25b was produced in 77% yield from 24b following the procedure outlined for 25a. $^1H$ NMR (400 MHz $CDCl_3$) δ 3.45-3.38 (t, J=6.2 Hz, 2H), 2.55-2.45 (m, 1H), 1.92-1.85 (m, 2H), 1.77-1.68 (m, 1H), 1.55-1.46 (m, 3H), 1.24-1.19 (d, J=7.8 Hz, 3H); $^{13}C$ NMR (100 MHz, $CDCl_3$) δ 183.5, 39.5, 33.8, 32.9, 32.7, 26.0, 17.2.

Example 6

2(S)-Methyl-7-bromoheptanoic acid (25c). Compound 25c was produced in 74% yield from 24c following the procedure outlined for 25. $^1H$ NMR (400 MHz, $CDCl_3$) δ 3.43-3.36 (t, J=6.8 Hz, 2H), 2.51-2.42 (m, 1H), 1.90-1.64 (m, 3H), 1.49-1.32 (m, 5H) 1.20-1.14 (d, Hz, 3H); $^{13}C$ NMR (100 MHz, $CDCl_3$) δ 183.6, 39.5, 34.1, 33.5, 32.7, 28.2, 26.6, 17.1.

Example 7

Alpha Methyl, Alpha Desamino, Omega N-Substituted Homolysyl and Orinthyl (8) Neurotensin (8-13)

Figure 7:
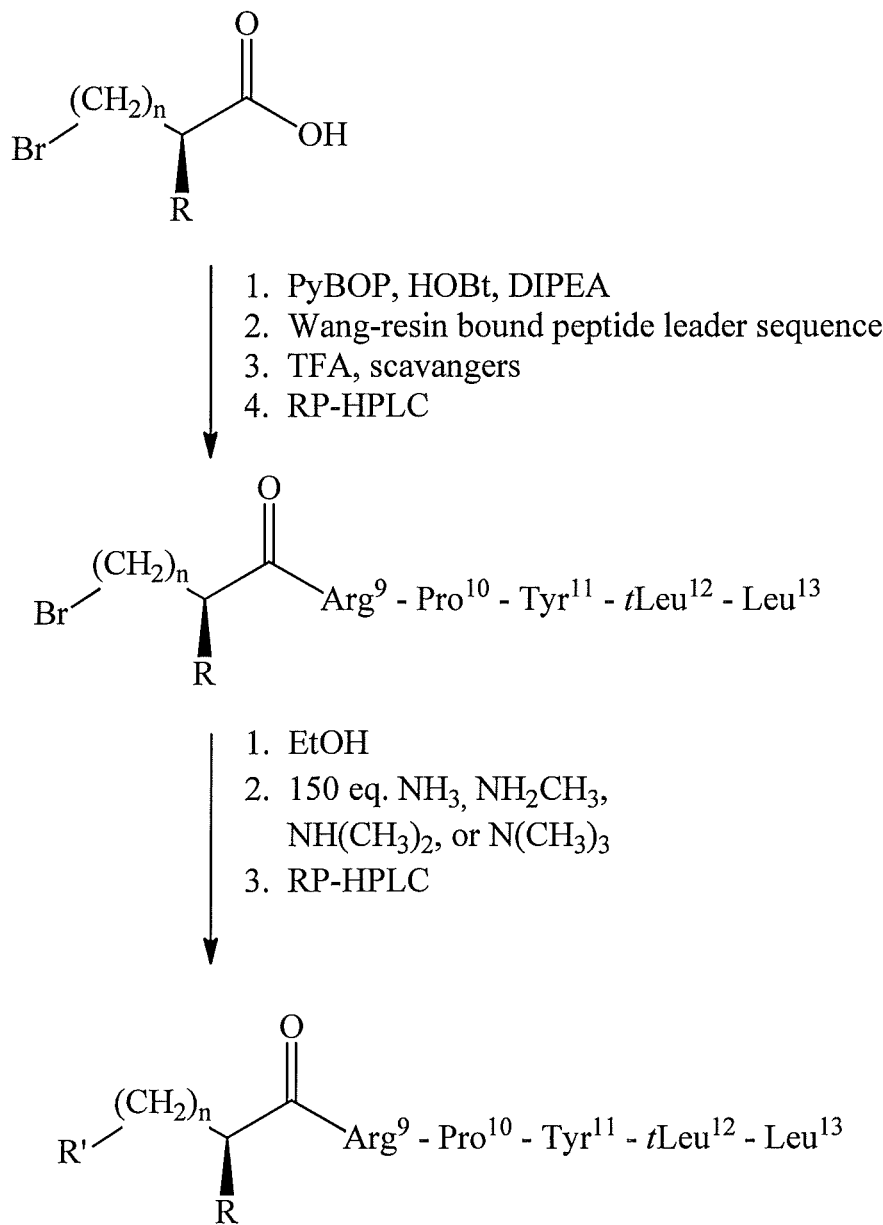
FIG. 7. Peptide synthesis of representative peptides of the invention.
Figure 8:
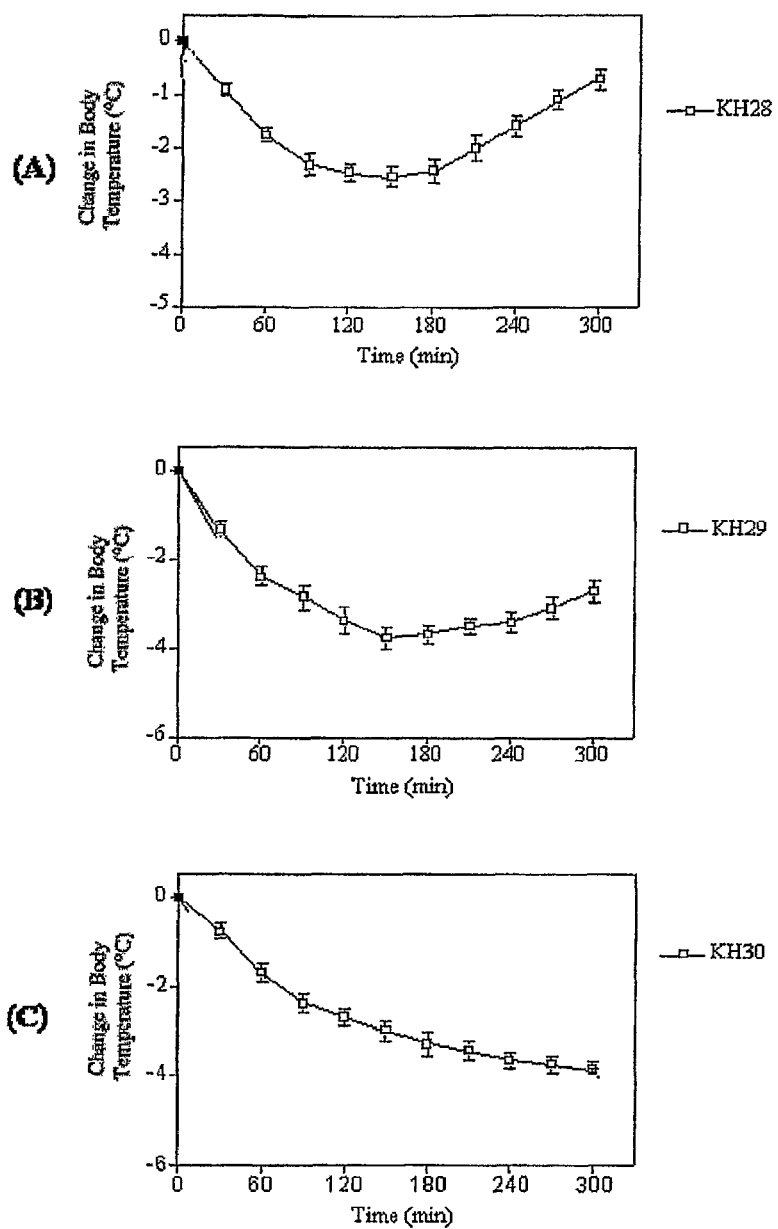
FIG. 8A-8C. Comparisons of induced hypothermia by α-methyl NT(8-13) analogues.

Alpha methyl, alpha desamino omega N-substituted homo lysyl and orinthyl (8) neurotensin (8-13) were synthesized (FIG. 7). The α-methyl bromo acids, 27a and c, were coupled to the resin-bound peptide as outlined in the general section. The solid state coupling was conducted as follows.

Resin bound N alpha Fmoc leucine was swelled in DMF prior to Fmoc cleavage with piperidine (20% in DMF). The piperidine solution was removed with vacuum filtration and the resin-bound amino acid washed with DMS and methylene chloride (5× each). Amino acids (4 eq) were activated in DMF with HOBt (4 eq) PyBOP ((4 eq) and DIPEA (10 eq) and added directly to the peptide reaction vessel. Amino acids were coupled for 6 hours, the resins was washed with DMF and methylene chloride and monitored with a Kaiser test for the presence of free amines. Residues were recoupled when necessary. This procedure was repeated with subsequent amino acids to give the penultimate peptide sequence (pentamer).

Aliquots of the resin-bound pentamer were then coupled with the appropriate omega bromo carboxylic acid as described above to give the N-omega bromo acyl pentamers. The N-omega acyl pentamers were then reacted with ammonia, dimethyl amine or trimethyl amine as described in these Examples to produce the desired peptides of the invention. Acid catalyzed deprotection of the side chain protecting groups was performed with a TFA solution containing appropriate scavengers.

RP-HPLC purification using a linear gradient of 15% to 75% B over 55 min at a constant flow rate of 4 mL/min afforded pure omega bromo peptides 53 and 54. These bromo peptides were reacted at 40° C. for 12 hr with 150 eq of ammonium hydroxide (29% in $H_2O$), methylamine (40% in $H_2O$), dimethylamine (40% in $H_2O$), or trimethylamine (40% in $H_2O$) in ethanol (EtOH). Solvents were removed in vacuo and crude peptides were taken up in mobile phase and purified with a linear gradient of 2% to 50% B over 65 min at a constant flow rate of 4 mL/min.

Peptides were characterized and assessed for purity via MALDI-TOFMS on a Voyager DE-STR System 4117 mass spectrometer (Applied Biosystems, Foster City, Calif.). Peptides were used at greater than 95% purity in vivo.

Example 8

NT(8-13) Peptides and their Hypothermia Bioactivity

General Animal Protocols. Male Sprague Dawley Rats (250-350 g) were obtained from Harlan (Indianapolis, Ind.) and housed in an AAALAC-approved colony room maintained at a constant temperature and humidity. Lighting was controlled on a 12 hr light:dark cycle with lights on at 0700 hr. Animals were housed two per cage with ad libitum access to food and water. All experiments were performed during the light cycle.

Animal Restraint. Rats were restrained in Plas-Labs® plastic cages fitted with wooden dowels to restrict movement. Rectal temperature probes (Physitemp®, RET-2, Clifton, N.J.), lubricated with mineral oil, were inserted into the rectum of each animal. Probes were connected to a microprobe thermometer (Physitemp®, BAT-12) in conjunction with a thermocouple selector (Physitemp®, SWT-5). Rats were allowed to acclimate to the cages for 1 hr prior to IP injection.

IP Injection. Peptides (5 mg/kg) were dissolved in saline (1 mL/kg). Following the equilibration period, rats were given an IP injection of peptide or saline Initial temperature values were the average temperatures of the rats immediately before and after the injection. Subsequent measurements were taken every 30 min for 5 hr. One-way repeated measures ANOVAs followed by Tukey's post hoc test for multiple comparisons were performed for each peptide using GraphPad Prism® to measure significance. Results were considered significant for $p<0.05$.

Example 9

Protocols and Results of Neurotesting of ABS201

Protocols

Dose-response curves for hypothermic induction. All animal restraint and hypothermia protocols were as described previously. Variable slope dose-response curve and $ED_{50}$ value was generated using GraphPad Prism®.

d-Amphetamine induced hyperlocomotion. Experimentally I male Sprague-Dawley rats were housed as described above. Rats were handled for three days prior to testing to minimize experimenter induced hyperlocomotion on test day. For experiments, sound- and light-attenuated automated photocell beam activity chambers (AccuScan Instruments, Inc., Columbus, Ohio) were used to measure locomotion. Cages were connected to a VersaMax Analyzer (AccuScan) in conjunction with an IBM computer using VersaMax 1.80-0146 software (AccuScan) to record vertical and horizontal activity. Total activity values recorded were the sum of vertical and horizontal activity. Rats were placed in the activity chambers for 1 hr to habituate and establish baseline activity levels. At 1 hr, rats were removed and given an IP or oral dose of peptide (N=7) or saline (N=8) and returned to the chamber to establish the peptide's effect on spontaneous activity levels. At 2 hr, rats were removed and given an IP injection of d-amphetamine (1 mg/kg) and returned to the chamber for a further 2 hr to assess the effect of the peptide on induced hyperlocomotion.

Chronic Testing Protocols. For chronic hypothermia testing, rats were given an IP injection of ABS201 (5 mg/kg) or saline once daily for five consecutive days. Induced hypothermia was monitored and tested for significance as described above. To assess the ability of ABS201 to decrease d-amphetamine induced hyperactivity after repeated administration, rats were divided into three dosing groups; chronic, acute, and control (N=7 for all groups). On days 1-4, the chronic group received an IP injection of ABS201 (5 mg/kg) while the acute and control groups received saline. On test day, day five, chronic and acute animals received ABS201 (5 mg/kg) while control animals received saline. The test protocol for day five was as described above.

Catalepsy Assessment. ABS201 (5 mg/kg) was dissolved in saline (1 ml/kg). A horizontal bar 5 mm in diameter was placed 7.5 cm above the cage floor. Rats were given an IP injection of peptide, saline, or haloperidol (1 mg/kg) and their front paws were placed directly on the bar. The rat was held in this position for 3 sec and then released. The time from release until the paws return to the cage floor was measured and recorded. A cut-off time of 30 sec was observed; this indicated a fully cataleptic animal. Measures were repeated every 30 min for 4 hr.

The results of these assessments are as follows.

Figure 11:
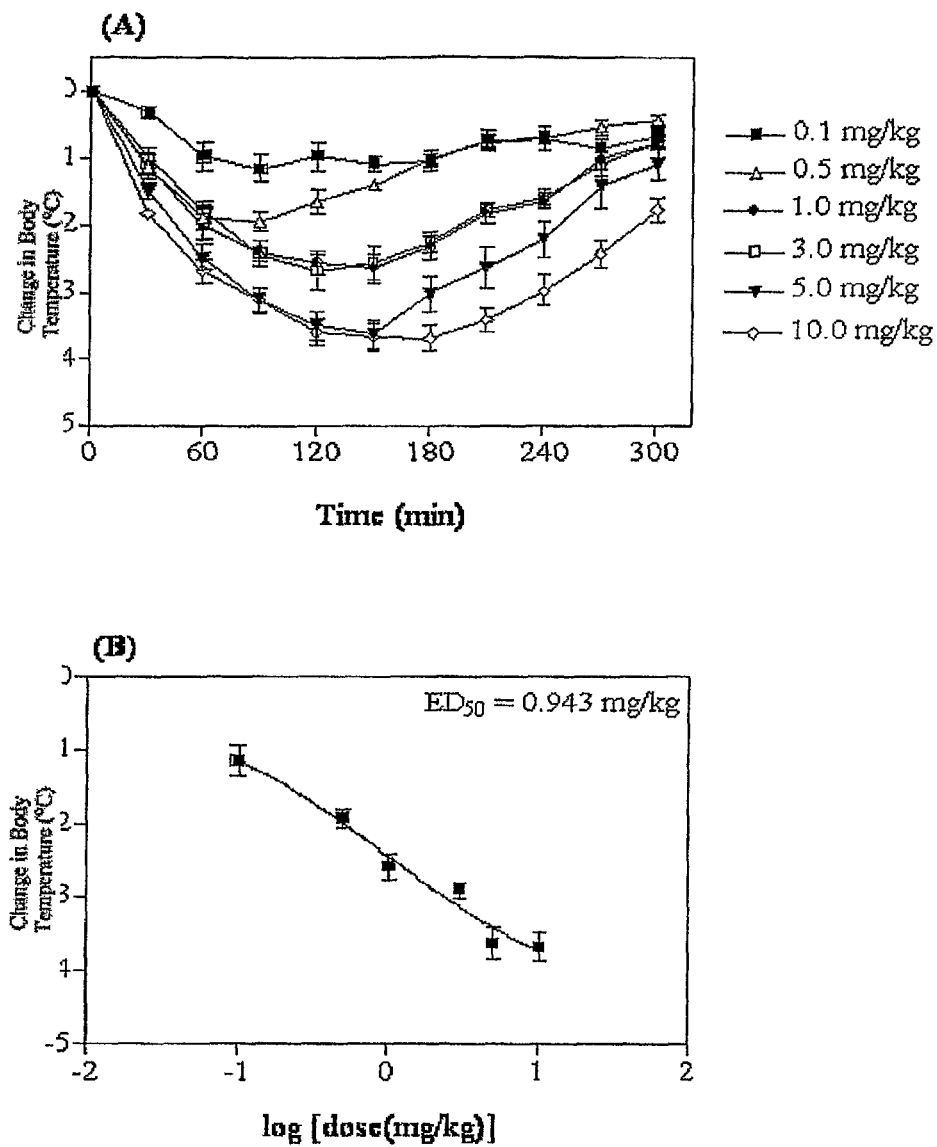
FIG. 11A-11B. Dose-response curves for ABS201 after IP administration.

Dose-response curves. The dose-response curve for ABS201 after IP injection over a concentration range of 0.1-10.0 mg/kg is shown in FIG. 11. The calculated $ED_{50}$, value is 0.943 mg/kg. The hypothermic response to the oral administration of ABS201 over a concentration range of 10.0-30.0 mg/kg is shown in FIG. 12.

Attenuation of d-amphetamine induced hyperlocomotion after IP dosing. Separate two-factor ANOVAs for DOSE X TIME were performed for each different time-phase of the assay. Phases consisted of habituation (time points 10-60), drug (time points 70-120), and amphetamine (time points 130-240). During the habituation phase, there was a main effect of TIME [$F(5,185)=264.335$ ($p<0.001$)], indicating a gradual decrease in activity levels over time regardless of dose. Tukey's post-hoc tests, collapsed over dose, indicated activity levels for time points 10-30 were significantly higher than time points 40-60 ($p<0.001$). These results are attributed to the initial spontaneous exploratory activity associated with the novel environment. During the drug phase, there was a main effect of TIME [$F(5,185)=12.336$ ($p<0.001$)] and a main effect of DOSE [$F(5,37)=11.775$ ($p<0.001$)]. The main effect of TIME resulted from a decrease in activity for all doses relative to the first time point (70 min). Tukey's post-hoc tests, collapsed over time, indicated that all doses responded significantly different from saline ($p<0.001$). During the amphetamine phase, there was DOSE X TIME interaction [$F(55,407)=4.474$ ($p<0.001$)]. Tukey's post-hoc tests revealed that all ABS201 dose groups demonstrated reduced locomotor activity for time points 130-200 as compared to saline ($p<0.05$).

Attenuation of d-amphetamine induced hyperlocomotion after oral dosing. Separate two-factor ANOVAs for DOSE X TIME were performed for each different time-phase of the assay. Phases were consistent with those described above. During the habituation phase, there was a main effect of TIME [$F(5,120)=201.979$ ($p<0.001$)], indicating a gradual decrease in activity levels over time, regardless of dose. Tukey's post-hoc tests, collapsed over dose, indicated activity levels significantly decreased at each time point. During the drug phase, there was DOSE X TIME interaction [$F(15,120)=11.584$ ($p<0.037$)]. Tukey's post-hoc tests, collapsed over time, indicated that only the 10 mg/kg and 30 mg/kg dose groups responded significantly different from saline ($p<0.01$). During the amphetamine phase, there was DOSE X TIME interaction [$F(11,264)=35.616$ ($p<0.001$)]. Tukey's post-hoc tests revealed that all dose groups demonstrated reduced locomotor activity for time points 140-180 as compared to saline ($p<0.05$). In addition, the 20 mg/kg and 30 mg/kg dose groups responded significantly lower than the saline group at time points 190-200.

Effects of chronic ABS201 administration of hypothermic induction. ABS201 maintained a significant CNS effect after repeated daily dosing (Table 3) and over the 5-day period the absolute hypothermic response increased.

Effects of repeated ABS201 dosing on d-amphetamine induced hyperactivity. Separate two-factor ANOVAs for GROUP X TIME were performed for each different time-phase of the experiment. Phases were consistent with those described above. During the habituation phase, there was a main effect of TIME [$F(5,90)=146.164$ ($p<0.001$)], indicating that there was a gradual decrease in activity levels over time, regardless of group. Tukey's post-hoc tests, collapsed over dose, indicated activity levels for time points 10-20 were significantly higher than time points 30-60 ($p<0.001$). These results are attributed to the habituation of the rats to a novel environment over time. During the drug phase, there was a main effect of TIME [$F(5,90)=13.512$ ($p<0.001$)] and a main effect of GROUP [$F(2,18)=4.37$ ($p=0.028$)]. The main effect of TIME resulted from a decrease in activity for all doses relative to the first time point (70 min). Tukey's post-hoc tests, collapsed over time, indicated that only the acute group responded significantly different from saline during the drug phase ($p<0.05$). During the amphetamine phase, there was GROUP X TIME interaction [$F(22.198)=4.069$ ($p<0.001$)]. Tukey's post-hoc tests revealed that both the acute and chronic groups demonstrated reduced locomotor activity for time points 140-220 as compared to saline ($p<0.05$).

Catalepsy assessment. Neither ABS201 (5 mg/kg) nor saline caused catalepsy after peripheral administration (N=5). Haloperidol, a typical APD known to produce a fully cataleptic response in rats, induced catalepsy that lasted for greater than 30 sec.

Example 10

Radioactive ABS201 for Oral Bioavailability Studies

Figure 18:
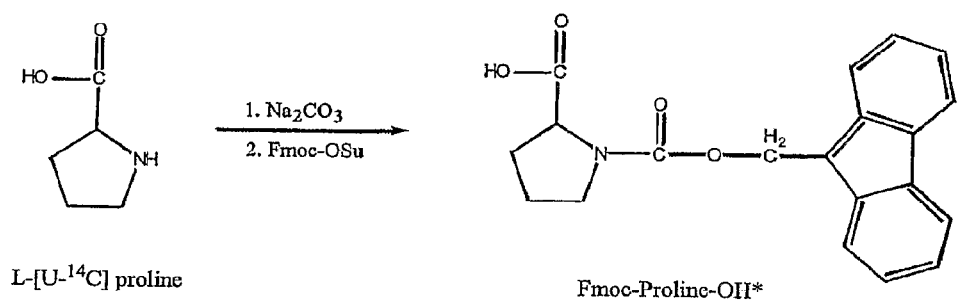
FIG. 18. Synthesis of Fmoc-Proline-OH*.

Synthesis of Fmoc-Proline-OH* (FIG. 18). L-Proline (20.7 mg, 0.18 mmol) (Advanced Chemtech) was dissolved in 450 μL of a 10% $Na_2CO_3$ solution to which 5 mL of $EtOH:H_2O$ (2:98) containing 250 μCi of L-[U-$^{14}$C]egrada (Moravek, Brea, Calif.) was added. Fmoc-N-hydroxysuccinimide (Fmoc-Osu) (100 mg, 1.5 eq) in 3 mL dimethoxyethane (DME) was added dropwise to the stirring amino acid solution. The reaction was allowed to stir for 12 hr at room temperature and the DME was removed in vacuo. The remaining aqueous solution was diluted with 10 mL $H_2O$ and extracted with saturated N-butanol (4×10 mL). The butanol extracts were combined and concentrated to give a pale oil. Residual Fmoc-Osu was removed on silica gel eluting with MeOH:CH$_2$Cl$_2$ (50:50). Crude Fmoc-Proline-OH* was used without further purification in peptide synthesis.

Example 11

Protocol and Study for ABS201 Oral Bioavailability Caco-2 Cell Model

Caco-2 cells, derived from a human colorectal carcinoma, spontaneously differentiate into polarized cells that exhibit well-developed microvilli and brush-border enzymes (78). These features make the cells an excellent model of the human small intestine. A strong correlation between uptake in the Caco-2 cell model and oral bioavailability has been identified (79). Studies that focused on the transport of peptides across Caco-2 cells have identified solute-solvent hydrogen bonds as a major determining factor in the permeability of the peptide. The non-natural amino acid technology is designed to reduce solute-solvent interactions, in particular, water solvation that occurs through hydrogen bonding, hence the current modifications should confer enhanced intestinal absorption in Caco-2 cells. The studies described below are designed to evaluate the potential oral bioavailability of the NT(8-13) analogues and the mechanisms of transport responsible for their uptake.

ABS201 is a lead compound for the development of NT(8-13) analogues as novel APDs. ABS201 can therefore function as a prototype for evaluating the cellular uptake of the NT(8-13) analogues. Liquid scintillation counting (LSC) is the preferred method of analysis for these assays, as extraction of the peptide from the cell monolayer is not required and dissolved cell components can be directly analyzed without an extraction protocol that can be inexact, resulting in inconsistent analysis. L-[U-$^{14}$C] αegrada was used as the radiolabel for these studies. Proline is easily protected at the α-amine for peptide synthesis with the base-labile Fmoc moiety. In addition, Pro$^{10}$ has not been identified as a major site of cleavage of NT(8-13). NT(8-13) analogues that show antipsychotic potential have not included Pro$^{10}$ modifications.

To examine the occurrence and mechanism of cellular uptake of the NT(8-13) analogues, Caco-2 cells, a well-established model of the intestinal epithelium can be utilized. These studies were designed to provide insight into the potential for oral activity of the peptide analogues. As described above, the NT(8-13) analogues elicit CNS activity after oral administration. They are the first analogues of NT(8-13) to exhibit oral activity, and these preliminary studies should provide information that aids in the development of future peptide analogues with enhanced oral activity.

The concentration of ABS201 used for these uptake studies, 200 μM, can be chosen for two distinct reasons. The concentration of a 20 mg/kg dose of peptide, delivered in saline (1 mL/kg), is 24 mM. As gavage dosing insures direct administration into the stomach, a concentration only slightly below 24 mM should be seen by the small intestine. Therefore, the concentration added to the Caco-2 cells is well below that theoretically seen in vivo. In addition, the standard circulating blood volume in the rat is 64 mL/kg (82). After gavage dosing, the concentration of a 20 mg/kg dose of peptide circulating throughout the entire rat is 377 μM. For these reasons, 200 μM is determined to be a physiologically relevant concentration to study ABS201 uptake in vitro.

Example 12

Structures of Compounds

The compounds evaluated in Example 12 contain one non-natural amino acid (Scheme 1) or desaminoacid (Scheme 2).

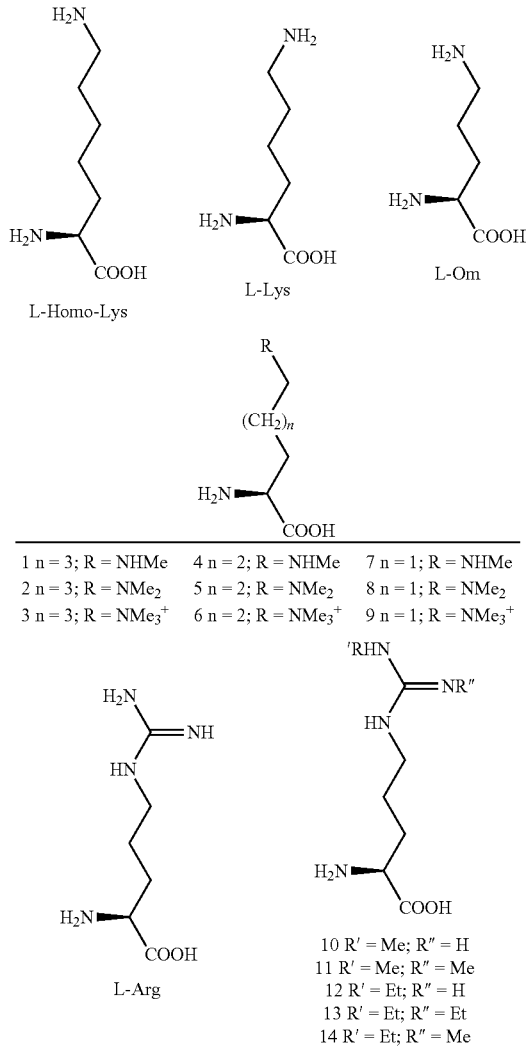

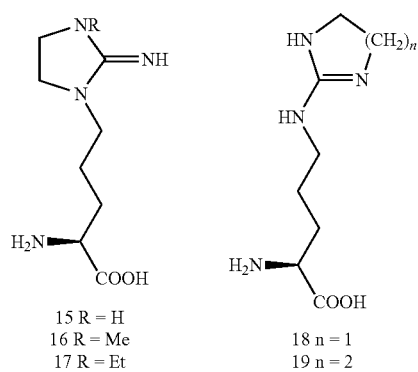

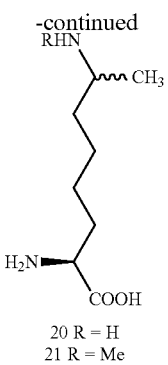

20 R = H
21 R = Me

Scheme 2. Desaminoalkylacids used in Example 12.

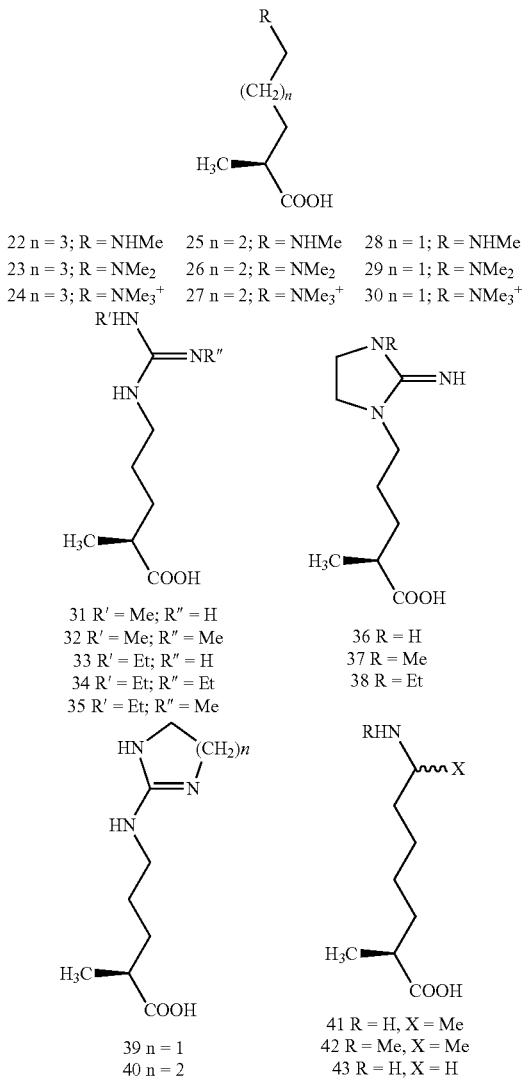

22 n = 3; R = NHMe    25 n = 2; R = NHMe    28 n = 1; R = NHMe
23 n = 3; R = NMe₂    26 n = 2; R = NMe₂    29 n = 1; R = NMe₂
24 n = 3; R = NMe₃⁺   27 n = 2; R = NMe₃⁺   30 n = 1; R = NMe₃⁺

31 R' = Me; R'' = H
32 R' = Me; R'' = Me
33 R' = Et; R'' = H
34 R' = Et; R'' = Et
35 R' = Et; R'' = Me

36 R = H
37 R = Me
38 R = Et 39 n = 1
40 n = 2

41 R = H, X = Me
42 R = Me, X = Me
43 R = H, X = H

Benchmarking Compounds

From an initial screen of about 50 compounds, those listed in Table 5 were selected for further testing and development as antipsychotic compounds. These compounds are based on the neurotensin fragment NT(8-13). These compounds possessed useful characteristics as each: bound as competitive agonists in vitro to NTR-1, the brain neurotensin receptor involved in schizophrenia, demonstrated central activity when injected IP in rat using hypothermia as a surrogate for central activity, which also occurs through NTR-1 binding and elicited the appropriate activities in rat behavioral models of schizophrenia.

TABLE 5

Structures of NT(8-13)-based peptides.
NT(98-13) (SEQ ID NO: 2); ABS13 (SEQ ID NO: 6);
ABS41 (SEQ ID NO: 7); ABS44 (SEQ ID NO: 8);
ABS46 (SEQ ID NO: 9); ABS201 (SEQ ID NO: 3);
ABS202 (SEQ ID NO: 10); ABS203 (SEQ ID NO: 11).

| Peptide # | Structure[1] |
|---|---|
| NT(8-13) | NH₂-Arg-Arg-Pro-Tyr-Ile-Leu-COOH |
| ABS13 | N₃-L-homolysine-Arg-Pro-Tyr-tertLeu-Leu-COOH |
| ABS41 | N₃-13-Arg-Pro-Tyr-Ile-tertLeu-COOH |
| ABS44 | N₃-7-Arg-Pro-Tyr-Ile-tertLeu-COOH |
| ABS46 | N₃-9-Arg-Pro-Tyr-Ile-tertLeu-COOH |
| ABS201 | 43-Arg-Pro-Tyr-Ile-tertLeu-COOH |
| ABS202 | 28-Arg-Pro-Tyr-Ile-tertLeu-COOH |
| ABS203 | 30-Arg-Pro-Tyr-Ile-tertLeu-COOH |

[1]Bolded numbers within peptide structures refer to the non-natural Arg and Lys residues shown in Schemes 1 and 2.

To further characterize the compounds, hypothermia induction (NTR-1 receptor binding) activity was evaluated with both oral and IP dosing of each compound. As seen in Table 6, all of the compounds except for ABS201 exhibited <10% oral activity. Interestingly, ABS201 had a 300% increase in oral activity over the previous most active compound. In addition, ABS201 achieved a faster response when administered orally versus IP. This is unique among the NT(8-13) derivatives.

TABLE 6

Hypothermic effects of NT(8-13) analogues after IP and oral administration.
ABS13 (SEQ ID NO: 6); ABS31 (SEQ ID NO: 12);
ABS44 (SEQ ID NO: 8); ABS46 (SEQ ID NO: 9);
ABS201 (SEQ ID NO: 3); ABS202 (SEQ ID NO: 10);
ABS203 (SEQ ID NO: 11).

| | IP Dose[a] | | Oral Dose[b] | | |
|---|---|---|---|---|---|
| Peptide | $t_{max}$[c] (min) | Δ in BT[d] (° C.) | $t_{max}$[c] (min) | Δ in BT[d] (° C.) | App. Oral |
| Saline | 240 | −0.60± | 180 | −0.64± | NA |
| ABS13 | 150 | −4.26± | 90 | −1.66± | |
| ABS31 | 180 | −6.87± | 150 | −1.05± | NA |
| ABS44 | 150 | −5.07± | 150 | −1.58± | |
| ABS46 | 180 | −4.68± | 180 | −2.03± | |
| ABS201 | 150 | −2.51± | 90 | −2.49± | |
| ABS202 | 150 | −3.75± | 120 | −1.09± | NA |
| ABS203 | 300 | −3.84± | 150 | −1.30± | NA |

[a]IP dose was 5 mg/kg for all peptides.
[b]Oral dose was 20 mg/kg for all peptides.
[c]$t_{max}$ (min) = Time to maximal temperature decrease.
[d]Δ in BT (° C.) = Decrease in body temperature measured at $t_{max}$.
[e]Denotes a significant response (p < 0.05).
[f]Approximate oral bioavailability was calculated from the relative areas under the hypothermia curve for each dosing regimen, corrected for amount of compound administered.
[g]NA = none apparent (as the oral dosing was not significant over baseline).

Behavioral Effects of ABS201

Figure 13:
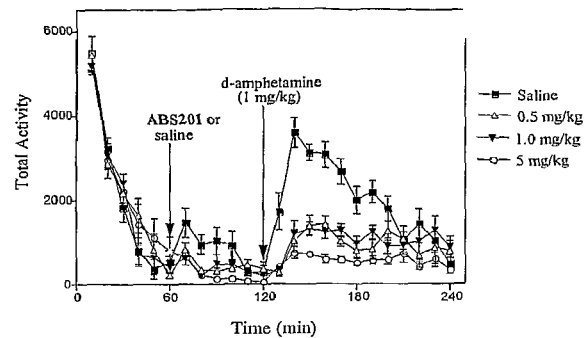
FIG. 13. Attenuation of d-amphetamine induced hyperactivity after IP administration of ABS201.
Figure 14:
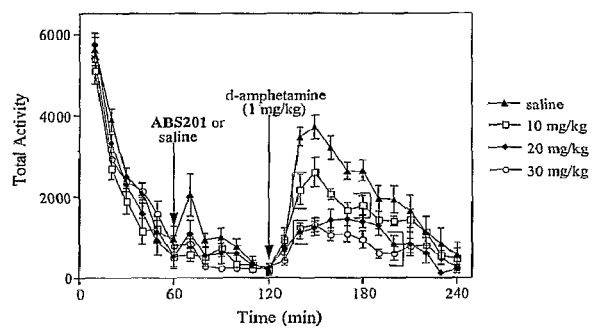
FIG. 14. Attenuation of d-amphetamine induced hyperactivity after oral administration of ABS201.

The "gold standard" animal model for evaluating a molecule with antipsychotic potential is inhibition of amphetamine-induced hyperlocomotion. ABS201 is active in a dose-dependent fashion whether IP or orally injected (FIGS. 13 and 14). The action of ABS201 is apparent following both IV and PO administration; dose-dependent; and long acting (observable 1 hr post administration and apparent for at least one additional hour).

Figure 15:
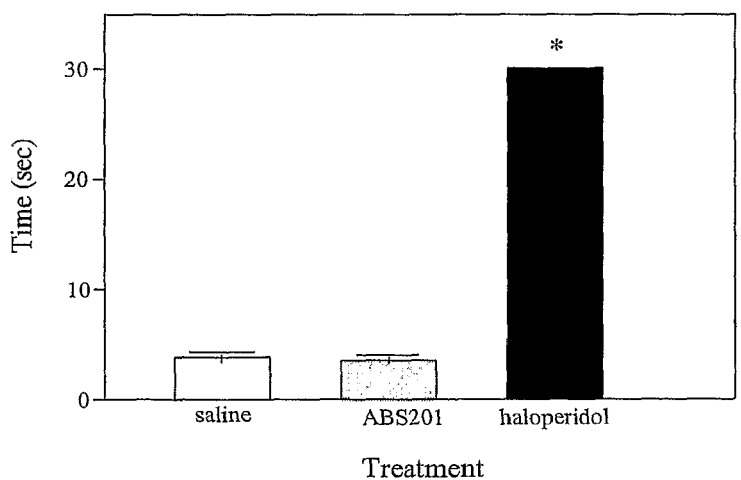
FIG. 15. Effect of ABS201 and haloperidol on catalepsy.
Figure 16:
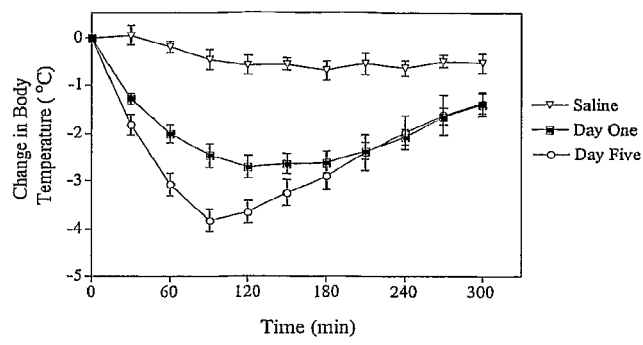
FIG. 16. Hypothermic effects of chronic administration of ABS201 after daily dose of 5 mg/kg ABS201.
Figure 17:
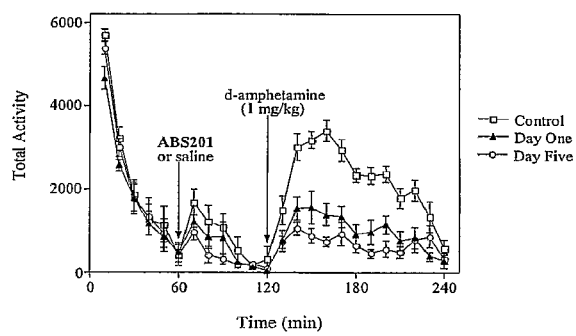
FIG. 17. Effect of repeated daily administration of ABS201 on d-amphetamine induced hyperlocomotion after daily doses of 5 mg/kg ABS201.

The effects of ABS201 and haloperidol on catalepsy was examined in rats. Rats (N=5) were given an IP injection of ABS201 (5 mg/kg) or haloperidol (1 mg/kg). After 2 h, catalepsy was measured using the horizontal bar test. Data are means +/−SEM (p<0.01). ABS201 does not induce a cataleptic state in rats (FIG. 15), is not antinociceptive, and tolerance to multiple dosings does not occur either with monitoring hypothermia or inhibition of amphetamine-induced hyperlocomotion (FIGS. 16 and 17). Thus, ABS201 reliably induces hypothermia in rodents following both IV and PO administration. The action of ABS201 is:dose-dependent; and long acting, being observable for a period of 3-4 hours following administration. The doses producing hypothermia are similar, if not identical, to those which reverse d-amphetamine responses.

The oral and intravenous dosing of 3 male and 3 female rats each receiving 50 mg/kg (IV) or 250 mg/kg (PO) of ABS201HCl administered in neutral physiological saline was observed. During the 2 and 24 hour post-dosing clinical observation periods, measurements of core body temperatures were taken.

The following was observed during the period immediately during and following intravenous administration of ABS201: during the dosing period (slow push; >1 min <2 min via the tail vein) the animals receiving ABS201HCl became noticeably sedate in the body restraining cages; upon removal from the restraining cages, animals were obviously sedated, lacked spontaneous benchtop locomotor activity, assumed a curl position upon handling, and exhibited a greatly impaired, or loss of, the righting reflex; notwithstanding, ptosis was absent; there was no evidence of flaccid paralysis although muscle tone was substantially reduced; pupil reflex was present; the hind limb pinch response was impaired or absent; there was no evidence of parasympathetic responses, e.g., spontaneous urination, defecation, salivation and lacrimation were absent; there was no evidence of acute sympathetic responses, e.g., piloerection; there was no evidence of seizures, either tonic or clonic. The acute effects were short lived with the righting reflex returning by the end of the complete dosing period (approximately 30 min). At the two hour post-dosing observation period, all animals appeared grossly normal although marked hypothermia was present. At the 24 hour post-dosing observation period, all animals appeared grossly normal; hypothermia was absent. Animals administered ABS201HCl orally appeared grossly normal at all time points. Thus, the evidence indicates that the acute behavioral appearance and response(s) of animals following the intravenous administration of ABS201HCl (50 mg/kg) is directly attributable to a rapid and marked central nervous system effect.

Preclinical Studies of ABS201

Receptor Screening

Three separate concentrations of ABS201 ($10^{-9}$, $10^{-7}$ $10^{-5}$ M) were screened individually against the following 16 receptors: adrenergic (alpha1, alpha 2, beta), dopamine, histamine (H1, H2, H3), muscarinic (central, peripheral), nicotinic, opioid (nonselective), orphanin, serotonin (transporter, nonselective), monoamine oxidase (A, B). No displacement of the receptors' endogenous substrate were observed. Hence ABS201 does not appear to bind with any of these receptors. In contrast, the ABS201 has nM affinity for the target receptor ($NTR_1$).

Blood Distribution and Metabolite Identification

ABS201 was added to freshly isolated whole rat blood to a concentration of 100 μg/mL, allowed to partition, and the cellular fraction was removed by centrifugation. ABS201 at this concentration distributes almost evenly between the cellular and serum fractions. No metabolites of ABS201 were been detected, consistent with previous experiments in which a very long serum/plasma half-live was demonstrated.

Maximum Tolerated Dose

ABS201 was administered to rats at IV doses up to 100 mg/kg and oral doses up to 500 mg/kg. No adverse effects of the compound (body weight loss, mortality, abnormal clinical evaluations panel) were seen out to 48 hr post administration. These experiments thus define lower limits for the MTD of ABS201 at 100 times the $ED_{50}$ for the compound in antipsychosis and other tests reflective of brain activity.

Pharmacokinetics and Brain Distribution of ABS201

ABS201 was administered in one IV dose (5 mg/kg) or oral dose (50 mg/kg) to rats. At selected time points, blood was removed or brain harvested and the concentration of the compound determined. It was demonstrated that ABS201 could be detected in the blood and brain up to 120 minutes after both IV and oral administration. The amount in the brain was sufficient to saturate NTR-1 to produce the observed behavioral effects.

The plasma and brain pharmacokinetics of ABS201 was studied following IV administration of 1 mg/kg and, oral administration of 30 mg/kg of ABS201 to non fasted rats. The results of this study indicated that: ABS201 was rapidly cleared from plasma following IV administration with a $t_{1/2}$ of about 5 minutes; the levels of the compound decreased below the LLOD by 45 min; the levels of ABS201 were below the LLOD at all times following oral administration; and the levels of ABS201 in brain were below the LLOD at all times following both IV and PO administration.

In vitro metabolism and compartmentalization of ABS201 was also studied to evaluate the distribution of ABS201 in blood, the extent of protein binding in plasma, and to gain a preliminary assessment of the metabolism of ABS201 in blood and plasma. The results of this study demonstrated: little or no binding of ABS201 to plasma proteins following a 5 or 30 min incubation at 37° C.; no evidence of metabolism of ABS201 in whole blood or plasma following a 5 or 30 min incubation at 37° C.; and a rapid distribution of about 33 percent of ABS201 into blood cellular elements when whole blood was incubated with ABS201 for 5 or 30 min at 37° C.

The whole blood and brain pharmacokinetics of ABS201 following IV administration of 5 mg/kg and PO administration of 50 mg/kg of ABS201 to fasted rats was also evaluated. The results of this study indicated: ABS201 was cleared from whole blood in two phases with an initial phase and a second phase where compound was measurable at low levels up to 120 minutes following IV administration of 5 mg/kg; the levels of ABS201 in whole blood were below the LLOD at all times following oral administration of the compound (50 mg/kg); the levels of ABS201 in brain were below the LLOD at all times following IV administration; and measurable quantities of ABS201 were detected in brains of 2 of 3 animals 15 minutes post oral administration of 50 mg/kg.

Summary

Substitution of the N-terminal α-azido group of homolysine (Scheme 1) of ABS13 with the methyldesamino derivative 43 (Scheme 2) to produce ABS201 resulted in a molecule possessing important characteristics of a potential antipsychotic. In particular, ABS201 exhibited a 300% increase in central activity when administered orally, and achieved a more rapid response with oral versus IV injection. These unique attributes are attributable to the desamino modification.

The pharmacokinetics, compartmentalization, and possible metabolism of ABS201 were evaluated in vitro and in vivo. The results suggest little or no metabolism, and complex pharmacokinetics which indicate that the compound initially undergoes a rapid clearance from blood, followed by a longer lasting, deep compartment phenomenon.

Also, the pharmacodynamic response of ABS201 is long acting (2-4 hr) following both IV and PO administration; the acute effects of IV ABS201 are mediated via central nervous system; the compound does not appear to be metabolized upon co-incubation with plasma or whole blood; ABS201 partitions between the aqueous and cellular phases of blood in vitro; the PK profile of ABS201 in whole blood is consistent with a two phase clearance process; and the pharmacodynamic response which has been observed is likewise consistent with a two phase clearance process.

Given the long apparent half life of ABS201 in rat brain (detectable to 6 hours post dosing), and evidence that the drug forms a depot in blood elements (i.e., a slow release delivery system for the drug) the compounds of the invention, such as the semisynthetic peptide ABS201, could be administered on a once or twice daily basis.

LIST OF DOCUMENTS

The following list of documents provide background information, synthetic information, scientific information, protocols and related disclosures. The complete text of each document is incorporated herein as an integral part of this application as if it were fully repeated, and all publications, patents and patent applications cited herein are herein incorporated by reference.

(1) Rowley, M., Bristow, L. J., and Hutson, P. H., "Current and novel approaches to the drug treatment of schizophrenia." *J Med Chem.* 44: 477-501, 2001.

(2) Kitabgi, P. and Nemeroff, C. B. Eds. "The Neurobiology of Neurotensin." *Ann NY Acad Sci.* 668: 1-374, 1992.

(3) Kapur, S., Remington, G., Jones, C., Wilson, A., DaSilva, J., Houle, S., and Zipursky, R. "High levels of dopamine $D_2$ receptor occupancy with low dose haloperidol treatment: a PET study." *Am J Psych.* 153: 948-50, 1996.

(4) Alvir, J. M. J., Lieberman, J. A., Safferman, A. Z., Schwimmer, J. L., and Schaff, J. A. "Clozapine-induced agranulocytosis: incidence and risk factors in the United States." *New Eng J Med.* 329: 162, 1993.

(5) Andreasen, N. C., Arndt, S., Swayze, V., Cizadlo, T., Flaum, M., Oleary, D., Ehrhardt, J C., and Yuh, W. T. C. "Thalamic abnormalities in schizophrenia visualized through magnetic resonance imaging averaging." *Science.* 266: 294-98, 1994.

(6) Lawrie, S. M. and Abukmeil, S. S. "Brain abnormality in schizophrenia. A systematic and quantitative review of volumetric magnetic resonance imaging studies." *Br J Psych.* 55: 433-40, 1998.

(7) Silberweig, D. A., Stern, E., Frith, C., Cahill, C., Holmes, A., Grootoonk, S., Seaward, J., McKenna, P., Chua, S. E., and Schnorr, L. "A functional neuroanatomy of hallucinations in schizophrenia." *Nature.* 378: 176-79, 1995.

(8) McGaffin, P. Owen, M. J., and Farmer, A. E. "Genetic basis of schizophrenia." *Lancet.* 346: 678-82, 1995.

(9) Carlsson, A. and Lindquist, M. "Effect of chlorpromazine and haloperidol on formation of methoxytyramine and normetanephrine in mouse brain." *Acta Pharmacol Toxicol.* 20: 140-44, 1963.

(10) Creese, I., Burt, D. R., and Snyder, S. H. "Dopamine receptor binding predicts clinical and pharmacological potencies of antischizophrenic drugs." *Science.* 192: 481-83, 1976.

(11) Nyberg, S., Nakashima, Y., Nordstrom, A. L., Hallidin, C., and Farde, L. "Positron emission tomography of in vivo binding characteristics of atypical antipsychotic drugs: review of $D_2$ and 5-$HT_2$ receptor occupancy studies and clinical response." *Br J Psych.* 168 (suppl 29): 40-44, 1996.

(12) Carraway, R. and Leeman, S. E "The isolation of a new hypotensive peptide, neurotensin, from bovine hypothalami." *J Biol Chem.* 248: 6854-61, 1973.

(13) Bissette, G., Nemeroff, C. B., Loosen, P. T., Prange Jr., A. J., and Lipton, M A. "Hypothermia and intolerance to cold induced by intracisternal administration of the hypothalamic peptide neurotensin." *Nature.* 262: 607-9, 1976.

(14) Nemeroff, C. B., Osbahr, A. J., Manberg, P. J., Ervin, G. N., and Prange Jr., A J. "Alterations in nociception and body temperature after intracisternal administration of neurotensin, β-endorphin, other endogenous peptides, and morphine" *Proc Natl Acad Sci USA.* 76: 5368-71, 1979.

(15) Skoog, K. M., Cain, S. T., and Nemeroff, C B. "Centrally administered neurotensin suppresses locomotor hyperactivity induced by d-amphetamine but not by scopolamine or caffeine." *Neuropharm.* 25:777-82, 1986.

(16) Nemeroff, C. B., Bissette, G., Prange Jr., A. J., Loosen, P. T., Barlow, T. S., and Lipton, M. A. "Neurotensin: central nervous system effects of a hypothalamic peptide." *Brain Res.* 128: 485-96, 1977.

(17) Kitabgi, P., Checker, F., Mazella, J., and Vincent, J. P. "Pharmacology and biochemistry of neurotensin receptors." *Rev Clin Basic Pharmacol.* 5: 397-486, 1985.

(18) Carraway, R. and Leeman, S E. "The amino acid sequence of a hypothalamic peptide, neurotensin." *J Biol Chem.* 250: 1907-11, 1975.

(19) Carraway, R. and Leeman, S E. "Structural requirements for the biological activity of neurotensin, a new vasoactive peptide." Edited by R. Walter and J. Meienhofer. *Peptides: Chemistry, Structure, and Biology.* Ann Arbor: Ann Arbor Science, 1975, p. 679-85.

(20) Tanaka, K., Masu, M., and Nakanishi, S. "Structure and functional expression of the cloned rat neurotensin receptor." *Neuron.* 4: 847-54, 1990.

(21) Vita, N., Laurent, P., Lefort, S., Chalon, P., Dumont, X., Kaghad, M., Gully, D., Le Fur, G., Ferrara, P., and Caput, D. "Cloning and expression of a complementary DNA encoding a high affinity human neurotensin receptor." *FEBS Lett.* 317: 139-42, 1993.

(22) Hermans, E. and Maloteaux, J. "Mechanisms of regulation of neurotensin receptors." *Pharmacol Ther.* 79: 89-104., 1998.

(23) Vincent, J. P. "Neurotensin receptors: binding properties, transduction pathways, and structure." *Cell Mol Neurobiol.* 15: 501-12, 1995.

(24) Chalon, P., Vita, N., Kaghad, M., Guillemot, M., Bonnin, J., Delpech, B., Le Fur, G., Ferrara, P., and Caput, D. "Molecular cloning of a levocabastine-sensitive neurotensin binding site." *FEBS Lett.* 386: 91-4, 1996.

(25) Vita, N., Oury-Donat, F., Chalon, P., Guillemot, M., Kaghad, M., Bachy, A., Thurneyssen, O., Garcia, S., Poinot-Chazel, C., Casellas, P., Keane, P., Le Fur, G., Maffrand, J. P., Soubrie, P., Caput, D., and Ferrara, P. "Neurotensin is an antagonist of the human neurotensin NT2 receptor expressed in Chinese hamster ovary cells." *Eur J Pharmacol.* 360: 265-72, 1998.

(26) Vincent, J. P., Mazella, J., and Kitabgi, P. "Neurotensin and neurotensin receptors." *Trends Pharm Sci.* 20: 302-9, 1999.

(27) Mazella, J., Zsurger, N., Navarro, V., Chabry, J., Kaghad, M., Caput, D., Ferrara, P., Vita, N., Gully, D., Maffrand, J. P., and Vincent, J. P. "The 100 k-Da neurotensin receptor is gp95/sortilin, a non-U-protein-coupled receptor." *J Biol Chem.* 273: 26273-6, 1998.

(28) Binder, E. B., Kinkead, B., Owens, M. J., and Nemeroff, C. B. "The role of neurotensin in the pathophysiology of action of antipsychotic drugs." *Biol Psych.* 50: 856-72, 2001.

(29) Binder, E. B., Kinkead, B., Owens, M. J., and Nemeroff, C. B. "Neurotensin and dopamine interactions." *Pharm Reviews.* 53: 453-86, 2001.

(30) Quirion, R., Rowe, W. B., Lapchak, P. A., Araujo, D. M., and Beaudet, A. "Distribution of neurotensin receptors in mammalian brain. What it is telling us about its interactions with other neurotransmitter systems." *Ann NY Acad Sci.* 668: 109-19, 1992.

(31) Kinkead, B., Binder, E. B., and Nemeroff, C. B. "Does neurotensin mediate the effects of antipsychotic drugs?" *Biol Psychiatry.* 46: 340-51, 1999.

(32) Garver, D. L., Bissette, G., Yao, J. K., and Nemeroff, C. B. "Relation of CSF neurotensin concentrations to symptoms and drug response of psychotic patients." *Am J Psych.* 148: 484-88, 1991.

(33) Breslin, N. A., Suddath, R. L., Bissette, G., Nemeroff, C. B., Lowrimore, P., and Weinberger, D. R. "CSF concentrations of neurotensin in schizophrenia: An investigation of clinical and biochemical correlates." *Schizophr Res.* 12: 35-41, 1994.

(34) Sharma, R. P., Janicak, P. G., Bissette, G., and Nemeroff, C. B. "CSF neurotensin concentrations and antipsychotic treatment in schizophrenia and schizoaffective disorder." *Am J Psych.* 154: 1019-21, 1997.

(35) Kitabgi, P., Poustis, C., Granier, C., Van Rietschoten, J., Rivier, J., Morgat, J. L., and Freychet, P. "Neurotensin binding to extraneural and neural receptors: comparison with biological activity and structure-activity relationships." *Mol Pharmacol.* 18: 11-19, 1980.

(36) Fuxe, K., Von Euler, G., Agnati, L. F., Merlo Pich, E., O'Connor, W. T., Tanganelli, S., et al. "Intermembrane interactions between neurotensin receptors and dopamine $D_2$ receptors as a major mechanism for the neuroleptic-like action of neurotensin." *Ann NY Acad Sci.* 668: 186-204, 1992.

(37) Li, X. M., Ferraro, L., Tanganelli, S., O'Connor, W. T., Hasselrot, U., Ungerstedt, U., et al. "Neurotensin peptides antagonistically regulate postsynaptic dopamine $D_2$ receptors in rat nucleus accumbens: A receptor binding and microdialysis study." *J Neural Trans.* 102: 125-37, 1995.

(38) Binder, E. B., Kinkead, B., Owens, M. J., Kilts, C. D., and Nemeroff, C. B. "Enhanced neurotensin neurotransmission is involved in the clinically relevant behavioral effects of antipsychotic drugs: evidence from animal models of sensorimotor gating." *J Neurosci.* 21: 601-8, 2001.

(39) Al-Rodhan, N. R., Richelson, E., Gilbert, J. A., McCormick, D. J., Kanba, K. S. Pfenning, M. A., Nelson, A., Larson, E. W., and Yaksh, T. L. "Structure-antinociceptive activity of neurotensin and some novel analogues in the periaqueductal gray region of the brainstem." *Brain Res.* 557(1-2): 227-35, 1991.

(40) Pettibone, D. J., Hess, J. F., Hey, P. J., Jacobson, M. A., Leviten, M., Lis, E. V., Mallorga, P. J., Pascarella, O. M., Snyder, M. A., Williams, J. B., and Zeng, Z. "The effects of deleting the mouse neurotensin receptor NTR1 on central and peripheral responses to neurotensin." *J Pharm Exp Ther.* 300: 305-313, 2001.

(41) Tyler-McMahon, B. M., Stewart, J. A., Farinas, F., McCormick, D. J., and Richelson, E. "Highly potent neurotensin analog that causes hypothermia and antinociception." *Eur J Pharmacol.* 390: 107-11, 2000.

(42) Farra, C. D., Sarret, P., Navarro, V., Botto, J. M., Mazella, J., and Vincent, J. P. "Involvement of the neurotensin receptor subtype NTR3 in the growth effect of neurotensin on cancer cell lines." *Int J Cancer.* 92: 503-9, 2001.

(43) Moody, T. W., Chiles, J., Casibang, M., Moody, E., Chan, D., and Davis, T. P. "SR48692 is a neurotensin receptor antagonist which inhibits the growth of small cell lung cancer cells." *Peptides.* 22: 109-15, 2001.

(44) Iwase, K., Evers, B. M., Hellmich, M, R., Kim, H. J., Higashide, S., Gully, D., Thompson, J. C., and Townsend Jr., C. M. "Inhibition of neurotensin-induced pancreatic cancer growth by a nonpeptide neurotensin receptor antagonist, SR48692." *Cancer.* 79: 1787-93, 1997.

(45) Schiinpff, R. M., Avard, C., Fenelon, G., Lhiaubet, A. M., Tenneze, L., Vidailbet, M., and Rostene, W. "Increased plasma neurotensin concentrations in patients with Parkinson's disease." *J Neurol Neuro Psych.* 70: 784-6, 2001.

(46) Boules, M., Warrington, L., Fauq, A., McCormick, D., and Richelson, E. "Antiparkinson-like effects of a novel neurotensin analog in unilaterally 6-hydroxydopamine lesioned rats." *Eur J Pharmacol.* 428: 227-33, 2001.

(47) Beeson, C. C. and Dix, T. A. "Thermodynamic description of a contact and solvent-separated ion pair as a function of solvation: A model for salt bridges and proton-transfer reactions in biology." *J Am Chem Soc.* 115: 10275-81, 1993.

(48) Kennedy, K. J., Lundquist, J. T., Simandan, T. L., Kokko, K. P., Beeson, C. C., and Dix, T. A. "Design rational, synthesis, and characterization of non-natural analogs of the cationic amino acids arginine and lysine." *J Pept Res.* 55: 348-58, 2000.

(49) Cusack, B., McCormick, D. J., Pang, Y. P., Sonder, T., Garcia, R., Fauq, A., and Richelson, E. "Pharmacological and biochemical profiles of unique neurotensin 8-13 analogs exhibiting species selectivity, stereoselectivity, and superagonism." *J Biol Chem.* 270: 18359-66, 1995.

(50) Lundquist, J. T. and Dix, T. A. "Synthesis and human neurotensin receptor binding activities of neurotensin(8-13) analogues containing position 8 alpha-azido-N-alkylated derivatives of ornithine, lysine, and homolysine." *J Med Chem.* 42: 4914-8, 1999.

(51) Lee, Y. C., Uttenthal, L. O., Smith, H. A., and Bloom, S. R. "In vitro degradation of neurotensin in human plasma." *Peptides.* 7: 383-7, 1986.

(52) Kokko, K. P., Hadden, M. K., Price, K. L., Orwig, K. S., See, R. E., and Dix, T A. "Pharmacokinetic and behavioral effects of stable, receptor-selective neurotensin(8-13) analogues that cross the blood-brain barrier." *Neuropharm.* Under Revision.

(53) Kokko, K. P. and Dix, T A. "Monitoring neurotensin [8-13] degradation in human and rat serum utilizing matrix-assisted laser desorption/ionization time-of-flight mass spectrometry." *Anal Biochem.* 308: 34-41, 2002.

(54) Kokko, K. P., Hadden, M. K., Orwig, K. S., Mazella, J., and Dix, T. A. "In vitro analysis of stable, receptor-selective neurotensin(8-13) analogues." *J Med Chem.* 46: 4141-48, 2003.

(55) Tyler-McMahon, B. M., Boules, M., and Richelson, E. "Neurotensin: peptide for the next millennium." *Reg Pept.* 93: 125-36, 2000.

(56) Bednarek, M. A., Macneil, T., Kalyani, R. N., Tang, R., Van der Ploeg, L. H. T., and Weinberg, D. H. "Analogs of MTII, lactam derivatives of α-melanotropin, modified at the N-terminus, and their selectivity at human melanocortin receptors 3, 4, and 5." *Biochem Biophys Res Comm.* 261: 209-13, 1999.

(57) Lunquist, J. T. and Dix, T. A. "Asymmetric synthesis of ω-bromo-2(S)-azido acids as precursors for the synthesis of novel amino acids." *Tet Lett.* 39: 775-8, 1998.

(58) Evans, D. A., Britton, T. C., Ellman, J. A., and Dorow, R. L. "The asymmetric synthesis of α-amino acids. Electrophilic azidation of chiral imide enolates, a practical approach to the synthesis of (R)- and (S)-α-azido carboxylic acids." *J Am Chem Soc.* 112: 4011-30, 1990.

(59) Taylor, R. E., Galvin, G. M., Hilfiker, K. A., and Chen, Y. "A formal total synthesis of epothilone A: Enantioselective preparation of the C1-C6 and C7-C12 fragments." *J Org Chem.* 63: 9580-3, 1998.

(60) Boules, M., McMahon, B., Warrington, L., Stewart, J., Jackson, J., Fauq A., McCormick, D., and Richelson, E. "Neurotensin analog selective for hypothermia over antinociception and exhibiting atypical neuroleptic-like properties." *Brain Res.* 919: 1-11, 2001.

(61) Dubuc, I., Remande, S., and Costentin, J "The partial agonist properties of levocabastine in neurotensin-induced analgesia." *Eur J Pharmacol.* 381: 9-12, 1999.

(62) Kennedy, K. J., Simandan, T. L., and Dix, T A. "A facile route to cyclic and acyclic alkyl-arginines." *Synthetic Comm.* 28: 741-6, 1998.

(63) Lundquist, J. T., Orwig, K. S., and Dix, T. A "Synthesis of ethylene-bridge ($N^\delta$ to $N^\omega$) analogues of arginine." *J Org Chem.* 64:9265-7, 1999.

(64) Lundquist, J. T., and Pelletier, J. C. "Improved solid-phase peptide synthesis method utilizing alpha-azide protected amino acids." *Org Lett.* 3: 781-3, 2001.

(65) Meienhofer, J., Waki, M., Heimer, E. P., Lambros, T. J., Makofske, R., and Chang, C. C. "Solid phase synthesis without repetitive acidolysis; preparation of leucyl-alanyl-glycyl-valine using 9-fluorenylmethyloxylcarbonyl amino acids." *Int J Pep Pro Res.* 13: 35-42, 1979.

(66) Kaiser, E., Colescott, R. L., Bossinger, C. D., and Cook, P. I. "Color test for detection of free terminal amino groups in the solid-phase synthesis of peptides." *Anal Biochem.* 34: 595-98, 1970.

(67) Boules, M., Warrington, L., Fauq, A., McCormick, D., and Richelson, E. "A novel neurotensin analog blocks cocaine- and D-amphetamine-induced hyperactivity." *Eur J Pharmacol.* 426: 73-6, 2001.

(68) Tyler, B. M., Douglac, C. L., Faur, A., Pang, Y. P., Stewart, J. A., Cusack, B., McCormick, D. J., and Richelson, E. "In vitro binding and CNS effects of novel neurotensin agonists that cross the blood-brain barrier." *Neuropharm.* 38: 027-34, 1999.

(69) Richelson, E., Cusack, B., Pang, Y. P., McCormick, D. J., Fauq, A., Tyler, B. M., and Boules, M. U.S. Pat. No. 6,214,790. *United States Patent and Trademark Office*, Mayo Foundation for Medical Education and Research, USA, 2000.

(70) Machida, R., Tokumura, T., Tsuchiya, Y., Sasaki, A., and Abe, K. "Pharmacokinetics of a novel hexapeptide with neurotensin activity in rats." *Biol Pharm Bull.* 16: 43-7, 1993.

(71) Ogren, S. O. "The behavioural pharmacology of typical and atypical antipsychotic drugs." *Handbook of Experimental Pharmacology*. Edited by J. G. Csernansky, Springer, Berlin, 1996, p. 225-66.

(72) Jones, G. H. and Robbins, T. W. "Differential effects of mesocortical, mesolimbic, and mesostriatal dopamine depletion on spontaneous, conditioned and drug-induced locomotor activity." *Pharmacol Biochem Behav.* 43: 887-95, 1992.

(73) Hertel, P., Byskov, L., Didriksen, M., and Arnt, J. "Induction of tolerance to the suppressant effect of the neurotensin analogue NT69L on amphetamine-induced hyperactivity." *Eur J Pharmacol.* 422: 77-81, 2001.

(74) Lowe, J. A., Seeger, T. F., and Vineck F. J. "Atypical antipsychotics—recent findings and new perspectives." *Med Res Rev.* 8: 475-97, 1998.

(75) Dunn, A. J., Snijders, R., Hurd, R. W., and Kramery, N. R. "Induction of catalepsy by central nervous system administration of neurotensin." *Ann NY Acad Sci.* 400: 345-53, 1982.

(76) Sarhan, S., Hitchcock, J. M., Grauffel, C. A., and Wettstein, J. G. "Comparative antipsychotic profiles of neurotensin and a related systemically active peptide agonist." *Peptides.* 18: 1223-27, 1997.

(77) Cusack, B., Boules, M., Tyler, B. M., Fauq, A., McCormick, D. J., and Richelson, E. "Effects of a novel neurotensin peptide analog given extracranially on CNS behaviors mediated by apomorphine and haloperidol." *Brain Res.* 865: 48-54, 2000.

(78) Hilgers, A. R., Conradi, R. A., and Burton, P. S. "Caco-2 cell monolayers as a model for drug transport across the intestinal mucosa." *Pharm Res.* 7: 902-10, 1990.

(79) Artursson, P. and Karlsson, J. "Correlation between drug absorption in humans and apparent drug permeability coefficients in human intestinal epithelial (Caco-2) cells." *Biochem Biophy Res Comm.* 175: 880-5, 1991.

(80) Borchardt, R. T. "Optimizing oral absorption of peptides using prodrug strategies." *J Cont Rel.* 62: 231-38, 1999.

(81) Conradi, R. A., Hilgers, A. R., Ho, N. F. H., and Burton, P. S. "The influence of peptide structure on transport across Caco-2 cells." *Pharm Res.* 8: 1453-60, 1991.

(82) McGuill, M. W. and Rowan, A. N. "Biological effects of blood loss; implication for sampling volumes and techniques." *ILAR Journal.* 31(4), 1989.

(83) Lowry, O. H., Rosenbrough, N. J., Farr, A. L., and Randall, R. J. "Protein measurement with the folin phenol reagent." *J Biol Chem.* 193: 265-75, 1951.

(84) Hadjiagapiou, C., Schmidt, L., Dudeja, K., Layden, T J., and Ramaswamy, K. "Mechanism(s) of butyrate transport in Caco-2 cells: role of monocarboxylate transporter 1." *Am J Physiol.* 279: G775-80, 2000.

(85) Brandsch, M., Miyamoto, Y., Ganaphthy, V., and Liebach, F. "Expression of protein kinase C-dependent regulation of peptide/$H^+$ co-transport system in the Caco-2 human carcinoma cell line." *Biochem J.* 299: 253-60, 1994.

(86) Garcia, C. K., Goldstein, J. L., Pathak, R. K., Anderson, R. G. W., and Brown, M. S. "Molecular characterization of a membrane transporter for lactate, pyruvate and other monocarboxylates: implications for the cori cycle." *Cell.* 76: 865-73, 1994.

(87) Tamai, I., Sai, Y., Ono, A., Kido, Y., Yabuuchi, H., Takanaga, H., Satoh, E., Ogihara, T., Amano, O., Izeki, S., and Tsuji, S. "Immunohistochemical and functional characterization of pH-dependent intestinal transport of weak organic acids by the monocarboxylic acid transporter MCT1." *J Pharm Pharmacol.* 51: 1113-21, 1999.

(88) Tamai, I., Onashi, R., Nezu, J., Yabuuchi, H., Oku, A., Shimane, M., Sai, Y., and Tsuji, A. "Molecular and functional identification of sodium ion-dependent, high affinity human carnitine transporter OCTN2." *J Biol Chem.* 273: 20378-82, 1998.

(89) Walgren R. A., Karnaky, K. J., Lindenmayer, G. E., and Walle, T. "Efflux of dietary flavonoid quercetin 4'-β-glucoside across human intestinal Caco-2 cell monolayers by apical multidrug resistance-associated protein-2." *J Pharm Exp Ther.* 294:830-6, 2000.

(90) Hunter, J., Jepson, M. A., Tsuruo, T., Simmons, N. L., and Hirst, B. H. "Functional expression of P-glycoprotein in apical membranes of human intestinal Caco-2 cells. Kinetics of vinblastine secretion and interaction with modulators." *J Biol Chem.* 268: 14991-7, 1993.

(91) Jedlitschky, G., Leier, I., Buchholz, U., Center, M., and Keppler, D. "ATP-dependent transport of glutathione S-conjugates by the multidrug-resistance-associated protein." *Cancer Res.* 54: 4833-36, 1994.

(92) Bohme, M., Buchler, M., Muller, M., and Keppler, D. "Differential inhibition by cyclosporins of primary-active ATP-dependent transporters in the hepatocyte canalicular membranes." *FEBS Lett.* 333: 193-6, 1993.

(93) Hayer-Zillgen, M., Brass, M., and Bonisch, H. "Expression and pharmacological profile of the human organic cation transporters hOCT1, hOCT2, and hOCT3." *Br J Pharmacol.* 136: 829-36, 2002.

(94) Grundemann, D., Liebich, G., Kiefer, N., Koster, S., and Schomig, E. "Selective substrates for non-neuronal monoamine transporters." *Mol Pharmacol.* 56; 1-10, 1999.

(95) Mentlein, R. and Dahms, P. "Endopeptidases 24.16 and 24.15 are responsible for the egradation of somatostatin, neurotensin, and other neuropeptides by cultivated rat cortical astrocytes." *J Neurochem.* 62; 27-36, 1994.

(96) Lipinski, C. A., Lombardo, F., Dominy, B. W., Feeney, P. J., "Experimental and computational approaches to estimate solubility and permeability in drug discovery and development settings." *Adv Drug Del Rev.* 46: 3-26, 2001.

(97) Kilts, C. D. "Animal behavioral models of schizophrenia." *Current Issues in the Psychology of Schizophrenia*, edited by A. Breier. Lippincott Williams and Wilkins, 2001, p. 111-130.

Additional advantages of the invention in part will be obvious from the description, or may be learned by practice of the invention. The advantages of the invention will be realized and attained by means of the elements and combinations particularly pointed out in the appended claims.

Throughout this application, where publications are referenced, the disclosures of these publications in their entireties are hereby incorporated by reference into this application in order to more fully describe the state of the art to which this invention pertains.

What is claimed is:

1. A non-natural desamino, alkyl amino acid compound of Formula I is:

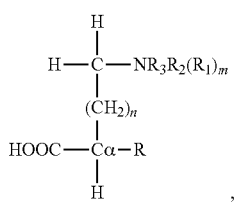

(I)

wherein
n is 3, 4, or 5;
m is 0 or 1;
R is a straight or branched chain $C_1$-$C_6$ alkyl group;
$R_1$, $R_2$, and $R_3$ are independently selected from the group consisting of: H; branched or straight chain $C_1$-$C_6$ alkyl, $C_2$-$C_6$ alkenyl or $C_2$-$C_6$ alkenyl; a protecting group that is removable by a chemical method that does not also cause cleavage of other groups; a $C_6$-$C_{18}$ aromatic group, wherein the aromatic group is optionally substituted with one or two substituents independently selected from the group consisting of halogen, alkyloxy, carboxy, amide and alkyl; and a $C_4$-$C_{18}$ heteroaromatic group and one or two heteroatoms independently selected from the group consisting of oxygen and sulfur, wherein the heteroaromatic group is optionally substituted with one or two substituents independently selected from the group consisting of halogen, alkyloxy, carboxy, amide and alkyl,
with the proviso that a maximum of two of $R_1$, $R_2$, and $R_3$ are aromatic, substituted aromatic, heteroaromatic or substituted heteroaromatic group; and Cα is a carbon atom and the stereochemistry at C is either R or S;
or an ester, amide, alkyl amide or metal cation or ammonium salt of the carboxylic acid group thereof, or an organic or inorganic acid salt of the amine group thereof, or any combination thereof.

2. The compound of claim 1, wherein the stereochemistry at Cα is S.

3. The compound of claim 1, wherein $R_1$, $R_2$, and $R_3$ are independently H or methyl.

4. The compound of claim 1, wherein R is methyl.

5. The compound of claim 1, wherein the compound is selected from the group consisting of compounds 22-24:

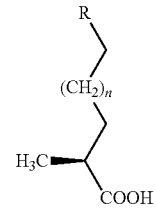

22 n = 3; R = NHMe
23 n = 3; R = $NMe_2$
24 n = 3; R = $NMe_3^+$.

6. The compound of claim 1, wherein the protecting group is BOC (t-butoxy carbonyl), FMOC (fluorenylmethoxycarbonyl), Alloc (allyloxycarbonyl), CBZ (benzyloxycarbonyl), Pbf (2,2,4,6,7- pentamethyl-dihydrobenzofuran-5-sulfonyl), $NO_2$ (nitro), Pmc (2,2,5,7,8-pentamethylchroman-6-sulfonyl), Mtr (4-methoxy-2,3,6-trimethylbenzenesulfonyl), or Tos (tosyl).

7. A peptide comprising a residue of Formula (I), wherein the residue of Formula (I) is the N-terminus residue of the peptide:

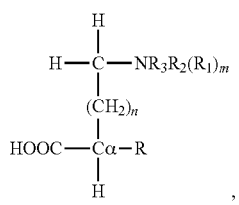

wherein:
n is 3, 4, or 5;
m is 0 or 1;
R is a straight or branched chain $C_1$-$C_6$ alkyl group;
$R_1$, $R_2$, and $R_3$ are independently selected from the group consisting of: H;
branched or straight chain $C_1$-$C_6$ alkyl, $C_2$-$C_6$ alkenyl or $C_2$-$C_6$ alkynyl; a protecting group that is removable by a chemical method that does not also cause cleavage of other groups; a $C_6$-$C_{18}$ aromatic group, wherein the aromatic group is optionally substituted with one or two substituents independently selected from the group consisting of halogen, alkyloxy, carboxy, amide and alkyl; and a $C_4$-$C_{18}$ heteroaromatic group and one or two heteroatoms independently selected from the group consisting of oxygen and sulfur, wherein the heteroaromatic group is optionally substituted with one or two substituents independently selected from the group consisting of halogen, alkyloxy, carboxy, amide and alkyl,
with the proviso that a maximum of two of $R_1$, $R_2$, and $R_3$ are aromatic, substituted aromatic, heteroaromatic or substituted heteroaromatic group; and
Cα is a carbon atom and the stereochemistry at C is either R or S; wherein the carboxylic acid (COOH) group of the residue of Formula (I) is covalently coupled within the peptide through an amide bond.

8. The peptide of claim 7 wherein the residue is covalently coupled through an amide bond to the N-terminus amine group of a given peptide, or the residue is a substitute for a natural amino acid moiety at the N-terminus of a given peptide,
wherein the given peptide is selected from the group consisting of a transcription factor, a ligand for a cellular receptor, a hormone and an extracellular binding peptide.

9. The peptide of claim 8, wherein the given peptide is neurotensin(8-13) and wherein the residue is a substitute for a natural amino acid moiety at the N-terminus of neurotensin (8-13).

10. The peptide of claim 9, wherein the peptide comprises ABS201 (SEQ ID NO:3).

11. The peptide of claim 8, wherein the given peptide is enkephalin, LHRH, a neuropeptide, a glycoincretin, integrin, a glucagon, a glucagon-like peptide, an antithrombotic peptide, a cytokine, an interleukin, a transferrin, an interferon, an endothelin, a natriuretic hormone, an extracellular kinase ligand, an angiotensin enzyme inhibitor, a peptide antiviral compound, thrombin, substance P, substance G, somatotropin, somatostatin, GnRH, secretin, bradykinin, vasopressin, insulin, neurotensin, proinsulin, or a growth factor.

12. The peptide of claim 8, wherein the peptide has an extended half-life in vivo or in vitro, as compared to the given peptide.

13. The peptide of claim 8, wherein the peptide has an increased ability to cross a biological barrier in a patient, as compared to the given peptide.

14. A pharmaceutical composition comprising a pharmaceutical carrier and a peptide comprising a residue of Formula (I), wherein the residue of Formula (I) is the N-terminus residue of the peptide:

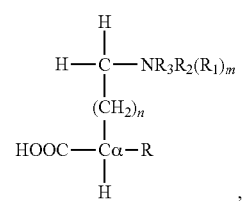

wherein:
n is 3, 4, or 5;
m is 0 or 1;
R is a straight or branched chain $C_1$-$C_6$ alkyl group;
$R_1$, $R_2$, and $R_3$ are independently selected from the group consisting of: H; branched or straight chain $C_1$-$C_6$ alkyl, $C_2$-$C_6$ alkenyl or $C_2$-$C_6$ alkynyl; a protecting group that is removable by a chemical method that does not also cause cleavage of other groups; a $C_6$-$C_{18}$ aromatic group, wherein the aromatic group is optionally substituted with one or two substituents independently selected from the group consisting of halogen, alkyloxy, carboxy, amide and alkyl; and a $C_4$-$C_{18}$ heteroaromatic group and one or two heteroatoms independently selected from the group consisting of oxygen and sulfur, wherein the heteroaromatic group is optionally substituted with one or two substituents independently selected from the group consisting of halogen, alkyloxy, carboxy, amide and alkyl,
with the proviso that a maximum of two of $R_1$, $R_2$, and $R_3$ are aromatic, substituted aromatic, heteroaromatic or substituted heteroaromatic group; and
Cα is a carbon atom and the stereochemistry at C is either R or S; wherein the carboxylic acid (COOH) group of the residue of Formula (I) is covalently coupled within the peptide through an amide bond.

15. The composition of claim 14, wherein the peptide is present in unit dosage form.

16. A cosmetic formulation comprising a cosmetic base formulation and a compound of Formula I:

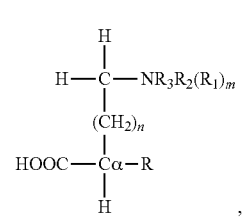

wherein:
n is 3, 4, or 5;
m is 0 or 1;
R is a straight or branched chain $C_1$-$C_6$ alkyl group;
$R_1$, $R_2$, and $R_3$ are independently selected from the group consisting of: H; branched or straight chain $C_1$-$C_6$ alkyl, $C_2$-$C_6$ alkenyl or $C_2$-$C_6$ alkynyl; a protecting group that is removable by a chemical method that does not also cause cleavage of other groups; a $C_6$-$C_{18}$ aromatic group, wherein the aromatic group is optionally substituted with one or two substituents independently selected from the group consisting of halogen, alkyloxy, carboxy, amide and alkyl; and a $C_4$-$C_{18}$ heteroaromatic group and one or two heteroatoms independently selected from the group consisting of oxygen and sulfur, wherein the heteroaromatic group is optionally substituted with one or two substituents independently selected from the group consisting of halogen, alkyloxy, carboxy, amide and alkyl, with the proviso that a maximum of two of $R_1$, $R_2$, and $R_3$ are aromatic, substituted aromatic, heteroaromatic or substituted heteroaromatic group; and $C\alpha$ is a carbon atom and the stereochemistry at C is either R or S; or an ester, amide, alkyl amide or metal cation or ammonium salt of the carboxylic acid group thereof, or an organic or inorganic acid salt of the amine group thereof, or any combination thereof.

17. The cosmetic formulation of claim 16, wherein the cosmetic base formulation is an aqueous or oil base.

18. A cosmetic formulation comprising a cosmetic base formulation and a peptide comprising a residue of Formula (I), wherein the residue of Formula (I) is the N-terminus residue of the peptide:

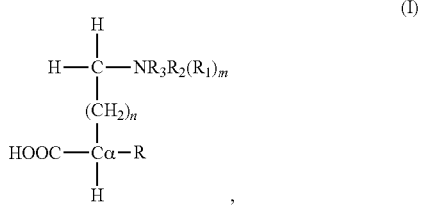

wherein:
n is 3, 4, or 5;
m is 0 or 1;
R is a straight or branched chain $C_1$-$C_6$ alkyl group;
$R_1$, $R_2$, and $R_3$ are independently selected from the group consisting of: H; branched or straight chain $C_1$-$C_6$ alkyl, $C_2$-$C_6$ alkenyl or $C_2$-$C_6$ alkynyl; a protecting group that is removable by a chemical method that does not also cause cleavage of other groups; a $C_6$-$C_{18}$ aromatic group, wherein the aromatic group is optionally substituted with one or two substituents independently selected from the group consisting of halogen, alkyloxy, carboxy, amide and alkyl; and a $C_4$-$C_{18}$ heteroaromatic group- and one or two heteroatoms independently selected from the group consisting of oxygen and sulfur, wherein the heteroaromatic group is optionally substituted with one or two substituents independently selected from the group consisting of halogen, alkyloxy, carboxy, amide and alkyl, with the proviso that a maximum of two of $R_1$, $R_2$, and $R_3$ are aromatic, substituted aromatic, heteroaromatic or substituted heteroaromatic group; and $C\alpha$ is a carbon atom and the stereochemistry at C is either R or S; wherein the carboxylic acid (COOH) group of the residue of Formula (I) is covalently coupled within the peptide through an amide bond.

19. The cosmetic formulation of claim 18, wherein the cosmetic base formulation is an aqueous or oil base.

20. A method of lowering the body temperature of a patient in need thereof, the method comprising administering to the patient an effective amount of a peptide comprising a residue of at least non-natural desamino, alkyl amino acid compound of Formula (I):

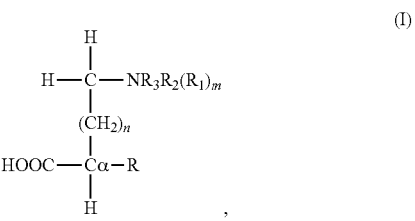

wherein:
n is 3, 4, or 5;
m is 0 or 1;
R is a straight or branched chain $C_1$-$C_6$ alkyl group;
$R_1$, $R_2$, and $R_3$ are independently selected from the group consisting of: H; branched or straight chain $C_1$-$C_6$ alkyl, $C_2$-$C_6$ alkenyl or $C_2$-$C_6$ alkynyl; a protecting group that is removable by a chemical method that does not also cause cleavage of other groups; a $C_6$-$C_{18}$ aromatic group, wherein the aromatic group is optionally substituted with one or two substituents independently selected from the group consisting of halogen, alkyloxy, carboxy, amide and alkyl; and a $C_4$-$C_{18}$ heteroaromatic group and one or two heteroatoms independently selected from the group consisting of oxygen and sulfur, wherein the heteroaromatic group is optionally substituted with one or two substituents independently selected from the group consisting of halogen, alkyloxy, carboxy, amide and alkyl, with the proviso that a maximum of two of $R_1$, $R_2$, and $R_3$ are aromatic, substituted aromatic, heteroaromatic or substituted heteroaromatic group; and $C\alpha$ is a carbon atom and the stereochemistry at C is either R or S;

or an ester, amide, alkyl amide or metal cation or ammonium salt of the carboxylic acid group thereof, or an organic or inorganic acid salt of the amine group thereof, or any combination thereof;

wherein the residue within the peptide is bound to the peptide via at least one amide bond, wherein the peptide is optionally administered to the patient as part of a pharmaceutical composition.

21. A method of treating cancer in a patient in need thereof, the method comprising administering to the patient an effective amount of a peptide comprising a residue of at least non-natural desamino, alkyl amino acid compound of Formula (I):

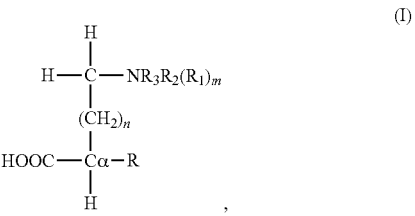

wherein:
n is 3, 4, or 5;
m is 0 or 1;
R is a straight or branched chain $C_1$-$C_6$ alkyl group;

$R_1$, $R_2$, and $R_3$ are independently selected from the group consisting of: H; branched or straight chain $C_1$-$C_6$ alkyl, $C_2$-$C_6$ alkenyl or $C_2$-$C_6$ alkynyl; a protecting group that is removable by a chemical method that does not also cause cleavage of other groups; a $C_6$-$C_{18}$ aromatic group, wherein the aromatic group is optionally substituted with one or two substituents independently selected from the group consisting of halogen, alkyloxy, carboxy, amide and alkyl; and a $C_4$-$C_{18}$ heteroaromatic group and one or two heteroatoms independently selected from the group consisting of oxygen and sulfur, wherein the heteroaromatic group is optionally substituted with one or two substituents independently selected from the group consisting of halogen, alkyloxy, carboxy, amide and alkyl, with the proviso that a maximum of two of $R_1$, $R_2$, and $R_3$ are aromatic, substituted aromatic, heteroaromatic or substituted heteroaromatic group; and C$\alpha$ is a carbon atom and the stereochemistry at C is either R or S;

or an ester, amide, alkyl amide or metal cation or ammonium salt of the carboxylic acid group thereof, or an organic or inorganic acid salt of the amine group thereof, or any combination thereof;

wherein the residue within the peptide is bound to the peptide via at least one amide bond, wherein the peptide is optionally administered to the patient as part of a pharmaceutical composition.

22. A method of treating pain in a patient in need thereof, the method comprising administering to the patient an effective amount of a peptide comprising a residue of at least non-natural desamino, alkyl amino acid compound of Formula (I):

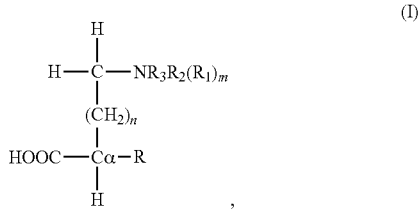

wherein:
n is 3, 4, or 5;
m is 0 or 1;
R is a straight or branched chain $C_1$-$C_6$ alkyl group;
$R_1$, $R_2$, and $R_3$ are independently selected from the group consisting of: H; branched or straight chain $C_1$-$C_6$ alkyl, $C_2$-$C_6$ alkenyl or $C_2$-$C_6$ alkynyl; a protecting group that is removable by a chemical method that does not also cause cleavage of other groups; a $C_6$-$C_{18}$ aromatic group, wherein the aromatic group is optionally substituted with one or two substituents independently selected from the group consisting of halogen, alkyloxy, carboxy, amide and alkyl; and a $C_4$-$C_{18}$ heteroaromatic group and one or two heteroatoms independently selected from the group consisting of oxygen and sulfur, wherein the heteroaromatic group is optionally substituted with one or two substituents independently selected from the group consisting of halogen, alkyloxy, carboxy, amide and alkyl, with the proviso that a maximum of two of $R_1$, $R_2$, and $R_3$ are aromatic, substituted aromatic, heteroaromatic or substituted heteroaromatic group; and C$\alpha$ is a carbon atom and the stereochemistry at C is either R or S;

or an ester, amide, alkyl amide or metal cation or ammonium salt of the carboxylic acid group thereof, or an organic or inorganic acid salt of the amine group thereof, or any combination thereof;

wherein the residue within the peptide is bound to the peptide via at least one amide bond, wherein the peptide is optionally administered to the patient as part of a pharmaceutical composition.

23. A method of treating a patient with psychosis in need thereof, the method comprising administering to the patient an effective amount of a peptide comprising a residue of at least non-natural desamino, alkyl amino acid compound of Formula (I):

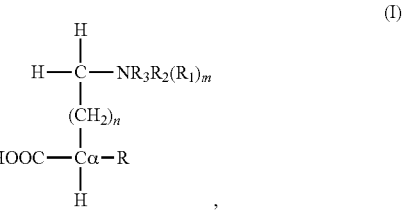

wherein:
n is 3, 4, or 5;
m is 0 or 1;
R is a straight or branched chain $C_1$-$C_6$ alkyl group;
$R_1$, $R_2$, and $R_3$ are independently selected from the group consisting of: H; branched or straight chain $C_1$-$C_6$ alkyl, $C_2$-$C_6$ alkenyl or $C_2$-$C_6$ alkynyl; a protecting group that is removable by a chemical method that does not also cause cleavage of other groups; a $C_6$-$C_{18}$ aromatic group, wherein the aromatic group is optionally substituted with one or two substituents independently selected from the group consisting of halogen, alkyloxy, carboxy, amide and alkyl; and a $C_4$-$C_{18}$ heteroaromatic group and one or two heteroatoms independently selected from the group consisting of oxygen and sulfur, wherein the heteroaromatic group is optionally substituted with one or two substituents independently selected from the group consisting of halogen, alkyloxy, carboxy, amide and alkyl, with the proviso that a maximum of two of $R_1$, $R_2$, and $R_3$ are aromatic, substituted aromatic, heteroaromatic or substituted heteroaromatic group; and C$\alpha$ is a carbon atom and the stereochemistry at C is either R or S;

or an ester, amide, alkyl amide or metal cation or ammonium salt of the carboxylic acid group thereof, or an organic or inorganic acid salt of the amine group thereof, or any combination thereof;

wherein the residue within the peptide is bound to the peptide via at least one amide bond, wherein the peptide is optionally administered to the patient as part of a pharmaceutical composition.

24. The method of claim 23, wherein the psychosis is schizophrenia.

* * * * *